United States Patent
George et al.

(10) Patent No.: US 9,296,687 B2
(45) Date of Patent: Mar. 29, 2016

(54) MODULATORS OF HSP70/DNAK FUNCTION AND METHODS OF USE THEREOF

(71) Applicants: The Trustees of the University of Pennsylvania, Philadelphia, PA (US); Fox Chase Cancer Center, Philadelphia, PA (US)

(72) Inventors: Donna L. George, Blue Bell, PA (US); Julia I-Ju Leu, Philadelphia, PA (US); Maureen Murphy, Stockton, NJ (US)

(73) Assignees: Fox Chase Cancer Center, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/048,540

(22) Filed: Oct. 8, 2013

(65) Prior Publication Data

US 2014/0087005 A1 Mar. 27, 2014

Related U.S. Application Data

(60) Division of application No. 13/051,511, filed on Mar. 18, 2011, now abandoned, which is a continuation-in-part of application No. PCT/US2009/057430, filed on Sep. 18, 2009.

(60) Provisional application No. 61/098,476, filed on Sep. 19, 2008.

(51) Int. Cl.
*A01N 41/06* (2006.01)
*A61K 31/18* (2006.01)
*C07C 311/13* (2006.01)
*A61K 45/06* (2006.01)
*A61K 31/436* (2006.01)
*A61K 33/24* (2006.01)
*A61N 5/10* (2006.01)

(52) U.S. Cl.
CPC ............... *C07C 311/13* (2013.01); *A61K 31/18* (2013.01); *A61K 31/436* (2013.01); *A61K 33/24* (2013.01); *A61K 45/06* (2013.01); *A61N 5/1001* (2013.01)

(58) Field of Classification Search
None
See application file for complete search history.

(56) References Cited

U.S. PATENT DOCUMENTS

| | | | |
|---|---|---|---|
| 5,476,659 A * | 12/1995 | Goodman et al. | 424/278.1 |
| 5,652,115 A | 7/1997 | Marks et al. | |
| 5,863,938 A * | 1/1999 | Martin | 514/461 |
| 6,824,555 B1 | 11/2004 | Towler et al. | |
| 2002/0090358 A1* | 7/2002 | Spaner | 424/93.7 |
| 2005/0020534 A1 | 1/2005 | Johnson et al. | |
| 2006/0057568 A1 | 3/2006 | Schmidt et al. | |
| 2007/0142308 A1 | 6/2007 | Augustin et al. | |
| 2008/0193928 A1* | 8/2008 | Castro et al. | 435/6 |

FOREIGN PATENT DOCUMENTS

JP 52125146 A 10/1977

OTHER PUBLICATIONS

Steele et al., "2-Phenylacetylenesulfonamide Upregulates Noxa and Induces p-53 Independent Apoptosis of CLL Cells," Blood (ASH Annual Meeting Abstracts) 2007 110: Abstract 1609.*
Moulin et al., "Sensitization of chronic lymphocytic leukemia cells to TRAIL-induced apoptosis by hyperthermia," Cancer Letters 250 (2007) pp. 117-127.*
Patani et al., "Bioisosterism: A Rational Approach in Drug Design," Chem. Rev. 1996, 96, 3147-3176.*
Strom, E., et al. "Small-molecule inhibitor of p53 binding to mitochondria protects mice from gamma radiation." Nat Chem Biol. Sep. 2006;2(9):474-9. Epub Jul. 23, 2006.
Zhou, P., et al. "ErbB2 degradation mediated by the co-chaperone protein CHIP." J Biol Chem. Apr. 18, 2003;278(16):13829-37. Epub Feb. 6, 2003.
Hasegawa et al., "The photobromination of .beta.-styrenesulfonannides and syntheses of 2-arylacetylene-1-sulfonamides," Bulletin of the Chemical Society of Japan, 59(9): 2346-2350 (1977).

* cited by examiner

*Primary Examiner* — Craig Ricci
*Assistant Examiner* — Jared D Barsky
(74) *Attorney, Agent, or Firm* — Patrick J. Hagan; Dann, Dorfman, Herrell and Skillman

(57) ABSTRACT

Compositions and methods for modulating HSP70 function, particularly for the targeted killing of cancer cells, are disclosed.

20 Claims, 54 Drawing Sheets

C

D

A

2-Phenylethynesulfonamide (PES)
($C_8H_7NO_2S$)

B

Human HSP70

MAKAAAIGID LGTTYSCVGV FQHGKVEIIA NDQGNRTTPS YVAFTDTERL
IGDAAKNQVA LNPQNTVFDA KRLIGRRFGD PVVQSDMKHW PFQVINDGDK
PKVQVSYKGE TKAFYPEEIS SMVLTKMKEI AEAYLGYPVT NAVITVPAYF
NDSQRQATKD AGVIAGLNVL RIINEPTAAA IAYGLDKTGK GERNVLIFDL
GGGTFDVSIL TIDDGIFEVK ATAGDTHLGG EDFDNRLVNH FVEEFKRKHK
KDISQNKRAV RRLRTACERA KRTLSSSTQA SLEIDSLFEG IDFYTSITRA
RFEELCSDLF RSTLEPVEKA LRDAKLDKAQ IHDLVLVGGS TRIPKVQKLL
QDFFNGRDLN KSINPDEAVA YGAAVQAAIL MGDKSENVQD LLLLDVTPLS
LGLETAGGVM TALIKRNSTI PTKQTQTFTT YSDNQPGVLI QVYEGERAMT
KDNNLLGRFE LSGIPPAPRG VPQIEVTFDI DANGILNVTA TDKSTGKANK
ITITNDKGRL SKEEIERMVQ EAEKYKAEDE VQRERVSAKN ALESYAFNMK
SAVEDEGLKG KISEADKKKV LDKCQEVISW LDANTLAEKD EFEHKRKELE
QVCNPIISKL YQAGGMPGGM PGGFPGGGAPPSGGASSGPTIEEVD

Human HSC70

MSKGPAVGID LGTTYSCVGV FQHGKVEIIA NDQGNRTTPS YVAFTDTERL
IGDAAKNQVA MNPTNTVFDA KRLIGRRFDD AVVQSDMKHW PFMVVNDAGR
PKVQVEYKGE TKSFYPEEVS SMVLTKMKEI AEAYLGKTVT NAVVTVPAYF
NDSQRQATKD AGTIAGLNVL RIINEPTAAA IAYGLDKKVG AERNVLIFDL
GGGTFDVSIL TIEDGIFEVK STAGDTHLGG EDFDNRMVNH FIAEFKRKHK
KDISENKRAV RRLRTACERA KRTLSSSTQA SIEIDSLYEG IDFYTSITRA
RFEELNADLF RGTLDPVEKA LRDAKLDKSQ IHDIVLVGGS TRIPKIQKLL
QDFFNGKELN KSINPDEAVA YGAAVQAAIL SGDKSENVQD LLLLDVTPLS
LGIETAGGVM TVLIKRNTTI PTKQTQTFTT YSDNQPGVLI QVYEGERAMT
KDNNLLGKFE LTGIPPAPRG VPQIEVTFDI DANGILNVSA VDKSTGKENK
ITITNDKGRL SKEDIERMVQ EAEKYKAEDE KQRDKVSSKN SLESYAFNMK
ATVEDEKLQG KINDEDKQKI LDKCNEIINW LDKNQTAEKE EFEHQQKELE
KVCNPIITKL YQSAGGMPGG MPGGFPGGGA PPSGGASSGP TIEVD

Figure 2

D            *E. coli.* (DH5α)

A

| Cell Lines | PES IC$_{50}$ |
|---|---|
| A549 | 0.56 μM |
| NCI-H460 | 0.71 μM |
| FR-E | 0.51 μM |
| NCI-H322 | 0.43 μM |
| REN | 0.41 μM |
| LRV | 0.36 μM |
| HT29 | 0.51 μM |
| HCT15 | 0.45 μM |
| SW620 | 0.37 μM |
| ACHN | 0.85 μM |
| SN12C | 0.66 μM |
| A2780 | 0.32 μM |
| A1847 | 0.52 μM |
| PEO1 | 0.41 μM |
| PEO4 | 0.49 μM |
| OVCAR4 | 0.26 μM |

| Cell Lines | PES IC$_{50}$ |
|---|---|
| OVCAR5 | 0.55 μM |
| OVCAR8 | 0.54 μM |
| OVCAR10 | 0.26 μM |
| UPN251 | 0.40 μM |
| OAW42 | 0.94 μM |
| IGROV1 | 0.40 μM |
| 2008 | 0.97 μM |
| U251 | 0.36 μM |
| SF-295 | 0.51 μM |
| SF-268 | 0.67 μM |
| SF-539 | 0.43 μM |
| SF-126 | 0.44 μM |
| SF-188 | 0.53 μM |
| SNB-75 | 0.53 μM |
| LN-229 | 0.71 μM |
| HepG2 | 0.51 μM |

| Cell Lines | PES IC$_{50}$ |
|---|---|
| MCF7 | 0.85 μM |
| BT549 | 0.36 μM |
| T47D | 0.39 μM |
| PC3 | 0.57 μM |
| DU-145 | 0.48 μM |
| J82 | 0.59 μM |
| JHU-012 | 0.57 μM |
| JHU-022 | 0.70 μM |
| LOXIMVI | 0.52 μM |
| M14 | 0.74 μM |
| UACC-62 | 0.36 μM |
| UO-31 | 0.47 μM |
| CAKI-1 | 0.33 μM |
| TE-8 | 0.77 μM |
| TE-10 | 0.53 μM |
| TE-11 | 0.24 μM | ns

SEQUENCE LISTING

```
<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: shRNA

<400> SEQUENCE: 1
acggcaaggt ggagatcatc gccaacgac                                        29

<210> SEQ ID NO 2
<211> LENGTH: 29
```

```
<212> TYPE: DNA
<213> ORGANISM: Artificial Sequence
<220> FEATURE:
<223> OTHER INFORMATION: shRNA

<400> SEQUENCE: 2
acgacggcat cttcgaggtg aaggccacg                                              29

<210> SEQ ID NO 3
<211> LENGTH: 29
<212> TYPE: DNA
<213> ORGANISM: Artificial Sequence
<220> FEATURE:
<223> OTHER INFORMATION: shRNA

<400> SEQUENCE: 3
ggccatgacg aaagacaaca atctgttgg                                              29

<210> SEQ ID NO 4
<211> LENGTH: 29
<212> TYPE: DNA
<213> ORGANISM: Artificial Sequence
<220> FEATURE:
<223> OTHER INFORMATION: shRNA

<400> SEQUENCE: 4
gccttcaaca tgaagagcgc cgtggagga                                              29

<210> SEQ ID NO 5
<211> LENGTH: 641
<212> TYPE: PRT
<213> ORGANISM: Homo Sapiens

<400> SEQUENCE: 5
```

Met Ala Lys Ala Ala Ala Ile Gly Ile Asp Leu Gly Thr Thr Tyr Ser
 1               5                  10                  15

Cys Val Gly Val Phe Gln His Gly Lys Val Glu Ile Ile Ala Asn Asp
             20                  25                  30

Gln Gly Asn Arg Thr Thr Pro Ser Tyr Val Ala Phe Thr Asp Thr Glu
         35                  40                  45

Arg Leu Ile Gly Asp Ala Ala Lys Asn Gln Val Ala Leu Asn Pro Gln
     50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

```
Ile Leu Thr Ile Asp Asp Gly Ile Phe Glu Val Lys Ala Thr Ala Gly
            210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly Asp Lys
370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
            450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Lys Tyr Lys Ala Glu
            515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
            595                 600                 605

Gly Leu Tyr Gln Gly Ala Gly Gly Pro Gly Pro Gly Gly Phe Gly Ala
610                 615                 620
```

```
Gln Gly Pro Lys Gly Gly Ser Gly Ser Gly Pro Thr Ile Glu Glu Val
625                 630                 635                 640

Asp

<210> SEQ ID NO 6
<211> LENGTH: 646
<212> TYPE: PRT
<213> ORGANISM: Homo Sapiens

<400> SEQUENCE: 6

Met Ser Lys Gly Pro Ala Val Gly Ile Asp Leu Gly Thr Thr Tyr Ser
  1               5                  10                  15

Cys Val Gly Val Phe Gln His Gly Lys Val Glu Ile Ile Ala Asn Asp
             20                  25                  30

Gln Gly Asn Arg Thr Thr Pro Ser Tyr Val Ala Phe Thr Asp Thr Glu
         35                  40                  45

Arg Leu Ile Gly Asp Ala Ala Lys Asn Gln Val Ala Met Asn Pro Thr
 50                  55                  60

Asn Thr Val Phe Asp Ala Lys Arg Leu Ile Gly Arg Arg Phe Asp Asp
 65                  70                  75                  80

Ala Val Val Gln Ser Asp Met Lys His Trp Pro Phe Met Val Val Asn
                 85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
            340                 345                 350
```

```
Phe Phe Asn Gly Lys Glu Leu Asn Lys Ser Ile Asn Pro Asp Glu Ala
            355                 360                 365

Val Ala Tyr Gly Ala Ala Val Gln Ala Ala Ile Leu Ser Gly Asp Lys
    370                 375                 380

Ser Glu Asn Val Gln Asp Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Lys Phe Glu Leu Thr Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
            500                 505                 510

Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
    530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
            580                 585                 590

Glu His Gln Gln Lys Glu Leu Glu Lys Val Cys Asn Pro Ile Ile Thr
        595                 600                 605

Lys Leu Tyr Gln Ser Ala Gly Gly Met Pro Gly Gly Met Pro Gly Gly
    610                 615                 620

Phe Pro Gly Gly Gly Ala Pro Pro Ser Gly Gly Ala Ser Ser Gly Pro
625                 630                 635                 640

Thr Ile Glu Glu Val Asp
                645

<210> SEQ ID NO 7
<211> LENGTH: 638
<212> TYPE: PRT
<213> ORGANISM: Escherichia coli

<400> SEQUENCE: 7

Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80
```

```
Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Glu Ile Asp
    195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
    370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Ala Asp Asn Lys Ser Leu Gly Gln Phe Asn Leu Asp Gly Ile Asn Pro
    450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495
```

-continued

```
Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
            515                 520                 525

Phe Glu Glu Leu Val Gln Thr Arg Asn Gln Gly Asp His Leu Leu His
            530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
            565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln Gln His Ala Gln
            595                 600                 605

Gln Gln Thr Ala Gly Ala Asp Ala Ser Ala Asn Asn Ala Lys Asp Asp
            610                 615                 620

Asp Val Val Asp Ala Glu Phe Glu Glu Val Lys Asp Lys Lys
625                 630                 635
```

MODULATORS OF HSP70/DNAK FUNCTION AND METHODS OF USE THEREOF

This application is a divisional of U.S. patent application Ser. No. 13/051,511, filed Mar. 18, 2011, which is a 35 U.S.C. §365(c) filing of PCT/US09/57430 filed Sep. 18, 2009 which in turn claims priority under 35 U.S.C. §119(e) to U.S. Provisional Application No. 61/098,476 filed Sep. 19, 2008, the entire disclosure of each is being incorporated herein by reference as though set forth in full.

Pursuant to 35 U.S.C. §202(c) it is acknowledged that the U.S. Government has certain rights in the invention described, which was made in part with funds from the National Institutes of Health, Grant Numbers CA118761 and DK078025.

FIELD OF THE INVENTION

The present invention relates to the fields of medicine, oncology and protein folding and transport. More specifically, the invention provides compositions and methods for modulating HSP70/HSC70/DnaK function. Such compositions and methods can be used alone or in combination to effectively induce cell death in targeted cells, in antimicrobial applications and in drug screening assays.

BACKGROUND OF THE INVENTION

Several publications and patent documents are cited throughout the specification in order to describe the state of the art to which this invention pertains. Each of these citations is incorporated by reference herein as though set forth in full.

Resistance to programmed cell death (apoptosis) is a characteristic of many cancer cells. Accordingly, efforts to develop new treatment strategies and therapeutic targets include attempts to identify and characterize proteins that regulate other survival or stress-response pathways. Heat shock proteins (HSPs) are encoded by evolutionarily conserved gene families and are required for cell survival following various forms of stress. HSPs are generally classified according to their approximate molecular size, and are structurally and functionally diverse; some are constitutively expressed, while others are stress-induced (Mayer and Bukau, 2005; Brodsky and Chiosis, 2006; Garrido et al., 2006; Schmitt et al., 2006; Powers and Workman, 2007). The stress-inducible protein HSP70 (also called HSP72, HSP70-1 or HSPA1A) is an approximately 70 kDa ATP-dependent molecular chaperone that is present at low or undetectable levels in most unstressed normal cells and tissues. Its abundance rapidly increases in response to a variety of metabolic or exogenous insults that, among other effects, can cause changes in protein conformation or stability. HSP70-inducing stresses include elevated temperatures, nutrient deprivation, heavy metals, oxidative stress and viral infections. The stress-inducible HSP70 is thought to help cells cope with these potentially deleterious conditions, in part by aiding with folding of nascent polypeptides or refolding of damaged proteins, preventing/reversing protein aggregation or self-association, promoting protein transport to intracellular locations for degradation, and aiding in the formation of protein complexes. HSP70 also is an important regulator of apoptotic signaling pathways, acting in part through direct interactions with substrate proteins that affect multiple steps in the process, including control of mitochondrial membrane integrity and caspase-activation (Mayer and Bukau, 2005; Brodsky and Chiosis, 2006; Garrido et al., 2006; Schmitt et al., 2006; Powers and Workman, 2007).

In contrast to its low abundance in unstressed normal cells, the inducible HSP70 protein is present at constitutively elevated levels in many human tumors of various origin. Such enhanced HSP70 expression correlates with resistance of the tumor cells to caspase-dependent and -independent cell death and is associated with poor patient prognosis (Brodsky and Chiosis, 2006; Garrido et al., 2006; Guzhova and Margulis, 2006; Schmitt et al., 2006). It is likely that the unfavorable conditions associated with the tumor microenvironment, such as hypoxia, nutrient deprivation, oxidative stress, oncogene activation, and exposure to chemotherapeutics lead to alterations in protein structure or processing, as well as upregulation of HSP70. The actions of this protein would be expected to help tumor cells tolerate, or adapt to, these conditions, and current evidence suggests that elevated HSP70 expression promotes tumorigenesis. Conversely, reducing HSP70 levels in some cultured tumor cells has been reported to induce cell death, and/or to sensitize them to cytotoxic agents, while having no obvious deleterious effects on non-tumor cells (Nylandsted et al., 2000, 2002; Rohde et al., 2005; Schmitt et al., 2006; Aghdassi et al., 2007; Powers et al., 2008).

In addition to its cytoprotective actions in promoting tumorigenesis, an altered expression or function of HSP70 also has been implicated in certain other human disorders that are associated with defects in protein conformation or folding. This includes disorders caused by the presence of mutant proteins, as well as some neurodegenerative diseases such as Alzheimer's and Parkinson's disease, and viral pathogenesis (McClellan et al., 2005; Muchowski and Wacker, 2005; Brodsky and Chiosis, 2006; Guzhova and Margulis, 2006; Morimoto, 2008). The identification of small molecules that specifically interact with, and modulate the activities of, HSP70 therefore has important implications for a number of human diseases. To date, however, only a limited number of compounds that specifically target HSP70 have been identified in chemical screens, and few are currently available to assess the physiologic impact of modulating HSP70 actions (Brodsky and Chiosis, 2006; Powers and Workman, 2007; Wisén and Gestwicki, 2008).

SUMMARY OF THE INVENTION

Here we report that the small molecule 2-Phenylethynesulfonamide (PES), also called phenylacetylenylsulfonamide, or pifithrin-μ (PFTμ), and analogs thereof, interact selectively with the stress-inducible HSP70 protein, as well as the closely related HSC70 molecular chaperone, inhibiting their functions. Tumor cell lines treated with PES lose viability associated with evidence of protein aggregation and dysregulation of autophagic/lysosomal/proteasomal processes. Moreover, administration of PES inhibits Myc-induced lymphoma in a mouse model system.

Thus, in accordance with one aspect of the present invention, there is provided a method for potentiating the effect of at least one chemotherapeutic agent in the treatment of disease associated with heat shock protein (HSP) 70 activity. An exemplary method entails co-administration of a compound of the formula:

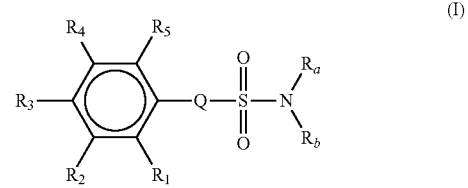

and pharmaceutically acceptable salts, wherein, $R_1$, $R_2$, $R_3$, $R_4$ and $R_5$ are the same or different and represent a radical selected from the group of hydrogen, optionally substituted alkyl, hydroxyl, alkoxy, thio, alkylthio, halogen, amino, monoalkylamino, dialkylamino, amido, nitro, carboxyl, alkoxycarbonyl, alkylcarbonyl, alkylcarbonyloxy, guanidino, phosphate, sulfamido and sulfonamido; Q represents a divalent linking moiety selected from the group consisting of —C($R_6R_7$)—C($R_8R_9$)—, —$CR_{10}$═$CR_{11}$—, and —C≡C—, wherein $R_6$, $R_7$, $R_8$, $R_9$, $R_{10}$, and $R_{11}$ represent a radical selected from the group consisting of hydrogen and optionally substituted alkyl; $R_a$ and $R_b$ are the same or different and represent hydrogen, optionally substituted alkyl, optionally substituted aryl, optionally substituted aralkyl, hydroxyl, alkoxy, amino, monoalkylamino, dialkylamino, carboxy, alkylcarbonyl, and alkyloxycarbonyl; or, optionally, $R_1$, $R_2$, $R_3$, $R_4$, $R_5$, $R_a$, and $R_b$ are independently substituted with one member of a specific binding pair or a targeting ligand to facilitate targeting of the compound to a target tissue of interest, the compound being co-administered with a chemotherapeutic agent of interest and being effective to inhibit protein function, wherein said protein function is selected from the group consisting of HSP70, HSC70, and DnaK. HSP functions which are modulated using the methods of the invention, include without limitation, modulation of protein aggregation, chaperone protein binding, client protein binding, modulation of cellular stress response, modulation of autophagy, modulation of caspase cleavage, reduced viability and modulation of vacuolization. In preferred embodiments, the compound of formula I is pifithrin-μ (PES) and the disease is characterized by aberrant cell proliferation.

The method of the invention may optionally further entail co-administration of an HSP 90 inhibitor and/or subjecting the patient to be treated to a heat treatment sufficient to induce a heat shock response. Methods of inhibiting HSP70 function via administration of a compound of formula I also comprise an aspect of the invention. In yet another aspect, a method for reducing bacterial load in a sample is disclosed. An exemplary method entails contacting said sample with a compound of the formula

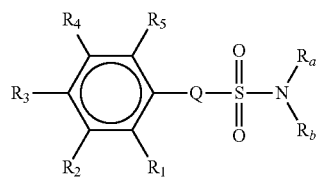

(I)

and pharmaceutically acceptable salts, wherein, $R_1$, $R_2$, $R_3$, $R_4$ and $R_5$ are the same or different and represent a radical selected from the group of hydrogen, optionally substituted alkyl, hydroxyl, alkoxy, thio, alkylthio, halogen, amino, monoalkylamino, dialkylamino, amido, nitro, carboxyl, alkoxycarbonyl, alkylcarbonyl, alkylcarbonyloxy, guanidino, phosphate, sulfamido and sulfonamido; Q represents a divalent linking moiety selected from the group consisting of —C($R_6R_7$)—C($R_8R_9$)—, —$CR_{10}$═$CR_{11}$—, and —C≡C—, wherein $R_6$, $R_7$, $R_8$, $R_9$, $R_{10}$, and $R_{11}$ represent a radical selected from the group consisting of hydrogen and optionally substituted alkyl; $R_a$ and $R_b$ are the same or different and represent hydrogen, optionally substituted alkyl, optionally substituted aryl, optionally substituted aralkyl, hydroxyl, alkoxy, amino, monoalkylamino, dialkylamino, carboxy, alkylcarbonyl, and alkyloxycarbonyl, said alkyl substituent being at least one selected from the group consisting of hydroxyl, thio, alkoxy, alkylthio, halogen, amino, monoalkylamino, dialkylamino, guanidino, phosphate, amido, nitro, carboxyl, sulfamido, sulfonamido, alkoxycarbonyl, alkylcarbonyl, and alkylcarbonyloxy; or, optionally, $R_1$, $R_2$, $R_3$, $R_4$, $R_5$, $R_a$, and $R_b$ are independently substituted with one member of a specific binding pair or a targeting ligand, subjecting the sample to heating sufficient to induce a heat shock response, the combination of heat and compound administration being effective to inhibit DnaK activity in said bacteria. The method may further entail administration of an antimicrobial selected from the group consisting of gentamycin, kanamycin, neomycin, streptomycin, cefazolin, vancomycin, azithromycin, cephalosporin, clarithromycin, erythromycin, spectinomycin, penicillin, amoxicillin, bacitran, and tetracycline.

In practicing the method aspect of the invention, the compound of Formula I may be used in combination with radiation therapy. The radiation therapy can be any form of radiation therapy used in the art such as for example, external beam radiation such as x-ray treatment, radiation delivered by insertion of radioactive materials within the body near or at the tumor site such as treatment with gamma ray emitting radionuclides, particle beam therapy which utilizes neutrons or charged particles and the like. In addition, this embodiment encompasses the use of the compound of Formula I in a cocktail of other chemotherapeutic agents or biological agents (such as antibody mediated therapy) and/or in combination with radiation therapy.

In another aspect of the present invention, there is provided a compound of the formula:

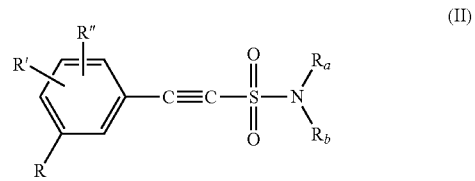

(II)

and pharmaceutically acceptable salts thereof, wherein R represents a substituent selected from the group consisting of chloro, fluoro, alkyl ($C_1$-$C_4$), trifluoromethyl, amino, carboxy, hydroxyl and methoxy; and R' and R" are the same or different and represent a radical selected from the group of hydrogen, optionally substituted alkyl ($C_1$-$C_6$), hydroxyl, alkoxy, thio, alkylthio, halogen, amino, monoalkylamino, dialkylamino, amido, nitro, carboxy, alkoxycarbonyl, alkylcarbonyl and alkylcarbonyloxy; $R_a$ and $R_b$ are the same or different and represent a radical selected from the group of hydrogen, hydroxyl, alkoxy, amino, monoalkylamino, dialkylamino, carboxy, alkoxycarbonyl, alkylcarbonyl and optionally substituted alkyl ($C_1$-$C_6$), said alkyl substituent being at least one selected from the group consisting of hydroxyl, thio, alkoxy, alkylthio, halogen, amino, monoalkylamino, dialkylamino, guanidino, phosphate, amido, nitro, carboxyl, sulfamido, sulfonamido, alkoxycarbonyl, alkylcarbonyl, and alkylcarbonyloxy.

In yet another aspect of the invention, there is provided a compound provided of the formula:

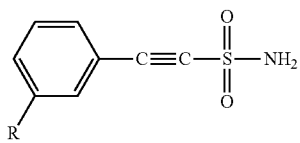

and pharmaceutically acceptable salts thereof, wherein R represents a radical selected from the group of chloro, fluoro, amino, carboxy, hydroxy and methoxy. In a particularly preferred embodiment the compound is 2-(3-chlorophenyl)-ethynesulfonamide (PES-Cl).

In yet another aspect of the invention, a compound is provided of the formula:

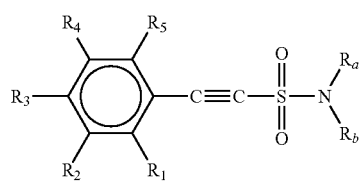

and pharmaceutically acceptable salts thereof, wherein one of $R_1$-$R_5$ represents halogen and the others represent hydrogen; $R_a$ and $R_b$ are the same or different and each represents a radical selected from the group of hydrogen and optionally substituted alkyl ($C_1$-$C_6$), and wherein said halogen is selected from the group consisting of chlorine, bromine, iodine and fluorine.

FIG. 20. PES and cisplatin act synergistically to kill cancer cells. (A) SRB assay of FADU cells treated with PES (0-100 μM), cisplatin (0-100 μM) and PES plus cisplatin (0-100 μM, 1:1 ratio) for 72 h. Experiments were done in triplicate per condition. (B) Isobologram demonstrates synergism of PES with cisplatin in FADU cells (CompuSyn program).

Figure 21:
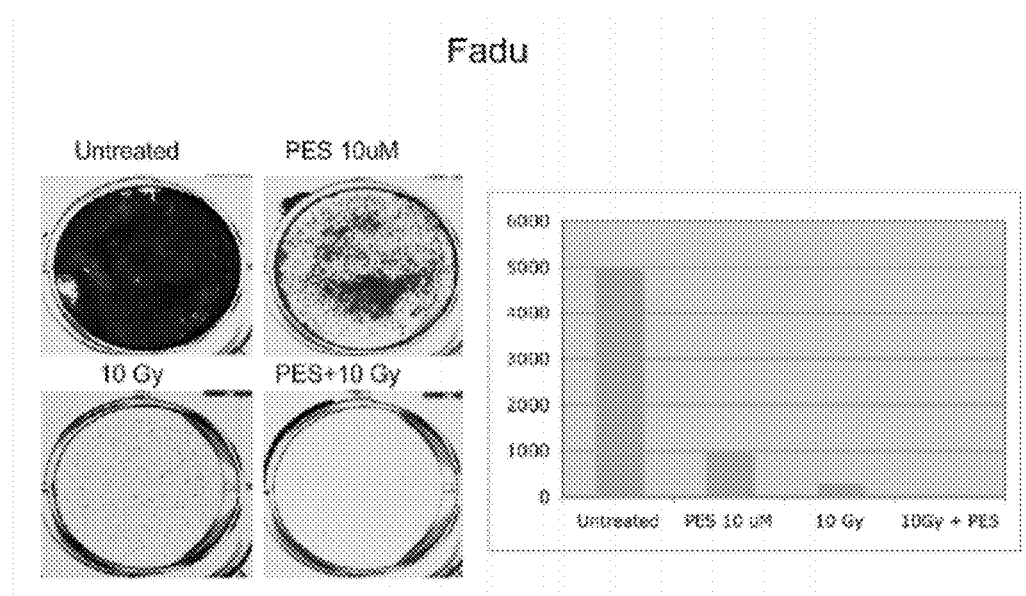

FIG. 21. PES and radiation cooperatively kill cancer cells. Colony formation assay of FADU cells treated with PES (10 μM), gamma irradiated (10 Gy) or both (PES 10 μM+10 Gy).

Figure 22:
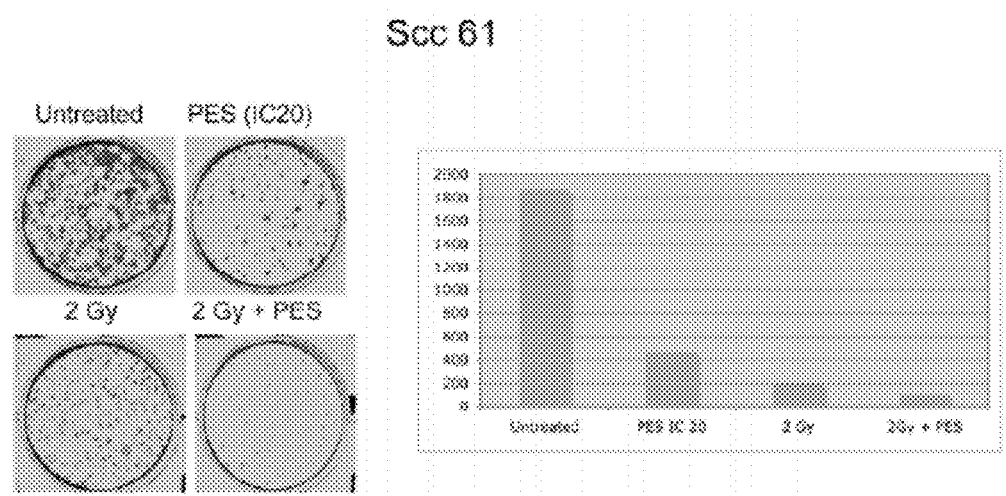

FIG. 22. PES and radiation induced cell death is not cell type specific. Colony formation assay of Scc61 cells treated with PES (IC$_{20}$), gamma irradiated (2 Gy) or both (PES IC$_{20}$, 2 Gy).

Figure 23:
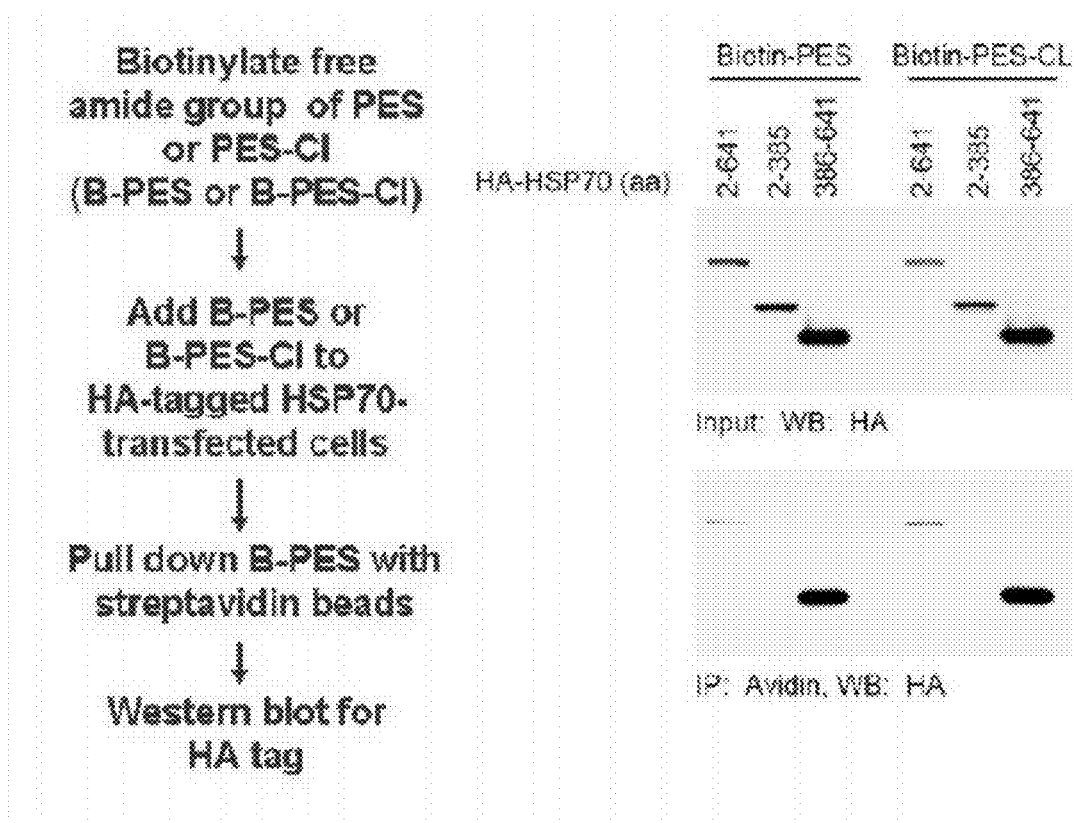

FIG. 23. PES-Cl directly interacts with HSP70. A) Flow chart of the experimental design. B) H1299 cells were transfected with the indicated HA-tagged constructs and treated with B-PES or B-PES-Cl for 6 hours. The B-PES and B-PES-Cl complexes were captured with NeutrAvidin resins, eluted with 100 mM DTT treatments, separated with SDS-PAGE and detected with anti-HA antibody (Millipore).

Figure 24:
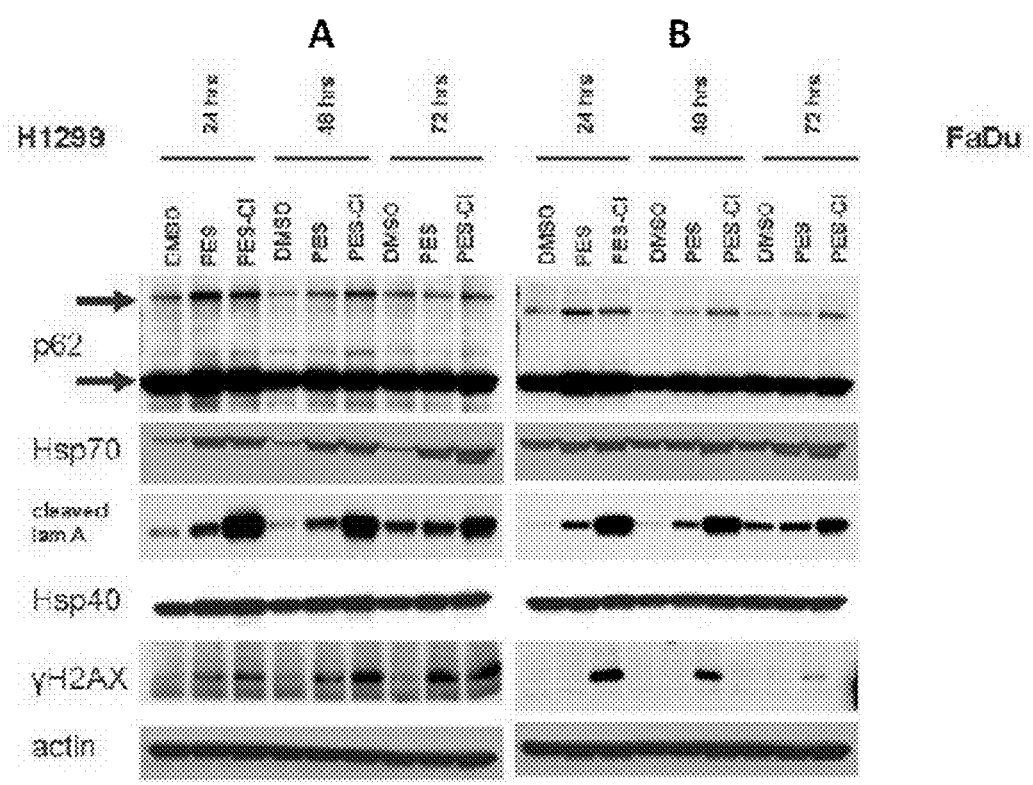

FIG. 24. PES-Cl inhibits autophagy and induces apoptosis in H1299 and FaDu cells. H1299 and FaDu cells were seeded in 10 cm plates and treated with 10 μM PES and 10 μM PES-Cl. DMSO treated cells were used as vehicle treated control. Twenty-four, 48 and 72 hours post treatment the cells were scrapped and proteins extracts were generated. Western blotting was performed as per standard protocols. Antibodies used: p62 (Santa Cruz), Hsp70 (Cell Signaling), cleaved lamin A (Cell Signaling), Hsp40 (Cell Signaling), γH2A.X (Millipore) and actin (Sigma).

Figure 25A:
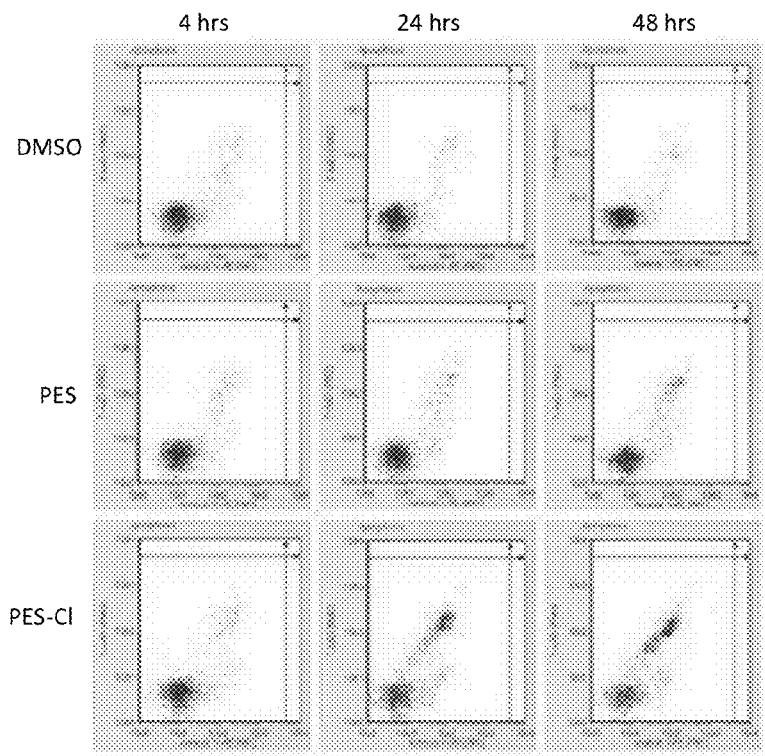
Figure 25B:
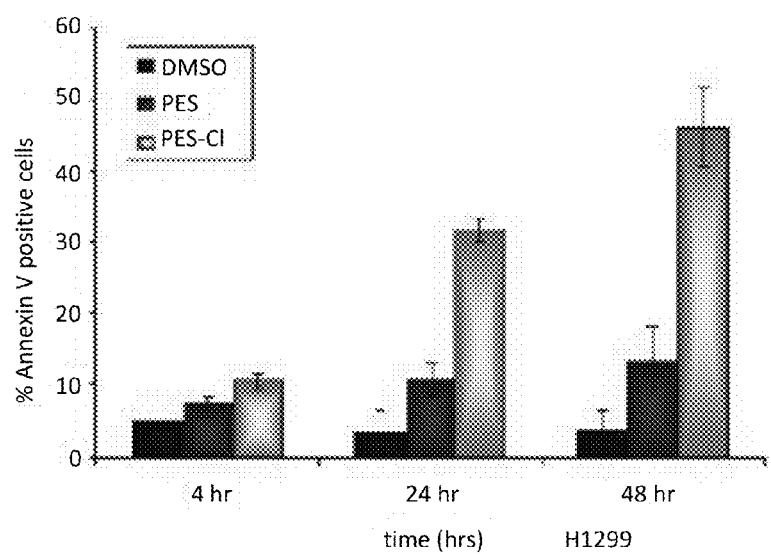

FIG. 25. PES-Cl is a superior compound for induction of apoptosis in H1299 cells. A) H1299 cells were seeded on a 24 well plate and treated with 10 μM PES or 10 μM PES-Cl. DMSO treated cells were used as a vehicle control. Four, 24 and 48 hours post treatment the cells were washed with PBS and trypsinized. The cells were pelleted and resuspended in Guava Nexin reagent (Millipore) as per manufacturer's instructions. Readings were obtained with a Guava reader (Guava Technologies, Millipore). Representative images of density plots are shown. B) Graphical representation of the data from A) representing the total number of Annexin V positive cells.

Figure 26A:
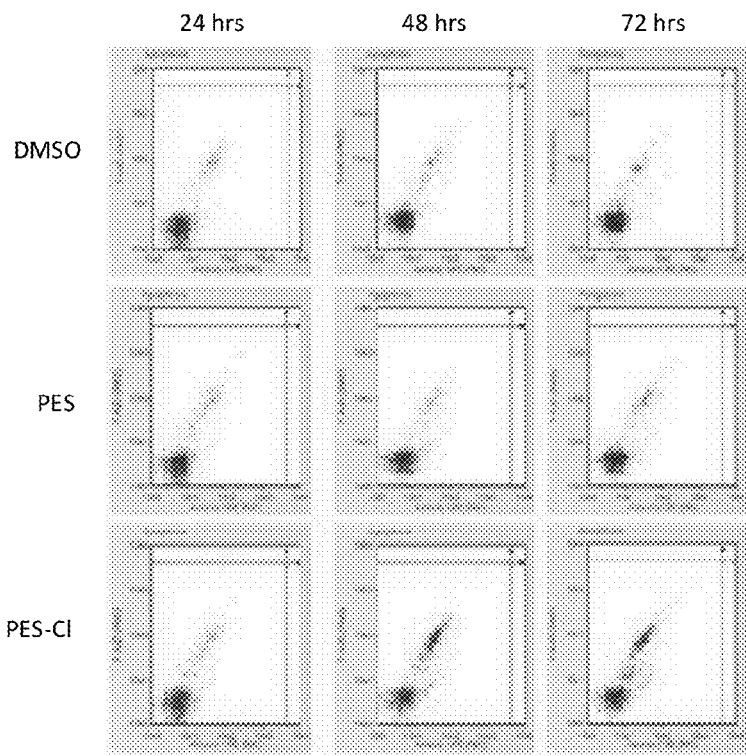
Figure 26B:
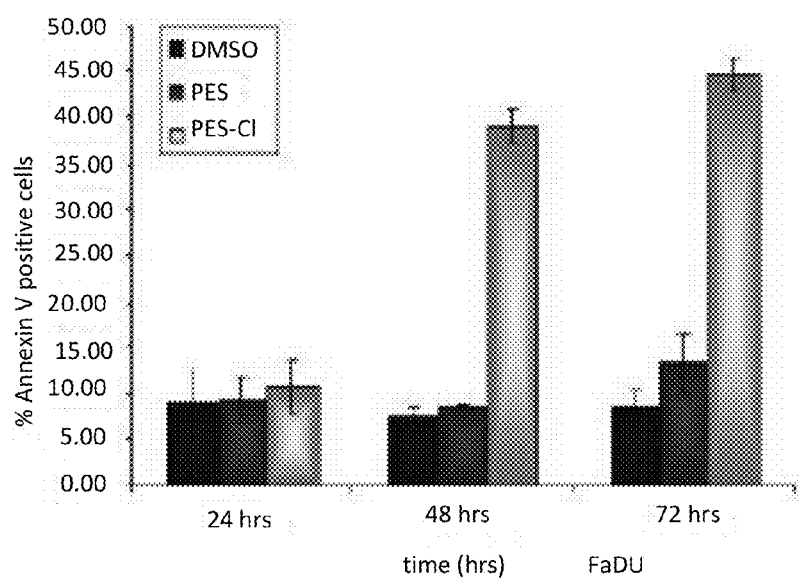

FIG. 26. PES-Cl is a superior compound for induction of apoptosis in FaDu cells. A) FaDu cells were seeded on a 24 well plate and treated with 10 μM PES or 10 μM PES-Cl. DMSO treated cells were used as a vehicle control. Twenty four, 48 and 72 hours post treatment the cells were washed with PBS and trypsinized. The cells were pelleted and resuspended in Guava Nexin reagent (Millipore) as per manufacturer's instructions. Readings were obtained with a Guava reader (Guava Technologies, Millipore). Representative images of density plots are shown. B) Graphical representation of the data from A) representing the total number of Annexin V positive cells.

Figure 27:
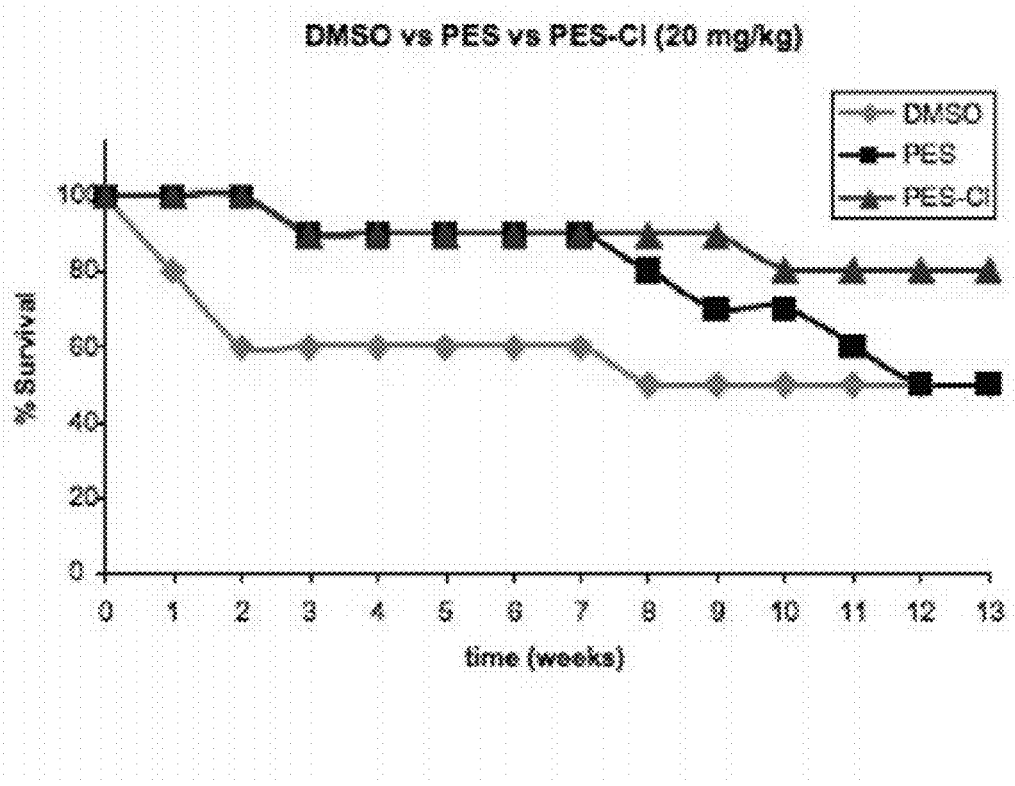

FIG. 27. PES-Cl prevents Myc-induced B-cell lymphogenesis and extends the survival of Eμ-myc transgenic mice. Eμ-myc transgenic mice (6 weeks of age) were treated either with vehicle, 20 mg/kg PES or 20 mk/kg PES-Cl with continuous weekly i.p. injections.

Figure 28:
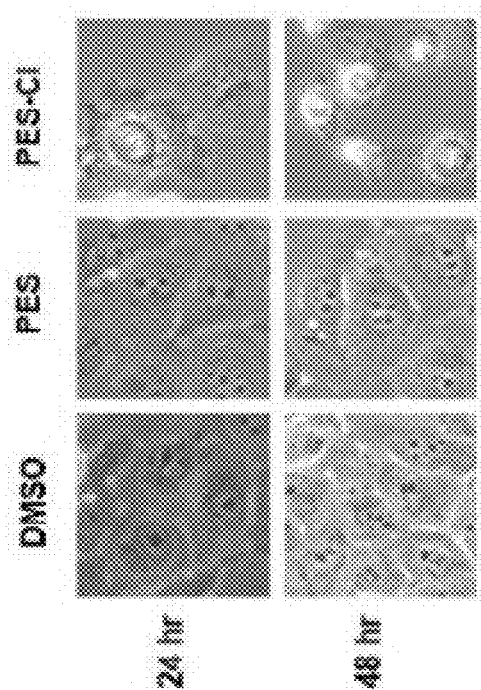
Figure 28:
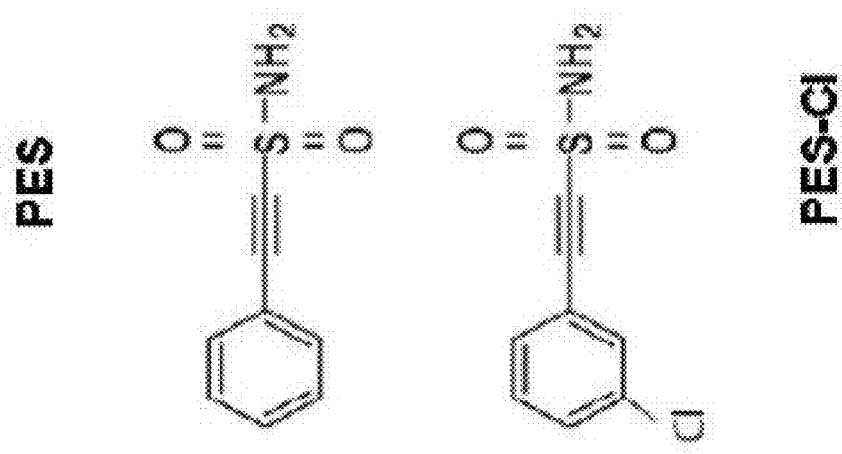

FIG. 28. PES-Cl inhibits the proliferation of H1299 cells. A) Chemical structure of PES and PES-Cl. B) H1299 cells were seeded on 100 mm plates and treated with 10 μM PES or 10 μM PES-Cl. DMSO treated cells were used as vehicle treated controls. Cells were observed 24 and 48 hours post treatment under light microscopy with 20× magnification.

Figure 29:
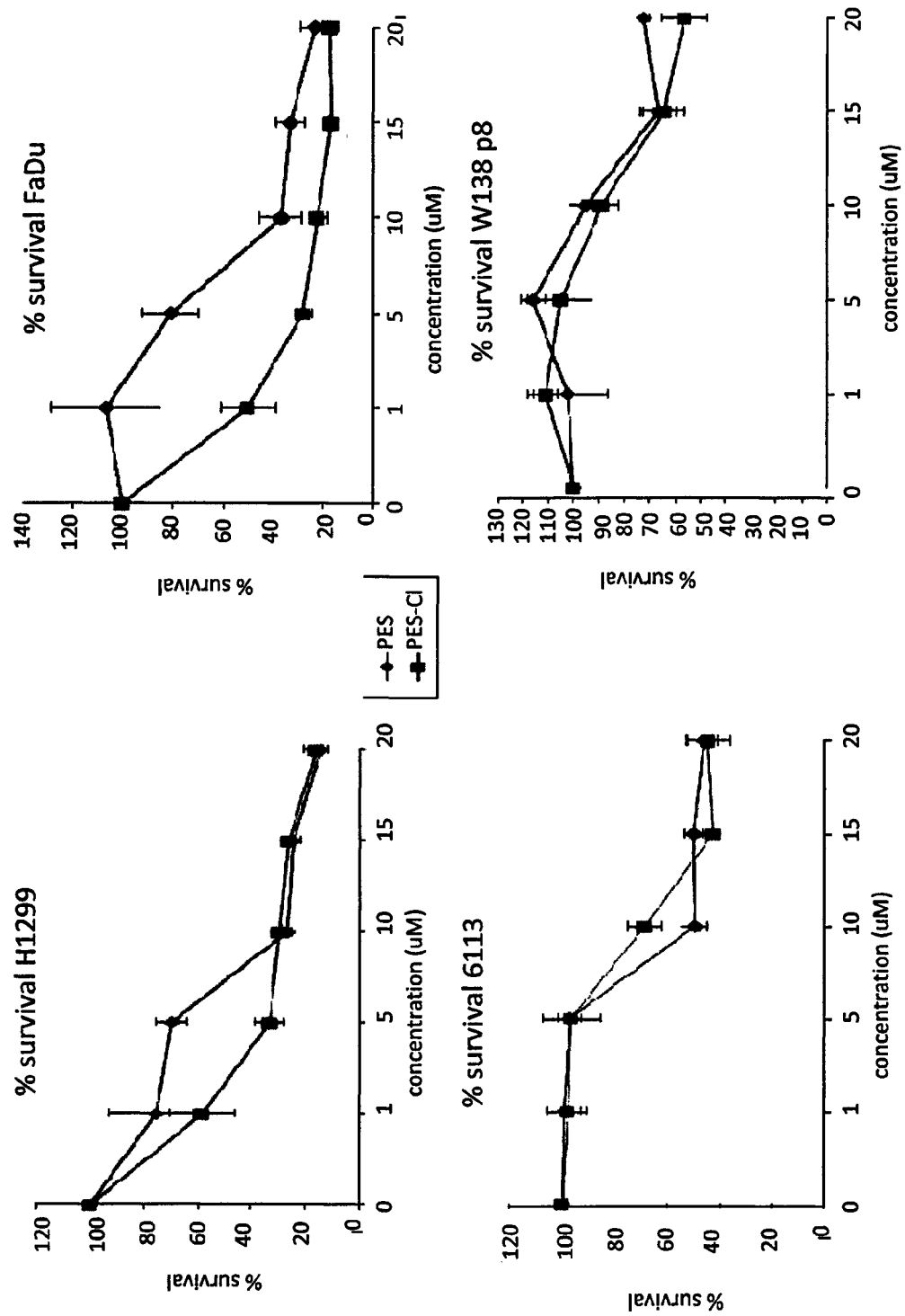

FIG. 29. PES-Cl is a superior and specific inhibitor of proliferation of tumor cells with limited toxicity to normal cells. Two tumor cell lines (H1299 and FaDu) and two normal fibroblast cell lines (6113 and WI38) were seeded in 96-well plate. The cells were treated with various concentrations of PES and PES-Cl. Forty-eight hours post treatment MTT assays (Cayman Chemical Company) were performed as per manufacturer's protocol.

Figure 30:
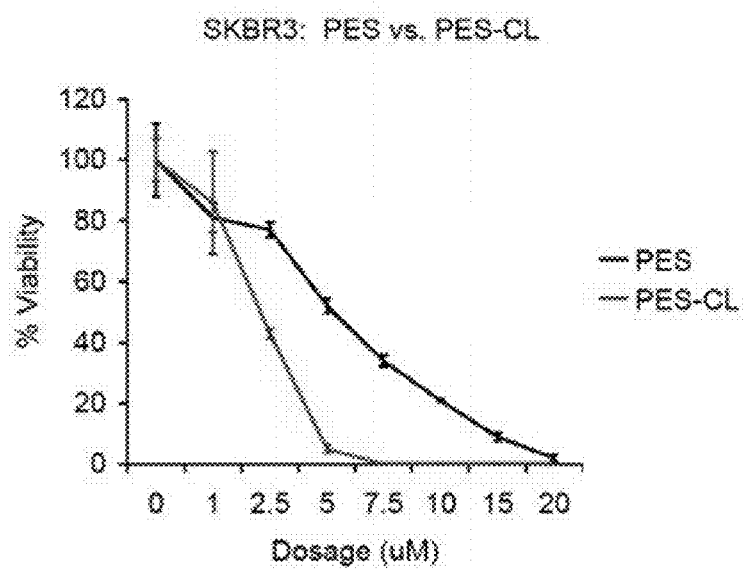

FIG. 30. PES-Cl is a superior inhibitor of SKBR3 human breast adenocarcinoma cells. PES-Cl is a superior inhibitor of proliferation of tumor cells when compared to PES. SKBR3 cells were seeded. The cells were treated with various concentrations of PES and PES-Cl. Seventy-two hours post treatment MTT assays (Cayman Chemical Company) were performed as per manufacturer's protocol.

Figure 31:
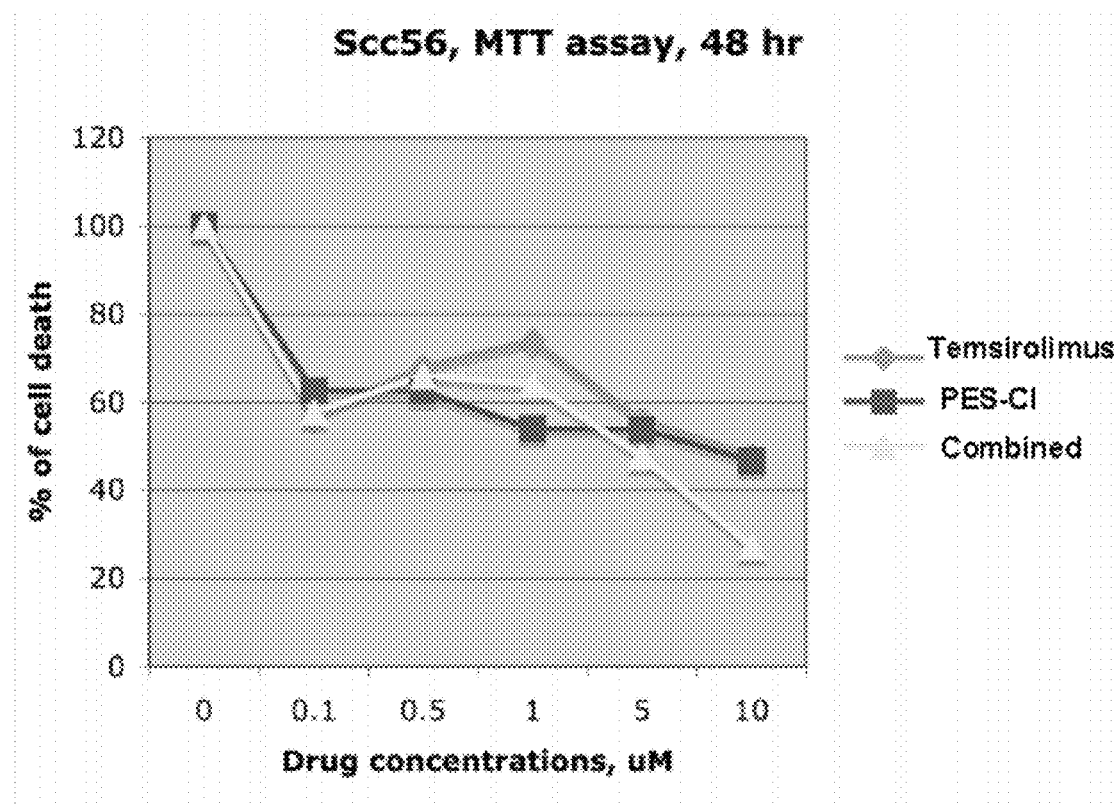

FIG. 31. PES-Cl and Temsirolimus act synergistically to kill cells. An MTT cell viability assay was performed in which Scc56 cells were treated with PES-Cl and Temsirolimus, singly and together, to assess synergistic activity.

Figure 32:
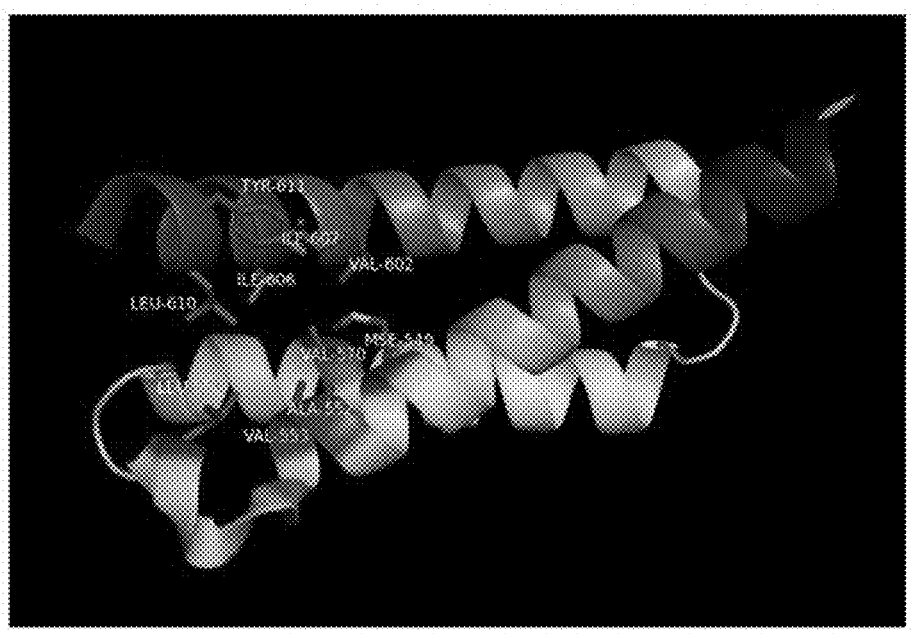

FIG. 32. A model of the crystal structure of the C terminus of HSP70. A molecular model of C terminal HSP70 is demonstrated with amino acids proximal to the PES active site highlighted.

Figure 33:
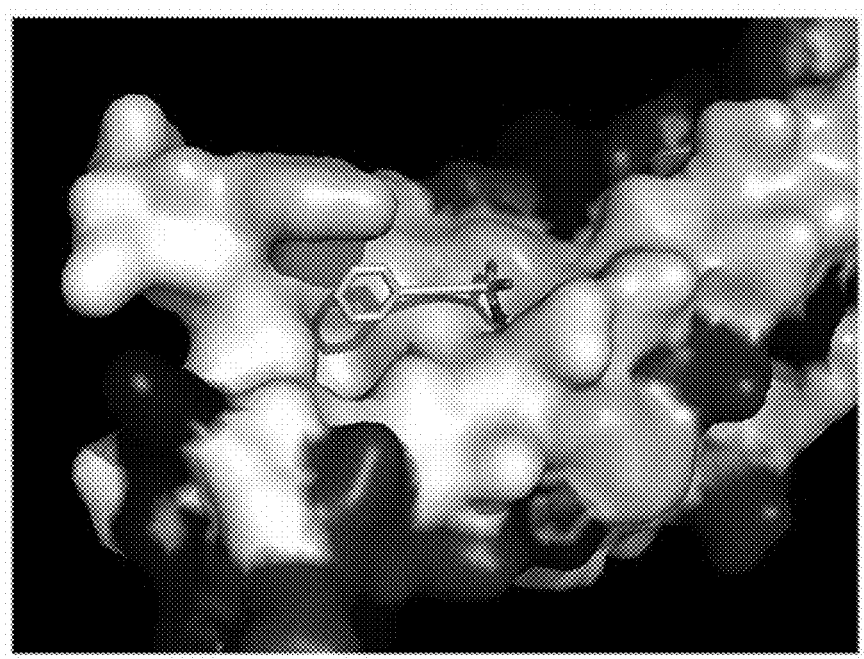

FIG. 33. In Silico docking of PES bound to the pocket created by the C terminal helices of HSP70. A graphical image of the PES binding site and the posture of PES bound therein. Blind docking methods were used in the program AutoDock to locate potential PES binding sites. These methods use a course grid docking approach, encompassing the entire protein, to identify favorable binding sites using a known binding ligand, and are examined by hand to support the AutoDock data.

Figure 34:
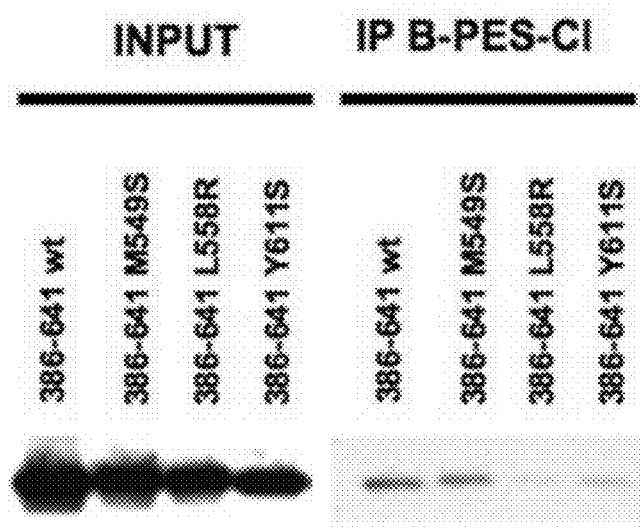

FIG. 34. The L558R and Y611S mutants of C terminal helices of HSP70 fail to bind PES. Mutants were predicted based upon molecular modeling studies to disrupt the PES ligand-protein interaction. Mutants were generated in HA-tagged HSP70 by site-directed mutagenesis, and transfected into cells. These mutants were used in binding assays with biotinylated PES as per Leu et al. (Mol. Cell. 2009).

DETAILED DESCRIPTION OF THE INVENTION

The multifunctional, stress-inducible, molecular chaperone HSP70 has important roles in aiding protein folding and maintaining protein homeostasis. HSP70 expression is elevated in many cancers, contributing to tumor cell survival and resistance to therapy. We have determined that a small molecule called 2-Phenylethynesulfonamide (PES) interacts selectively with HSP70, and leads to a disruption of the association between HSP70 and several of its co-chaperones and substrate proteins. Treatment of cultured tumor cells with PES promotes cell death that is associated with protein aggregation, impaired autophagy, and inhibition of lysosomal function. Moreover, this small molecule is able to suppress tumor development and enhance survival in a mouse model of Myc-induced lymphomagenesis. The data demonstrate that PES disrupts actions of HSP70 in multiple cell signaling pathways offering an opportunity to better understand the diverse functions of this molecular chaperone, and also to aid in the development of new cancer therapies.

The present invention arose out of research which demonstrated that the small molecule 2-Phenylethynesulfonamide [referred to interchangeably herein as PES, Phenylacetylenylsulfonamide or pifithrin-μ (PFTμ)] interacts selectively with HSP70, reducing interactions between HSP70 and its co-chaperones as well as client proteins. PES treatment of tumor cells results in cytoplasmic vacuolization, protein aggregation, detachment from substrate, and induction of autophagy. Also, tumor cells are more sensitive than normal cells to the cytotoxic effects of PES, and co-treatment of tumor cells with PES augments and/or potentiates the cytotoxic effects of other chemotherapeutics. Based on these novel findings, the use of PES, individually and in combination with other agents provides an efficacious approach for the treatment of disorders associated with altered HSP70 function, including cancer and other disorders. The invention provides biologically active derivatives as well as novel therapeutic protocols that target HSP70 function in multiple cell signaling pathways critical for tumor cell survival.

In carrying out the methods of the invention involving modulating HSP70 function for the treatment of proliferative disorders such as cancer, compounds of formula I,

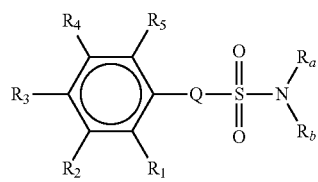

and pharmaceutically acceptable salts thereof may be employed, wherein, $R_1$, $R_2$, $R_3$, $R_4$ and $R_5$ are the same or different and represent a radical selected from the group of hydrogen, optionally substituted alkyl, hydroxyl, alkoxy, thio, alkylthio, halogen, amino, monoalkylamino, dialkylamino, amido, nitro, carboxyl, alkoxycarbonyl, alkylcarbonyl, alkylcarbonyloxy, guanidino, phosphate, sulfamido and sulfonamido; Q represents a divalent linking moiety selected from the group consisting of —C($R_6R_7$)—C($R_8R_9$)—, —$CR_{10}$=$CR_{11}$—, and —C≡C—, wherein $R_6$, $R_7$, $R_8$, $R_9$, $R_{10}$, and $R_{11}$ represent a radical selected from the group consisting of hydrogen and optionally substituted alkyl; $R_a$ and $R_b$ are the same or different and represent hydrogen, optionally substituted alkyl, optionally substituted aryl, optionally substituted aralkyl, hydroxyl, alkoxy, amino, monoalkylamino, dialkylamino, carboxy, alkylcarbonyl, and alkyloxycarbonyl, said alkyl substituent being at least one selected from the group consisting of hydroxyl, thio, alkoxy, alkylthio, halogen, amino, monoalkylamino, dialkylamino, guanidino, phosphate, amido, nitro, carboxyl, sulfamido, sulfonamido, alkoxycarbonyl, alkylcarbonyl, and alkylcarbonyloxy; or, optionally, $R_1$, $R_2$, $R_3$, $R_4$, $R_5$, $R_a$, and $R_b$ are independently substituted with one member of a specific binding pair or a targeting ligand to facilitate targeting of the compound to the target tissue of interest, the compound optionally being administered with a chemotherapeutic agent of interest in an amount effective to inhibit heat shock protein (HSP) 70, heat shock cognate (HSC) 70, or DnaK function.

The compound of Formula I above, in which $R_1$-$R_5$ and $R_a$ and $R_b$ represent hydrogen, commonly known as pifithrin-mu ($C_8H_7NO_2S$) or 2-Phenylethynesulfonamide, is commercially available from Sigma-Aldrich and from EMD Chemicals, Inc. Substituted forms of this basic structure may be prepared according to the synthetic schemes shown in U.S. Pat. No. 7,250,444 or in the manner described in K. Hasegawa et al., Bull. Chem. Soc. Japan 50:2346-50 (1977).

As used herein, the phrase "HSP70 function or activity" refers to one or more of several diverse biochemical functions, including: nascent protein folding; refolding of misfolded proteins; reducing/preventing denatured/misfolded protein aggregation; modulating assembly/disassembly of protein complexes; targeting proteins for proper intracellular location; targeting altered proteins for degradation by proteasomes, lysosomes or in pathways of autophagy; modulating cell death pathways, chaperone protein binding, client protein binding, modulation of cellular stress response, and modulation of caspase cleavage pathways.

The term "alkyl" as used herein refers to straight or branched chain aliphatic hydrocarbon radicals of up to 10 carbon atoms, preferably up to 6 carbon atoms and more preferably 1 to 4 carbon atoms. Similarly, the term "alkyl" or any variation thereof, used in combination form to name substituents, such as alkoxy (—O-alkyl), cycloalkylalkyl (-alkyl-cycloalkyl), arylalkyl (-alkyl-aryl), hydroxyalkyl (-alkyl-OH), monoalkylamino (—NH-alkyl), aminoalkyl (-alkyl-$NH_2$), alkylthio (—S-alkyl), alkylsulfinyl (—S(=O)-alkyl), alkylsulfonyl (—S(O)$_2$-alkyl), alkylsulfonic acid (—O—S(O)$_2$-alkyl), or the like also refers to straight or branched chain aliphatic hydrocarbon radicals of up to 10 carbon atoms, preferably 1 to 6 carbon atoms, and more preferably of 1 to 4 carbon atoms.

As used herein, the term "aryl", when used as such, or in combination form, for example "aralkyl," refers to an aromatic carbocyclic group, having 6 to 10 carbon atoms including, without limitation, phenyl and napthyl.

The term "polyfluoroalkyl," as used herein, refers to an alkyl radical or substituent having one or more fluoro substituents and includes perfluoroalkyl groups. Examples include trifluoromethyl and trifluoroethyl. The term "polyfluoroalkoxy," as used herein, refers to an alkoxy radical or substituent having one or more fluoro substituents and includes perfluoroalkoxy groups. Examples include trifluoromethoxy and trifluoroethoxy.

The term "amino", as used herein refers to the —$NH_2$ radical.

The term "amido," as used herein, refers to a radical or substituent of the formula —NR"C(=O)R''', wherein R" and R''' independently represent hydrogen, alkyl, or cycloalkyl. Similarly, the term "amidoalkyl," as used herein, refers to a radical or substituent of the formula -alkyl-NR"C(=O)R''', wherein R" and R''' are as previously defined.

A substituted monoalkylamino, as used herein, refers to a radical or substituent of the formula —NH-alkyl in which the alkyl group is further substituted with the indicated substituents.

The term "carboxyl," as used herein, refers to a radical or substituent of the formula —C(=O)OH.

The term "alkylcarbonyl," as used herein, refers to a radical or substituent of the formula —C(=O)-alkyl, and includes, for example, methylcarbonyl, ethylcarbonyl, propylcarbonyl, butylcarbonyl, and pentylcarbonyl.

The term "alkoxycarbonyl," as used herein, refers to a radical or substituent —C(=O)—O-alkyl, and includes, for example, methoxycarbonyl, ethoxycarbonyl, propoxycarbonyl, butoxycarbonyl, and pentoxycarbonyl.

The term "alkylcarbonyloxy" as used herein refers to a radical or substituent of the formula —O—C(=O)-alkyl, and includes for example methylcarbonyloxy, ethylcarbonyloxy, propylcarbonyloxy and the like.

The term "thio," as used herein, refers to a radical or substituent of the formula —SH.

The term "halogen," as used herein, refers to a radical or substituent selected from the group consisting of chloro, bromo, iodo, and fluoro.

The term "haloalkyl," as used herein, refers to an alkyl group as defined above that is further substituted with a halogen, as defined above.

The term "nitro" as used herein, refers to the —NO$_2$ radical.

The term "guanidino," as used herein, refers to a substituted or unsubstituted amino urea radical of the structure —NH—C(=NH)—NH$_2$.

The term "sulfamido," as used herein, refers to a substituted or unsubstituted —NH—SO$_2$—NH$_2$ radical.

The term "sulfonamido," as used herein, refers to a substituted or unsubstituted
—S(=O$_2$)—NH$_2$ radical.

The term "phosphate," as used herein, refers to —O—P(=O)(OH)$_2$, and salts thereof, and includes organophosphates of the formula —O—P(=O)(O-alkyl)$_2$ or —O—P(=O)(O-alkyl)(O-aryl) or —O—P(=O)(O-aryl)$_2$.

The optional substituents of the alkyl, aryl and aralkyl radicals referred to above include hydroxyl, alkoxy, thio, alkylthio, halogen, amino, monoalkylamino, dialkylamino, amido, nitro, carboxyl, alkoxycarbony, alkylcarbonyl, and alkylcarbonyloxy substituents.

A "targeting ligand" as used herein refers to a molecule which has binding affinity for a cell type or structure of interest. Targeting ligands include, without limitation, antibodies or functional fragments thereof, receptors, receptor ligands, hormones, and members of specific binding pairs. The targeting ligand or compound may optionally be linked to a membrane permeant peptide sequence.

A "membrane permeant peptide sequence" refers to a peptide sequence which is able to facilitate penetration and entry of the HSP70 inhibitor across the cell membrane. Exemplary peptides include without limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

Compounds of the present invention which include the divalent linking moiety, —CR$_{10}$=CR$_{11}$—, for example, as used herein, encompass the cis/trans or E/Z stereoisomers thereof.

The compounds disclosed herein can exist as their corresponding salt, ester, or prodrug. As used herein, the term "pharmaceutically acceptable salts" refers to salts or zwitterionic forms of the compounds disclosed herein. Salts of such compounds can be prepared during the final isolation and purification of the compounds or separately by reacting the compound with an acid having a suitable cation. Suitable pharmaceutically acceptable cations include alkali metal (e.g., sodium or potassium) and alkaline earth metal (e.g., calcium or magnesium) cations. In addition, the pharmaceutically acceptable salts of the disclosed compounds that contain a basic center are acid addition salts formed with pharmaceutically acceptable acids. Examples of acids which can be employed to form pharmaceutically acceptable salts include inorganic acids such as hydrochloric, hydrobromic, sulfuric, and phosphoric, and organic acids such as oxalic, maleic, succinic, malonic, lactic and citric. Nonlimiting examples of salts of compounds of the invention include, but are not limited to, hydrochloride, hydrobromide, hydroiodide, sulfate, bisulfate, 2-hydroxyethansulfonate, phosphate, hydrogen phosphate, acetate, adipate, alginate, aspartate, benzoate, butyrate, camphorate, camphorsulfonate, citrate, digluconate, glycerolphosphate, hemisulfate, heptanoate, hexanoate, formate, succinate, malonate, fumarate, maleate, methanesulfonate, mesitylenesulfonate, naphthylenesulfonate, nicotinate, oxalate, pamoate, pectinate, persulfate, 3-phenylpropionate, picrate, pivalate, propionate, trichloroacetate, trifluoroacetate, glutamate, bicarbonate, undecanoate, lactate, citrate, tartrate, gluconate, benzene sulphonate, and p-toluenesulphonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

In light of the foregoing, any reference to compounds appearing herein is intended to include compounds disclosed herein as well as pharmaceutically acceptable salts, solvates (e.g., hydrates), esters, or prodrugs thereof. The pharmaceutically acceptable salts of the compounds of Formula I are prepared following procedures that are familiar to those of skill in the art.

Disclosed herein are compositions comprising the compounds as described above. The compositions comprise a therapeutically effective amount of the compounds or pharmaceutically acceptable salts thereof and a pharmaceutically acceptable carrier, adjuvant, and/or diluent. The compositions may optionally comprise additional therapeutic agents for the condition to be treated.

The compounds are employed in amounts effective to achieve their intended purpose. As used herein, a "therapeutically effective amount" means an amount effective to inhibit development of, or to alleviate the existing symptoms of, the condition of the subject being treated. "Dose-effective to inhibit" means an amount effective to inhibit development of, or to alleviate, aberrant cellular proliferation by promoting the accumulation and/or aggregation of mis-folded proteins or decrease aberrant cell proliferation, in vitro, in vivo, or ex vivo. Toxicity and therapeutic efficacy of such compounds can be determined by standard pharmaceutical procedures in cell cultures or experimental animals, e.g., for determining the LD$_{50}$ (the dose lethal to 50% of the population) and the ED$_{50}$ (the dose therapeutically effective in 50% of the population). The dose ratio between toxic and therapeutic effects is the therapeutic index, which is expressed as the ratio of LD$_{50}$ to ED$_{50}$. Compounds that exhibit high therapeutic indices (i.e., a toxic dose that is substantially higher than the effective dose) are preferred.

Modulation of HSP70 can be measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of compounds can be described as a sigmoidal curve expressing a degree of modulation as a function of concentration. The curve also theoretically passes through a point at which the concentration is sufficient to modulate activity of HSP70 to a level that is 50% that of the difference between minimal and maximal activity in the assay. This concentration is defined as the Inhibitory Concentration (50%) or IC$_{50}$ value. Determination of IC$_{50}$ values preferably is made using conventional biochemical (acellular) assay techniques or cell based assay techniques.

Comparisons of the efficacy of compounds often are provided with reference to comparative IC$_{50}$ values, wherein a higher IC$_{50}$ indicates that the test compound is less potent, and a lower $IC_{50}$ indicates that the compound is more potent, than a reference compound. Compounds demonstrating $IC_{50}$ values of less than about 1500 µM, or less than about 1000 µM, or less than about 250 µM, or less than about 100 µM, or less than about 50 µM, or less than about 20 µM, or less than about 1 µM can be employed in compositions or methods according to the invention.

The data obtained in such dose-response assays can be used as a factor in formulating a dosage range for use in subject, such as animals, mammals, and more specifically, humans. The dosage of such compounds preferably lies within a range of circulating concentrations that include the $ED_{50}$ with little or no toxicity. The dosage can vary within this range depending upon the dosage form, and the route of administration utilized.

The exact formulation, route of administration, and dosage is chosen by a subject's physician, or treating professional, in view of the subject's condition. Dosage amount and interval can be adjusted individually to provide plasma levels of the active compound that are sufficient to maintain desired therapeutic effects. In general, however, doses employed for humans typically are in the range of 0.001 mg/kg to about 1000 mg/kg per day. In some embodiments, doses range from about 0.1 to about 50 mg/kg, about 0.5 to about 40 mg/kg, about 0.7 to about 30 mg/kg, or about 1 to about 20 mg/kg. Specific doses contemplated include sub-ranges of any of the foregoing ranges in 0.1 mg/kg increments.

The pharmaceutical composition can contain components for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose, or dextrins); proteins (such as serum albumin, gelatin or immunoglobulins); coloring, flavoring; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides (preferably sodium or potassium chloride); delivery vehicles; diluents; excipients and/or pharmaceutical adjuvants. (Remington's Pharmaceutical Sciences, 18th Edition, A. R. Gennaro, ed., Mack Publishing Company (1990). The optimal pharmaceutical composition will be determined by one skilled in the art depending upon, for example, the intended route of administration, delivery format, and desired dosage. See, for example, Remington's Pharmaceutical Sciences, supra. Such compositions can influence the physical state, stability, rate of in vivo release, and rate of in vivo clearance of the compound of formula (I).

The primary vehicle or carrier in a pharmaceutical composition can be either aqueous or non-aqueous in nature. For example, a suitable vehicle or carrier can be water for injection, physiological saline solution, artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute therefore. The formulation components are present in concentrations that are appropriate for the choice route of administration. For example, buffers are used to maintain the composition at physiological pH or at a slightly lower pH, typically within a pH range of from about 5 to about 8.

The pharmaceutical compositions can be in the form of an aqueous solution, oleaginous suspension, dispersion or sterile powder, which can be used for the extemporaneous preparation of injectable solutions or dispersions. The suspension can be formulated according to the known art using those suitable dispersing or wetting agents and suspending agents which have been mentioned above. The compositions can also be dissolved or suspended in a non-toxic diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, fixed oils can be employed as a solvent or suspending medium. For this purpose, any bland fixed oil can be employed including synthetic mono- or diglycerides. In addition, fatty acids such as oleic acid find use in the preparation of injectables.

The disclosed compounds can be administered parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including, dermal, ocular, rectal, and nasal inhalation via insufflation aerosol. When parenteral administration is contemplated, the therapeutic compositions for use in this invention can be in the form of a pyrogen-free, parenterally-acceptable aqueous solution comprising the HSP70 modulator or inhibitor in a pharmaceutically acceptable vehicle. A particularly suitable vehicle for parenteral injection is sterile distilled water in which a HSP70 modulator is formulated as a sterile, isotonic solution, properly preserved. Yet another preparation can involve the formulation of the desired molecule with an agent, such as injectable microspheres, bio-erodible particles, polymeric compounds (such as polylactic or polyglycolic acid), or beads or liposomes, that provide for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a HSP70 modulator or inhibitor of Formula I can be formulated as a dry powder for inhalation. Inhalation solutions can also be formulated with a propellant for aerosol delivery. In yet another embodiment, solutions can be nebulized. Pulmonary administration is further described in PCT application no. PCT/US94/

001875, which describes pulmonary delivery of chemically modified proteins, but which can be applicable to pulmonary delivery of compounds as disclosed herein.

It is also contemplated that certain formulations can be administered orally. In one embodiment of the present invention, HSP70 modulators which are administered in this fashion can be formulated with or without those carriers customarily used in the compounding of solid dosage forms such as tablets and capsules. For example, a capsule can be designed to release the active portion of the formulation at a point in the gastrointestinal tract when bioavailability is maximized and pre-systemic degradation is minimized. Additional agents can be included to facilitate absorption of the HSP70 modulator. Diluents, flavorings, low melting point waxes, vegetable oils, lubricants, suspending agents, tablet disintegrating agents, and binders can also be employed.

Additional pharmaceutically acceptable ingredients are well known for the various types of formulation and can be for example binders such as natural or synthetic polymers, lubricants, sweetening and flavouring agents, coating materials, dyes, thickeners, antimicrobial agents, and carriers for the various formulation types. Nonlimiting examples of binders useful in a composition described herein include gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers can be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan.

Non-limiting examples of excipients useful in a composition described herein include phosphates such as dicalcium phosphate. Nonlimiting examples of lubricants use in a composition described herein include natural or synthetic oils, fats, waxes, or fatty acid salts such as magnesium stearate.

Surfactants for use in a composition described herein can be anionic, anionic, amphoteric or neutral. Non-limiting examples of surfactants useful in a composition described herein include lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Non-limiting examples of sweetening agents useful in a composition described herein include sucrose, fructose, lactose or aspartame. Non-limiting examples of flavoring agents for use in a composition described herein include peppermint, oil of wintergreen or fruit flavors such as cherry or orange flavor. Non-limiting examples of coating materials for use in a composition described herein include gelatin, wax, shellac, sugar or other biological degradable polymers. Nonlimiting examples of preservatives for use in a composition described herein include methyl or propylparabens, sorbic acid, chlorobutanol, phenol and thimerosal.

Another pharmaceutical composition can include an effective quantity of HSP70 modulator in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions useful in the practice of this invention will be evident to those skilled in the art, including formulations capable of sustained- or controlled-delivery formulations of HSP70 modulators. Techniques for formulating a sustained- or controlled-delivery vehicles, such as liposome carriers, bio-erodible microparticles or porous beads and depot injections, are also known to those skilled in the art. See for example, PCT Application No. PCT/US93/00829, which describes the preparation of a porous polymeric microparticle vehicle for the controlled release of pharmaceutical compositions. Additional examples of sustained-sustained-release preparations include semipermeable polymer matrices in the form of shaped articles, e.g. films or microcapsules. Sustained release matrices can include polyesters, hydrogels, polylactides (U.S. Pat. No. 3,773,919 and EP 058 481), copolymers of glutamic acid and gamma ethyl-L-glutamate (Sidman et al., Biopolymers, 22:547-556 (1983)), poly(2-hydroxyethyl-methacrylate) (Langer et al., J. Biomed. Mater. Res., 15:167-277 (1981) and Langer, Chem. Tech., 12:98-105 (1982)), ethylene vinyl acetate (Langer et al., supra) or poly-D-3-hydroxybutyric acid (EP 133 988). Sustained-release vehicles in the form of liposomes can be prepared by any of several methods known in the art. See e.g., Eppstein et al., Proc. Natl. Acad. Sci. USA, 82:3688-3692 (1985); EP 88 046; 036 676; and EP 143,949.

The pharmaceutical composition to be used for in vivo administration typically must be sterile. This can be accomplished by filtration through sterile filtration membranes. Where the composition is lyophilized, sterilization using these methods can be conducted either prior to, or following lyophilization and reconstitution. Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration. In addition, compositions can be placed into a container having a sterile access port, for example, an intravenous solution bag or vial having a stopper pierceable by a hypodermic injection needle.

The compounds employed in the methods of the present invention can be administered by any means that results in the contact of the active agent with the agent's site of action in the body of a patient. The compounds can be administered by any conventional means available for use in conjunction with pharmaceuticals, either as individual therapeutic agents or in a combination of therapeutic agents. For example, they can be administered as the sole active agent in a pharmaceutical composition, or they can be used in combination with a second or additional therapeutic agent.

As used herein, the term "sensitize" means that the effect of the particular therapeutic is enhanced in the presence of or by co-administration with a second therapeutic. Indeed, the present inventors have found that combined administration of the compound of Formula I with a conventional chemotherapeutic agent such as cisplatin potentiated the anti-neoplastic action of cisplatin. Correspondingly, the inventors have also discovered that cotreatment of tumor cells with the compound of Formula I and anticancer agent such as 17-allylamino-17-demethoxygeldanamycin (17-AAG) further increased the degree of proliferative arrest and the cytocidal effect of 17-AAG in tumor cells.

The combination therapy described herein may also be practiced using other biologically active agents, including, but not limited to, a member the group consisting of ribavirin, protease inhibitors, polymerase inhibitors, small interfering RNA compounds, anti-sense oligonucleotides, nucleotide analogs, nucleoside analogs, immunoglobulins, hepatoprotectants, anti-inflammatory agents, antibiotics, antivirals, anti-infective compounds and biological agents useful for antibody mediated therapy, or a combination of such agents. Such agents include, without limitation, cetuximab (anti-EGFR antibody), trastuzumab (anti-HER2 antibody), and Remicade®, which impacts the TNF pathway.

In specific embodiments, the compounds of this invention can, when used in cancer therapy, be used together with other substances and compounds, such as chemotherapeutic agents. Such compounds are, for example (according to the general classes of the compounds): Alkylating agents: Nitrogen mustards (mechlorethamine; cyclophosphamide; ifosfamide; melphalan; chlorambucil); Nitrosoureas (carmustine (BCNU); lomustine (CCNU); semustine (methyl-CCNU)); Ethylenimine/Methylmelamine (thriethylenemelamine (TEM); triethylene thiophosphoramide (thiotepa); hexamethylmelamine (HMM, altretamine)); Alkyl sulfonates (busulfan); Triazines (dacarbazine (DTIC)); and Antimetabolites (Folic Acid analogs—methotrexate and trimetrexate; Pyrimidine analogs—5-fluorouracil, fluorodeoxyuridine, gemcitabine, cytosine arabinoside, 5-azacytidine, 2,2'-difluorodeoxycytidine); Purine analogs—6-mercaptopurine, 6-thioguanine, azathioprine, 2'-deoxycoformycin (pentostatin), erythrohydroxynonyladenine (EHNA), fludarabine phosphate, and 2-Chlorodeoxyadenosine (cladribine, 2-CdA)); Type I Topoisomerase Inhibitors: camptothecin; topotecan; irinotecan; Natural products: Antimitotic drugs (paclitaxel; Vinca alkaloids—vinblastine (VLB), vincristine, and vinorelbine; Taxotere® (docetaxel); estramustine; estramustine phosphate); Epipodophylotoxins (etoposide and teniposide); Antibiotics (actimomycin D; daunomycin (rubidomycin); doxorubicin (adriamycin); mitoxantrone; idarubicin; bleomycins; plicamycin (mithramycin); mitomycinC; and dactinomycin); Enzymes (L-asparaginase); Biological response modifiers: interferon-alpha; IL-2; G-CSF; and GM-CSF; Differentiation Agents: retinoic acid derivatives; Radiosensitizers: metronidazole, misonidazole, desmethylmisonidazole, pimonidazole, etanidazole, nimorazole, RSU 1069, E09, RB 6145, SR4233, nicotinamide, 5-bromodeozyuridine, 5-iododeoxyuridine, bromodeoxycytidine, Miscellaneous agents: Platinum coordination complexes (cisplatin, carboplatin); Anthracenedione (mitoxantrone); Substituted urea (hydroxyurea); Methylhydrazine derivatives (N-methylhydrazine (MIH) and procarbazine); Adrenocortical suppressant (mitotane (o,p'-DDD) and aminoglutethimide); Cytokines (interferon (α, β, γ) and interleukin-2); Hormones and antagonists: Adrenocorticosteroids/antagonists (prednisone and equivalents; dexamethasone; aminoglutethimide); Progestins (hydroxyprogesterone caproate; medroxyprogesterone acetate; megestrol acetate); Estrogens (diethylstilbestrol, ethynyl estradiol/equivalents); Antiestrogen (tamoxifen); Androgens (testosterone propionate, fluoxymesterone/equivalents); Antiandrogens (flutamide; gonadotropin-releasing hormone analogs, leuprolide); Nonsteroidal antiandrogens (flutamide); Photosensitizers: hematoporphyrin derivatives, Photofrin®, benzoporphyrin derivatives, Npe6, tin etioporphyrin (SnET2), pheoboride-a, bacteriochlorophyll-a, naphthalocyanines, phthalocyanines, and zinc phthalocyanines; Proteosome inhibitors: bortezomib (Velcade®). In addition to the above, there are several novel compounds disclosed in various patent applications that are contemplated as second therapeutic agents, e.g. combretastatins from Bristol Myers Squibb, Epothilones (US 2005244413), serratamolide (US 2005239694), indol derivatives (US 2005239752), various plant extracts: extract of sea buckthorn—*Hippophae rhamnoides* (US 2005214394), extracts of *Ganoderma lucidum, Salvia miltiorrhiza* and *Scutellaria barbata* (US 2005208070), chk1 inhibitors (WO 2006/021002; WO/2006/014359; WO 2006/012308; WO 2005/027907; WO 2002/070494; WO 1999/011795); the contents of the afore-mentioned patents and patent applications are herewith incorporated by reference in their entireties. Also suitable are tyrosine kinase inhibitors. Specific tyrosine kinase inhibitors include, but not limited to imatinib mesylate (marketed as Gleevec or Glivec; previously known as STI-571), dasatinib, nilotinib, MK-0457 (formerly known as VX-680), and Omacetaxine (formerly known as Ceflatonin). In certain embodiments of the invention the use of cisplatin is excluded in the method of treatment disclosed herein.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy. PES and functional analogs thereof can be combined with radiation and/or other chemotherapeutic agents to synergistically kill cancer cells.

Depending on the neoplastic condition, pharmaceutical compositions of the invention can be formulated to include one or more cytokines, lymphokines, growth factors, or other hematopoietic factors which can reduce negative side effects that may arise from, or be associated with, administration of the pharmaceutical composition alone. Cytokines, lymphokines, growth factors, or other hematopoietic factors particularly useful in pharmaceutical compositions of the invention include, but are not limited to, those that are commercially available by such companies as R&D Systems (Minneapolis, Minn.).

In certain embodiments, HSP90 modulators can be included as the second therapeutic agent. HSP90 is a molecular chaperone that plays a key role in regulating the stability and activation state of a range of "client" proteins critical for signal transduction and a diverse set of cellular functions, such as cell growth, differentiation, motility, and death. HSP90 also plays a role in cyclin dependent progression through G1 and G2 and in centrosome function in mitosis. In normal cells, HSP90 is involved in the triage of misfolded proteins under stress. In contrast, HSP90 plays an instrumental role in cancer cells by chaperoning the correct folding, localization, and function of a variety of mutated and/or overexpressed oncoproteins. HSP90 substrates include a number of steroid hormone receptors including the androgen receptor (AR), estrogen receptor, and glucocorticoid receptor. Owing to the critical roles played by HSP90 in oncogenesis, cancer, disease progression, and viral infection, a number of HSP90 modulators have been identified and tested in clinical trials. HSP90 modulators include, without limitation, those described in U.S. Pat. Nos. 7,160,885; 6,946,456; 6,747,055; and 6,670,348; U.S. Patent Publication No. 2007/0087998; 2007/0072855; 2007/0043044; 2007/0032532; 2007/0027150; 2007/0010432; 2006/0223797; and 2006/0205705; and International Patent Publications WO96/33989; WO98/18780; WO99/55689; and WO02/16369, each of which is incorporated in its entirety by reference herein. Specific Hsp90 modulators include geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

The efficacies of present HSP90-targeted therapeutics have been hindered by the concomitant induction of prosurvival HSP70 protein following HSP90 inhibitor administration. The induced HSP70, following treatment of HSP90 modulators, then complexes with HSP90 to promote cell cycle control, cell growth, and oncogenesis in cancer cells. In contrast, disrupting the function of the HSP70/90 complex by co-administration of HSP70 siRNA oligonucleotides and HSP90 inhibitor such as 17-AAG has been implicated to increase tumor cell death. Consequently, the ability of certain HSP70/90 complex inhibitors to cause this protein complex to selectively target its substrate proteins for degradation makes the HSP70/90 complex an especially desirable anti-cancer target. Because the HSP70/90 complex comprises both HSP70 and HSP90, administration of compounds which modulate both HSP70 and HSP90 can be beneficial in sensitizing the effect of each in the presence of the other. Thus, in some embodiments, the methods or use of the compounds disclosed herein further comprise administration or use of a second therapeutic, such as a HSP90 inhibitor, wherein either co- or sequential administration of the second therapeutic sensitizes the effect of the compound of formula (I), or the administration of the compound (I) sensitizes the effect of the second therapeutic. Also see US Patent Application 2007/0259820.

In another approach for enhancing transport, a peptidic or peptidomimetic compound is conjugated to a second peptide or protein, thereby forming a chimeric protein, wherein the second peptide or protein undergoes absorptive-mediated or receptor-mediated transcytosis. Chimeric proteins can be formed by recombinant DNA methods (e.g., by formation of a chimeric gene encoding a fusion protein) or by chemical crosslinking of the modulator to the second peptide or protein to form a chimeric protein. Numerous chemical crosslinking agents are known in the art (e.g., commercially available from Pierce Biotechnology, Inc., Rockford, Ill.). A crosslinking agent can be chosen which allows for high yield coupling of the HSP70 inhibitors to the second peptide or protein and for subsequent cleavage of the linker to release bioactive modulator. For example, a biotin-avidin-based linker system may be used.

When necessary, in order to promote penetration of tissues and/or the blood-brain-barrier (BBB), the active compounds can be administered by using strategies for gaining drug access to the brain as well as tissues. Various strategies known in the art for increasing transport across the BBB can be adapted to the compounds of the invention to thereby enhance transport of the modulators across the BBB (for reviews of such strategies, see e.g., Pardridge. Trends in Biotechnol. 12:239-245 (1994); Van Bree, et al. Pharm. World Sci. 15:2-9 (1993); and Pardridge, et al. Pharmacol. Toxicol. 71:3-10 (1992)). In one approach, the compound is chemically modified to form a prodrug with enhanced transmembrane transport. As used herein, the term "prodrug" is intended to include any covalently bonded carriers which release the active parent drug or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.), the compounds employed in the present methods can, if desired, be delivered in prodrug form. Thus, the present invention contemplates methods of delivering prodrugs. Prodrugs of the compounds employed in the present invention can be prepared by modifying functional groups present in the compound in such a way that the modifications are cleaved, either in routine manipulation or in vivo, to the parent compound. Suitable chemical modifications include covalent linking of a fatty acid to the compound through an amide or ester linkage (see e.g., U.S. Pat. No. 4,933,324 and PCT Publication WO 89/07938; U.S. Pat. No. 5,284,876; Toth, et al. J. Drug Target. 2:217-239 (1994); and Shashoua, et al. J. Med. Chem. 27:659-664 (1984)) and glycating the compound (see e.g., U.S. Pat. No. 5,260,308). Also, N-acylamino acid derivatives may be used in a modulator to form a "lipidic" prodrug (see e.g., U.S. Pat. No. 5,112,863).

The chemotherapeutic agent and HSP70 inhibitor can be administered sequentially, that is delivery of one component, followed by the other component at different times and/or at different frequencies or the two components can be administered as a combination either simultaneously or concurrently. In other words, treatment using both components at the same time can be carried out using both compounds at the same dosage or each one in separate dosage. The dosages for both concurrent and sequential delivery will depend on absorption, distribution, metabolism, and excretion rates of the components of the combination, as well as other factors known to one of skill in the art. Dosage values will also vary with the severity of the disease being treated. It is to be further understood that for any particular subject, specific dosage regimens and schedules may be adjusted over time according to the individual's needs and the professional judgment of the clinician administering the therapy.

In antimicrobial or bacteriostatic applications, the compounds of Formula I may be combined with heat as well as one or more anti-microbial agents. Such agents, include without limitation, penicillin, cephalosporins, aminoglycosidic antibiotics, fluoroquinolones, nitrofurans, vancomycin, monobactams, co-trimoxazole, and metronidazole. The bacteriostatic agent includes, but are not limited to, the tetracyclines, sulphonamides, spectinomycin, trimethoprim, chloramphenicol, macrolides and lincosamides. Additional antibacterial compounds and their derivatives belonging to classes such as Aminoglycosides, Carbacephem, Carbapenems, Cephalosporins, Glycopeptides, Macrolides, Monobactams, Penicillins, Quinolones, Sulfonamides, Tetracyclines, and others (e.g. Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampin/Rifampicin, Tinidazole).

The following materials and methods are provided to facilitate the practice of the present invention.

Preparation of Biotin-Conjugated PES

Sulfo-NHS-SS-Biotin (Biotin) and PES (2-Phenylethynesulfonamide or Pifithrin-µ) were purchased from Pierce Biotechnology, Inc. (Rockford, Ill.) and EMD Chemicals, Inc. (Gibbstown, N.J.), respectively. The biotinylated form of PES (B-PES) was produced as indicated by Pierce, by mixing a 10 mM solution of Sulfo-NHS-SS-Biotin with 1.5 mg of PES, followed by a 30 min incubation at 25° C. Subsequently, 50 mM Tris-HCl (pH 8) was added to the Biotin-PES (B-PES) mixture to quench any non-reacted biotinylation reagent.

Identification of B-PES Interacting Proteins

Human osteosarcoma cell line U2OS stably expressing BCL-xL (BX-U2OS) and human melanoma cell line A875 were treated with 20 µM Biotin or B-PES for 24 h. $E.\ coli$ strain DH5α cells were treated with 50 µM Biotin or 50 µM B-PES for 3 h. Following exposure to Biotin or B-PES, cells were harvested and centrifuged at 500 g for 5 min at 4° C. The $E.\ coli$ DH5α cells were resuspended in Buffer A [50 mM Tris-HCl (pH 7.5), 5 mM EDTA, 150 mM NaCl, 0.5% CHAPS]. The BX-U2OS whole cell extracts were prepared using Buffer B (200 mg/L KCl, 200 mg/L $KH_2PO_4$, 8000 mg/L NaCl, 2160 mg/L $Na_2HPO_4$-$7H_2O$, 0.5% Triton X-100, 0.5% NP-40, pH 7.4). The A875 whole cell homogenates were prepared using Buffer C [50 mM Tris-HCl (pH 7.5), 100 mM KCl, 2 mM EDTA, 1% NP-40]. Buffers A, B, and C were supplemented with protease inhibitors [8 µg/ml aprotinin, 8 µg/ml leupeptin and 1 mM phenylmethylsulphonyl fluoride (PMSF)], immediately prior to use. Cell disruption was performed by passing the cells through a 23-gauge needle 3-5 times, and the homogenates were gently rocked on a rocker at 4° C. for 30 min. The homogenates were spun at 11,000 g for 10 min at 4° C. The supernatants were removed and spun at 11,000 g for 10 min at 4° C. twice. Since the NeutrAvidin Resin (Pierce Biotechnology, Inc.) binds preferentially to biotinylated molecules, 100-200 µl of pre-washed NeutrAvidin Resins were added to 10-20 mg of supernatants (whole cell extracts), and the mixtures were incubated at 4° C. for 1 h on a rocker. The B-PES immunocomplex-NeutrAvidin Resins were washed three times using the indicated buffer. The captured B-PES-immunocomplexes bound to the NeutrAvidin Resins were either resuspended directly in 2×SDS-Loading Buffer (100 mM Tris-HCl at pH 6.8, 4% SDS, 0.2% bromophenol blue, 20% glycerol and 10% 2-mercaptoethanol), or eluted using 100 mM DTT, which cleaves the disulfide bond in the spacer arm of the biotin attached to PES. The associated proteins were resolved by SDS-PAGE in a 4%-20% gradient gel (Lonza Rockland, Inc., Rockland, Me.) and visualized by Coomassie staining (Bio-Rad Laboratories, Inc., catalogue number 161-0786). The results revealed a Coomassie-stained band of ~70 kDa that was excised from the gel and subjected to trypsin digestion, and the resulting peptides were analyzed by liquid chromatography—tandem mass spectrometry at the Genomics Institute and Abramson Cancer Center Proteomics Core Facility, University of Pennsylvania School of Medicine. The results indicate that the interacting protein was HSP70 in mammalian cells and its orthologue DnaK in $E.\ coli$.

Cell Proliferation and Survival Assays

Cell viability assays were performed using an MTT (methyl thiazolyl tetrazolium) colorimetric assay (Roche Applied Science, Cat. No. 11 465 007 001), with the following modifications. Briefly, cells ($1 \times 10^4$) were plated into 24 well-assay plates in 0.5 ml media and allowed to attach overnight. Cells were then treated with PES, cisplatin (EMD Chemicals, Inc.), or 17-AAG (EMD Chemicals, Inc.), either individually or in combination, as indicated. After the incubation period, 50 µl of the water-soluble MTT labeling reagent [3-[4,5-dimethylthiazol-2-yl]-2,5-diphenyl tetrazolium bromid] were added to the cells, and the cells were incubated for 4 h in a humidified chamber at 37° C. with 5% $CO_2$. The metabolized insoluble formazan crystals were then solubilized using 0.5 ml of the Solubilization solution (10% SDS in 0.01M HCl) per well, and the resulting colored solutions were spectrophotometrically quantified at an absorbance of 570 nm.

Immunoblotting, Immunoprecipitation, In Vitro Binding, Antibodies, and HSP70 shRNA For immunoprecipitation studies employing whole cell extracts, cells were lysed in Buffer C supplemented with protease inhibitors [8 µg/ml aprotinin, 8 µg/ml leupeptin and 1 mM phenylmethylsulphonyl fluoride (PMSF)], and whole cell homogenates were prepared as described above and previously. Immunoblotting (Western blotting) of cultured cell extracts was performed as described (Dumont et al., 2003; Leu and George, 2007). In vitro transcription/translation was performed with the TNT T7 Quick Coupled Transcription/Translation System (Promega Corporation, Madison, Wis.). Redivue L-$^{35}$S-Methionine was purchased from Amersham Biosciences (Piscataway, N.J.). pCMV6-HSP90 and pCMV6-HSP70 constructs were purchased from OriGene Technologies, Inc. (Rockville, Md.). In vitro binding experiments were performed by mixing B-PES coupled to NeutrAvidin agarose resins with either $^{35}$S-labelled in vitro translated HSP70 or HSP90 protein in IVT Buffer (200 mg/L KCl, 200 mg/L $KH_2PO_4$, 8000 mg/L NaCl, 2160 mg/L $Na_2HPO_4$-$7H_2O$, pH 7.4) for 3 h at 4° C. The captured B-ESHSP70-immunocomplexes bound to the NeutrAvidin resins were washed extensively using IVT Buffer, and eluted using 100 mM DTT. The associated proteins were resolved by SDS-PAGE in a 4%-20% gradient gel (Lonza Rockland, Inc., Rockland, Me.) and visualized by autoradiography. The following primary antibodies were used in this work: anti-caspase-3, anticaspase-8 (human specific), anti-CHIP, anti-HSP90, anti-HSP40, anti-HSP70, and anti-LC3 (Cell Signaling Technology, Inc. Danvers, Mass.); anti-p53 (AB-6) and anti-MDM2 (EMD Chemicals, Inc., Gibbstown, N.J.); anti-LAMP2 and anti-p62 [SQSTM1 (D-3): sc-28359, Santa Cruz Biotechnology, Inc., Santa Cruz, Calif.]; anti-BAK NT and anti-CHIP (Upstate Biotechnology USA, Inc.); anti-BCL-xL, anti-BAG-1, and anti-Cathepsin L (BD Biosciences, San Jose, Calif.); anti-HSP70 (R&D Systems, Inc., Minneapolis, Minn.), and anti-HSP70 and anti-HSC70 (Abcam Inc., Cambridge, Mass.). The peroxidase-conjugated secondary antibodies (i.e. donkey anti-rabbit, donkey anti-mouse, and donkey anti-goat) were from Jackson ImmunoResearch Laboratories, Inc. Four distinct shRNA sequences against HSP70 (ACGGCAAGGTGGAGAT-CATCGCCAACGAC; SEQ ID NO: 1) ACGACGGCATCT-TCGAGGTGAAGGCCACG, (SEQ ID NO: 2) GGCCAT-GACGAAAGACAACAATCTGTTGG (SEQ ID NO: 3), and GCCTTCAACATGAAGAGCGCCGTGGAGGA; SEQ ID NO: 4), as well as negative controls (hairpin control, sh-Negative) were cloned into the control expression vector pRS. The pre-designed shRNA silencing kit (4 gene-specific shRNA and two negative controls) is available from Origene (Rockville, Md.). The cells were transfected with indicated shRNAs using the Lipofectamine LTX Reagent (Invitrogen, Carlsbad, Calif.) according to manufacturer's instructions.

Immunofluorescence

BX-U2OS cells ($2 \times 10^4$) were seeded onto 2 well chamber slides (Fisher Scientific, Pittsburgh, Pa.) in 1 ml media per well and allowed to attach overnight. Cells were then treated with 20 µM PES for 24 h, fixed in 3.7% formaldehyde prepared in 1×PBS for 15 min at room temperature, permeabilized with ice-cold 100% methanol at −20° C. for 10 min, and incubated with 5% Normal Donkey Serum in PBT [200 mg/L KCl, 200 mg/L $KH_2PO_4$, 8000 mg/L NaCl, 2160 mg/L $Na_2HPO_4$-$7H_2O$, 0.1% BSA, 0.2% Triton X-100] for 30 min at 37° C. We analyzed p62 immunofluorescence using anti-p62 monoclonal antibody [SQSTM1 (D-3): sc-28359, Santa Cruz Biotechnology, Inc., Santa Cruz, Calif.] at a 1:200 dilution in PBT, and Cy3-conjugated donkey secondary antibody against mouse (Jackson Immunoresearch Laboratories) at a 1:600 dilution in PBT.

Pulse-Chase Experiments

The cells were seeded at ~50% confluency in 10 ml of DMEM/10% FBS/1× Pen-Strep using 100 mm dish. Next day, the cells were washed extensively in PBS and starved in "methionine/cysteine-free DMEM" (Invitrogen SKU#21013-024) with 5% dialyzed FBS and 1× Pen/Strep for 30 min. Either [$^{35}$S] Methionine/Cysteine (500 µCi) and DMSO or [$^{35}$S] Methionine/Cysteine (500 µCi) and 20 µM PES were added to the cells for 1 h. The cells were washed extensively to remove [$^{35}$S] Methionine/Cysteine, and chased in complete media containing 5% dialyzed FBS, 3 mM cold methionine, and 3 mM cold cysteine for the indicated times, either in the presence of DMSO or 20 µM PES. The cells were lysed in 1% NP-40 Lysis Buffer (50 mM Tris-HCl, pH 7.5; 100 mM KCl; 2 mM EDTA; 1% NP-40; 6 µg/ml Leupeptin; 6 µg/ml Aprotinin; 1 mM PMSF), and centrifuged at 10,000×g (14,000 rpm) for 15 min at 4° C. The resultant pellets (the detergent insoluble fraction) were resuspended in 1×SDS-Loading Buffer. The resultant supernatants (detergent soluble fraction) were spun at 10,000×g (14,000 rpm) for 10 min at 4° C. to remove residual detergent insoluble debris. Equal volume of 2×SDS Loading Buffer was added to the detergent soluble fractions. The samples were boiled for 5 min. The proteins were resolved by SDS-PAGE in a 4%-20% gradient gel (Lonza Rockland, Inc., Rockland, Me.) and visualized by autoradiography.

Long-Lived Protein Degradation Assay

The long-lived protein degradation assays were performed as described (Humbey et al., 2008; Pimkina et al., 2008), but with the following modifications. The cells were seeded at 30% confluency. The cells were then labeled at 37° C. for 14 h in L-valine-free medium supplemented with dialyzed FBS medium containing 0.2 mCi/ml of L-[$^{14}$C]valine (Amersham Pharmacia). After the radiolabeling period, unincorporated radioisotope was removed by three rinses with PBS (pH 7.4). Cells were then incubated at 37° C. in fresh complete media [Dulbecco's modified Eagle's medium (DMEM), 10% fetal bovine serum (FBS), 1% penicillin-streptomycin (PS)] containing 2 mM unlabeled valine for 10 h to allow the degradation of labeled short-lived proteins. Cells were then rinsed 3 times with PBS (pH 7.4), and grown in fresh complete media [DMEM, 10% FBS, 1% PS] containing either DMSO or 20 µM PES. Aliquots of the media (0.2 ml in duplicate) were taken at 0 h, 4 h, 8 h, 24 h, and 48 h and mixed with 0.2 ml of 1% bovine serum albumin and 0.4 ml of 40% trichloroacetic acid (v/v). After 15 min on ice, the mixtures were centrifuged at 17,000 g for 10 min and the supernatant (containing unincorporated $^{14}$C valine) was mixed with 4 ml of scintillation liquid. The pellet (containing incorporated $^{14}$C valine) was dissolved in 0.8 ml of 0.2 N NaOH. Radioactivity in the aliquots was measured on a Beckman liquid scintillation system. The percentage of long-lived protein degraded was obtained by the formula % degradation=($^{14}$C counts at timepoint/sum of $^{14}$C counts at each time point+total cell-associated radioactivity)×100.

Mouse Model

To evaluate the efficacy of PES as a chemopreventative agent, Eµ-Myc transgenic mice were injected every 5 days, starting at 8 weeks of age, with either vehicle or PES (40 mg/kg) prepared in PBS. All animals received a total of 7 injections, either with PES or vehicle. Consequently, no injection was given after day 86. All mice were observed daily for signs of morbidity and the development of lymphoma. All experiments with mice were approved by, and conformed to, the guidelines of the Institutional Animal Care and Use Committee of the Fox Chase Cancer Center. These mice may also be used to advantage to test the beneficial therapeutic combinations of agents and/or treatments described herein.

Sulforhodamine B Colorimetric Assay

Cells (2×10$^4$) were plated into 96 well plates in 200 µl media and allowed to attach overnight. Cells were then treated with the indicated doses of PES, cisplatin or PES+Cisplatin. After 72 hr incubation period, cells were washed in PBS and 100 µl of ice cold 10% TCA was added for 1 hr at 4° C. Plates were washed four times with slow-running tap water and air-dried at room temperature. 100 µl of 0.057% SRB solution was added to the cells and incubated for 30 min at room temperature. Fixed cells were quickly rinsed four times with 1% acetic acid to remove unbound dye. The protein-bound dye was solubilized using 200 µl of 10 mM Tris base solution (pH 10.5) per well, and the wells were spectrophotometrically quantified at an absorbance of 540 nm. This methodology is identical to that in Shekan et al, JNCI 82:1107 (1990).

Colony Formation Assay

Fadu or Scc 61 (squamous cell carcinoma of the head and neck) cell lines were grown in DMEM supplemented with 10% fetal bovine serum and antibiotics. Cells were pre-treated with PES (10 µM) for 24 hr after which they were subject to gamma radiation (either 2 or 10 Gy) and plated at different densities in 6 well plates; the wells depicted were plated at 2000 cells/well. After 10 days, colonies were stained with crystal violet.

The following examples are provided to illustrate certain embodiments of the invention. They are not intended to limit the invention in any way.

Example I

PES Interacts with HSP70

PES was identified in a screen of the Chembridge DIVERSet library of drug-like small molecules for those exhibiting an ability to inhibit the direct mitochondrial pathway of p53-mediated apoptosis, and was referred to as PFTµ (Strom et al., 2006). Subsequently, we found that PES prevents the accumulation of p53 at mitochondria and inhibits caspase cleavage following cisplatin treatment of a human tumor cell line (Leu and George, 2007). In an attempt to better understand the molecular basis for these observations, we sought to identify intracellular targets of PES.

Figure 1:
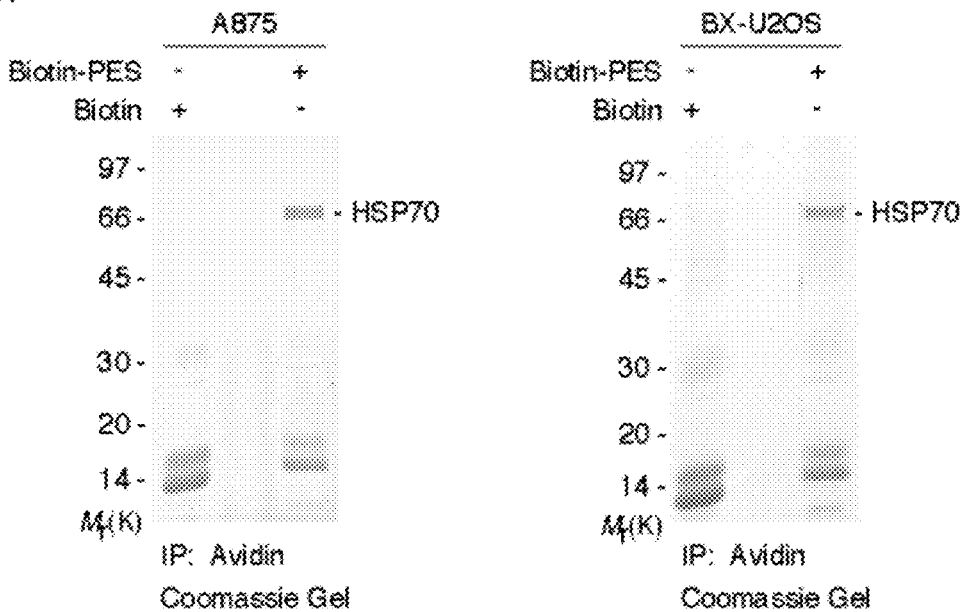
FIG. 1. PES Binds to HSP70. (A) Whole cell extracts (WCE) prepared from A875 and BCL-xL over-expressing U2OS human osteosarcoma cells (BX-U2OS) cells, treated with Biotin or Biotin-PES (B-PES), were captured using NeutrAvidin agarose resins. HSP70-family proteins were identified as the major product in the excised band of ~70 kDa shown in both Coomassie gels. HSP70 and HSC70 peptide sequences are shown in FIG. 2B. (B and C) WCE were prepared from the cell lines indicated following 24 h treatment with 20 µM Biotin or B-PES and examined for the expression of proteins indicated (left panel of B and C) by western blot analysis; note that different exposure times were used to visualize these proteins. B-PES-containing complexes were captured by NeutrAvidin Resins, and eluted following 100 mM DTT treatment Immunoprecipitation-western blot (IP-WB) analysis using the indicated antibodies reveals interaction of B-PES with endogenous HSP70, but there is no detectable interaction with endogenous BAK, BCL-xL, GRP78, p53, HSC70, or HSP90 even after longer exposure times. (D) In vitro evidence for an interaction between B-PES and HSP70. Full-length human HSP70 and human HSP90 proteins were in vitro translated in the presence of $^{35}$S-methionine, mixed with B-PES coupled to NeutrAvidin resins, and eluted using 100 mM DTT. The resulting DTT eluates were separated by polyacrylamide gel electrophoresis (SDS-PAGE) and visualized by autoradiography. (E) B-PES interacts with the C-terminal region of HSP70. H1299 cells were transfected with the indicated hemagglutinin (HA)-tagged constructs and exposed to B-PES. B-PES containing complexes were captured by NeutrAvidin Resins, eluted following 100 mM DTT treatment, and immunoblotted with anti-HA antibody following SDS-PAGE. (F) Non-transformed human IMR90 fibroblasts or H1299 lung carcinoma cells were treated with the indicated concentrations of PES for 24 h and cell viability was determined by MTT assays. (G) WCE were prepared from the cell lines indicated following 5 hr treatment with 20 µM PES or B-PES and examined for the expression of proteins indicated (left panel) by western blot analysis; note that different exposure times were used to visualize these proteins. B-PES-containing complexes were captured by NeutrAvidin resins, eluted following 50 mM DTT treatment, and immunoblotted using the indicated antibodies.
Figure 1:
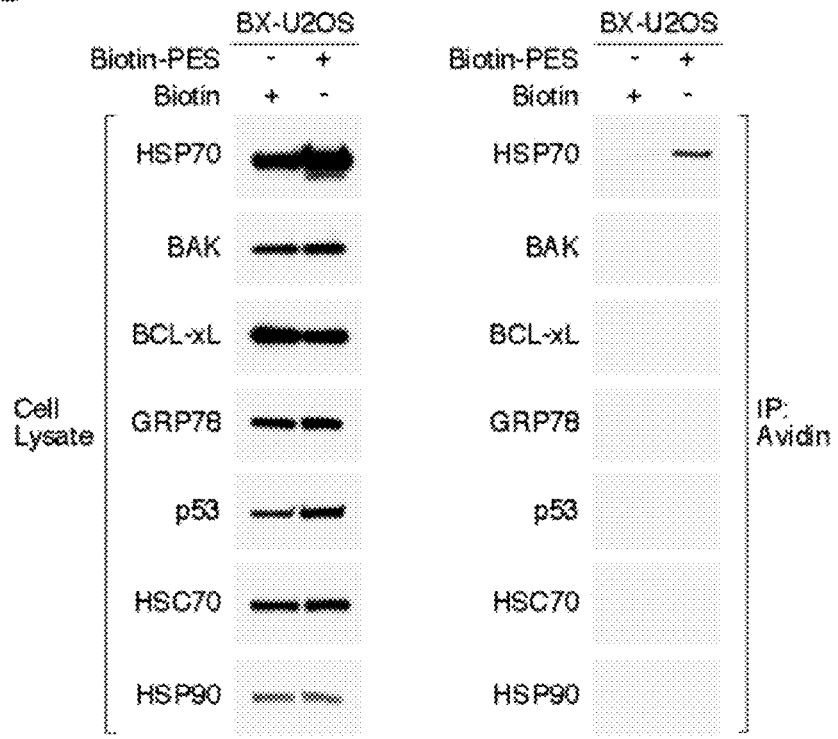
Figure 1:
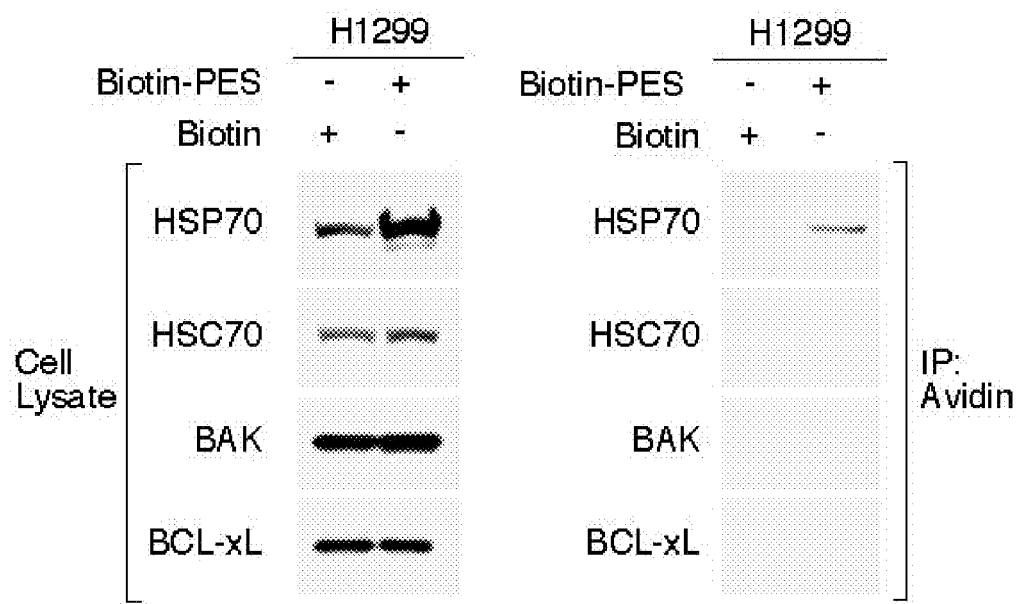
Figure 1:
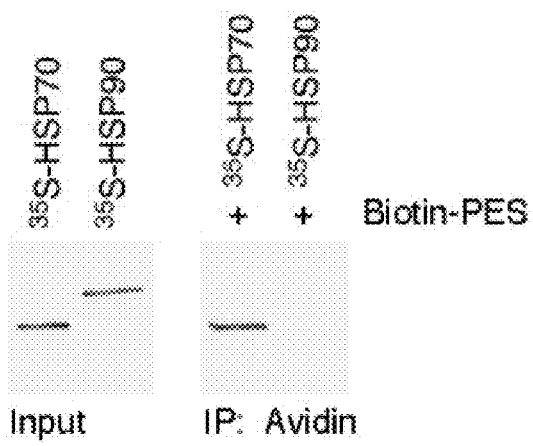
Figure 1:
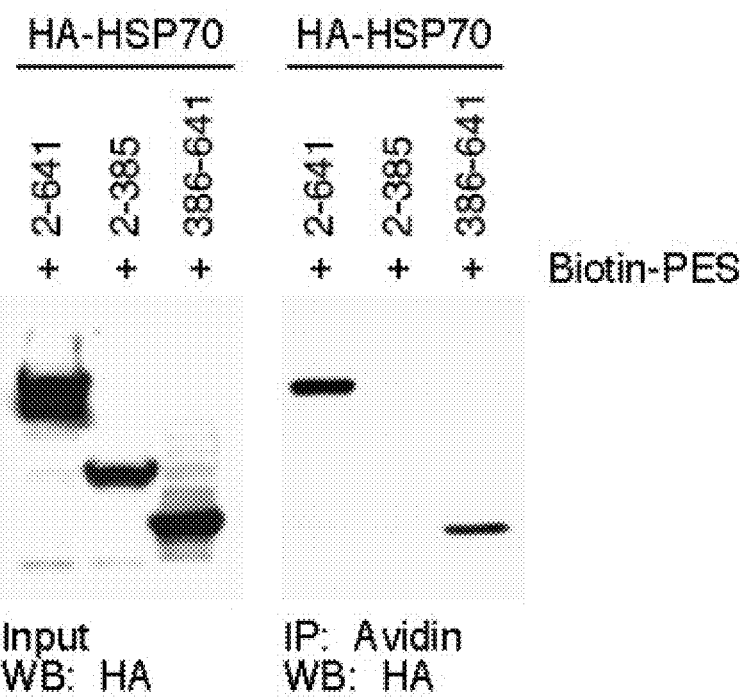
Figure 1:
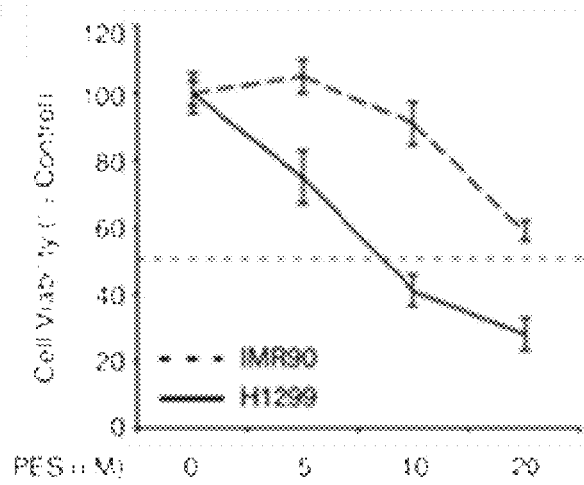
Figure 1:
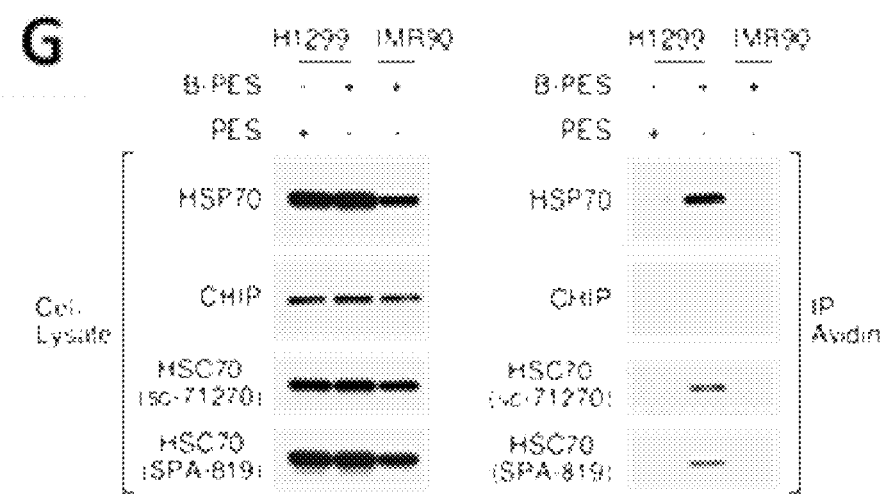
Figure 2:
FIG. 2. The Interaction of B-PES and HSPs. (A) Chemical structure of PES (from EMD Chemicals, Inc.). (B) The amino acid sequence of inducible HSP70 (SEQ ID NO: 5) and HSC70 (SEQ ID NO: 6); the residues detected by mass spectrometry are shown in bold and underlined. (C) WCE were prepared from U2OS cells following 24 h treatment with 20 µm Biotin or B-PES, and immunoblotted for the proteins as indicated (left). B-PES-containing complexes were captured by NeutrAvidin Resins, and eluted following 100 mM DTT treatment. IP-WB analysis using the indicated antibodies reveals interaction of B-PES with the endogenous HSP70, but not endogenous BAK, BCL-xL, or HSC70.
Figure 2:
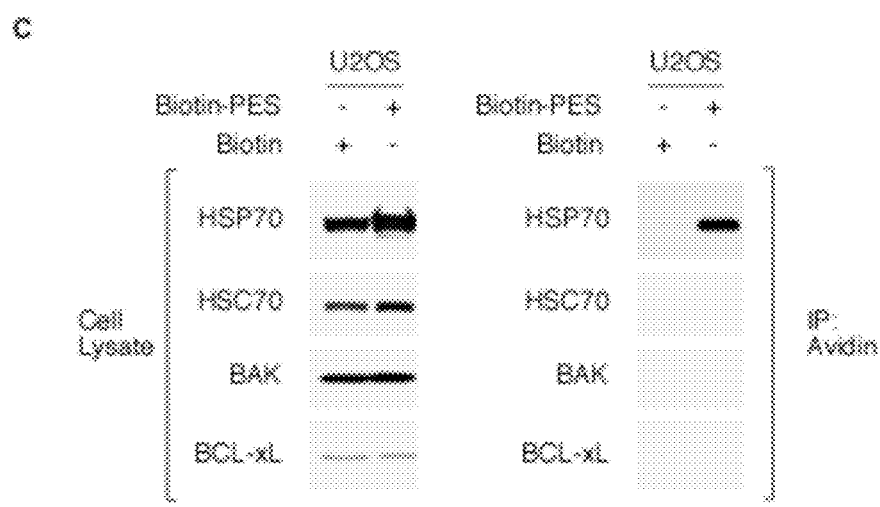
Figure 3:
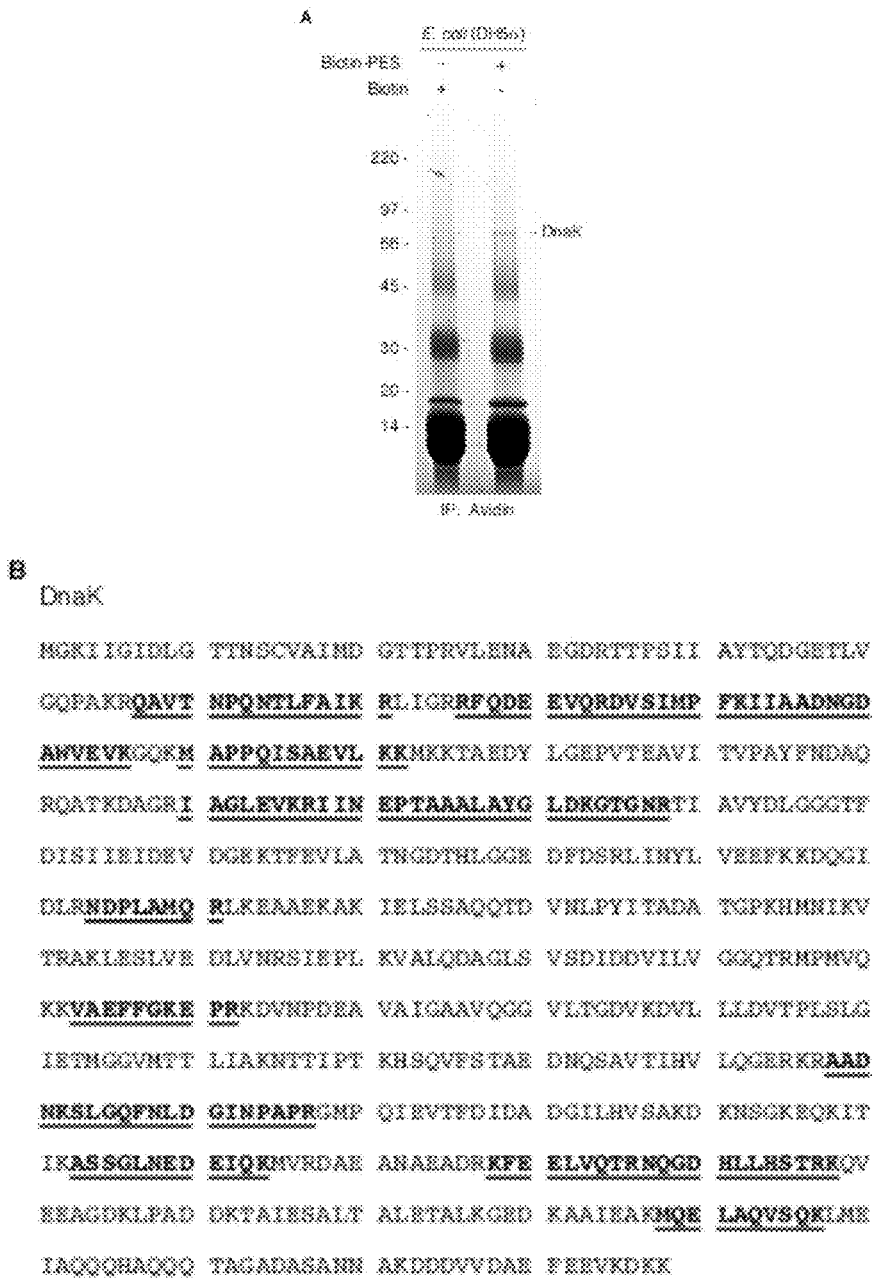
FIG. 3. PES and E. coli. (A) Identification of DnaK as Biotin-PES (B-PES) interacting protein in bacteria by liquid chromatography-tandem mass spectrometry, as described herein below. (B) The amino acid sequence of DnaK (SEQ ID NO: 7); the residues detected by mass spectrometry are shown in bold and underlined. (C) Growth curves of E. coli treated with different concentrations of PES either at 35° C. or 43° C. Since bacteria with some mutations in DnaK exhibit a thermosensitive phenotype, liquid bacterial cultures were treated with increasing concentrations of PES at temperatures of 35° C. or 43° C. Cell proliferation was inhibited in a dose-dependent fashion, especially at 43° C. (D) Bacterial morphology (phase contrast microscopy) following treatment of the cells with PES at the indicated temperatures. Note evidence of filamentation and aggregation at higher concentrations of PES, especially at 43° C.
Figure 3:
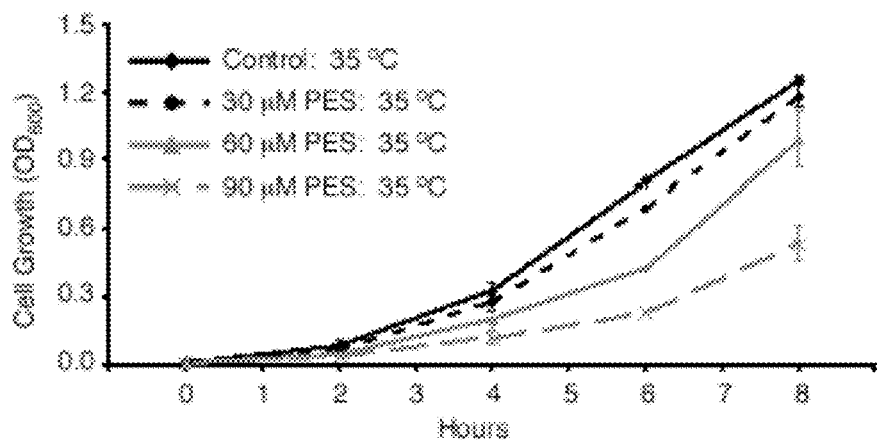
Figure 3:
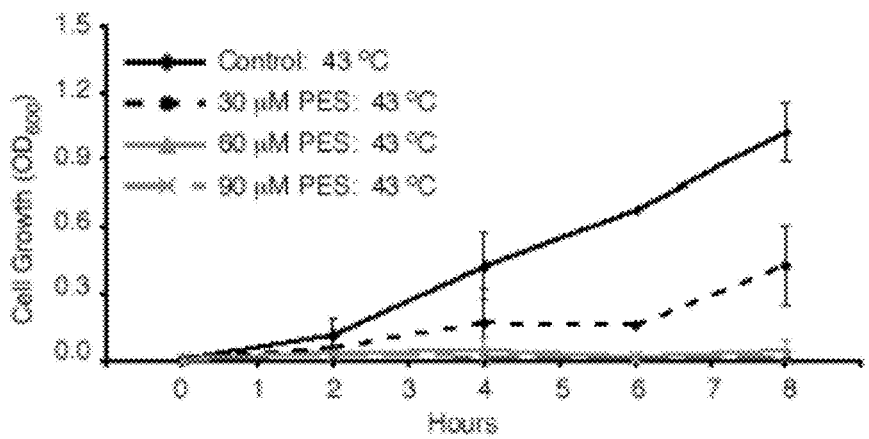
Figure 3:
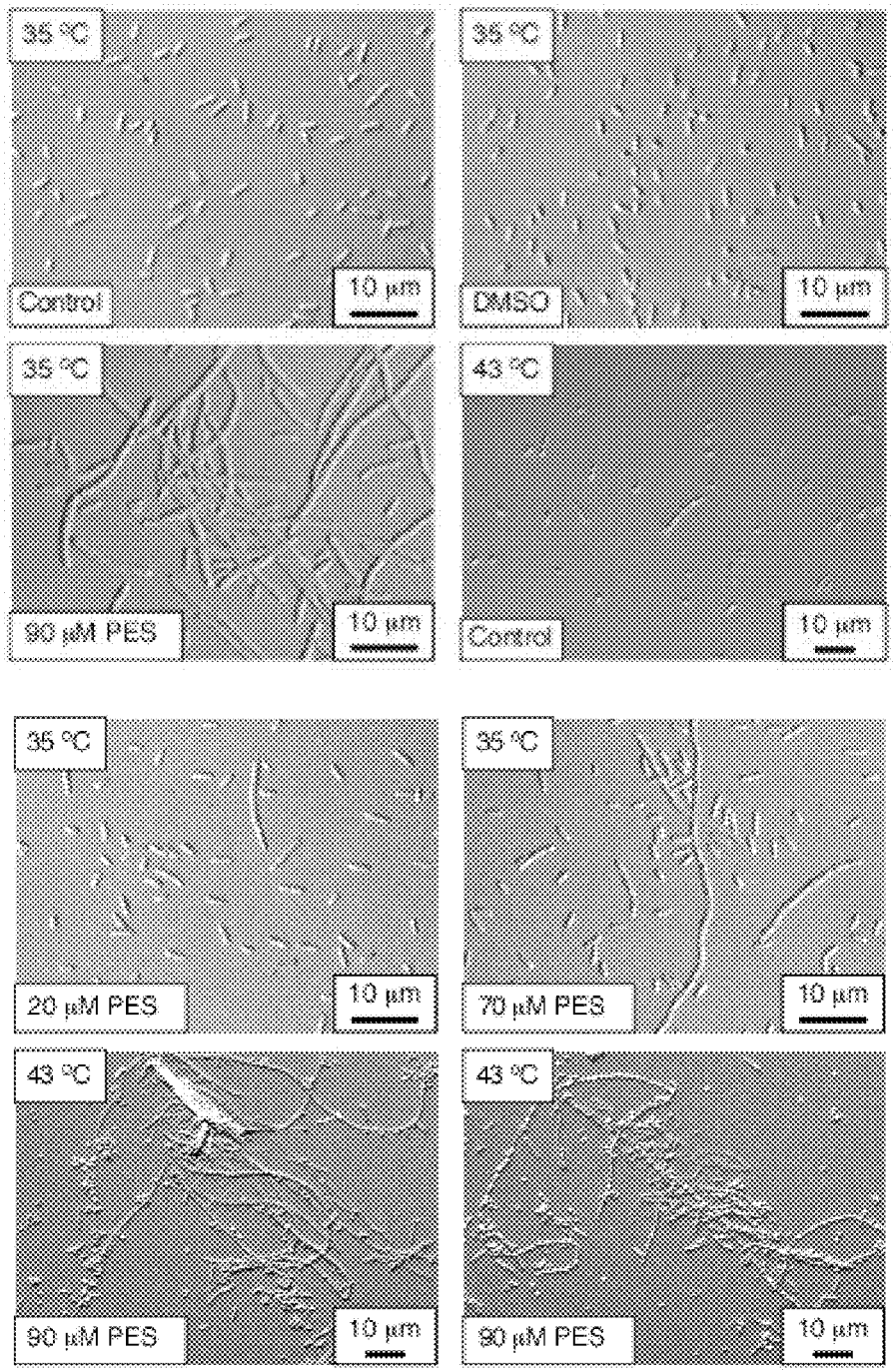
Figure 15:
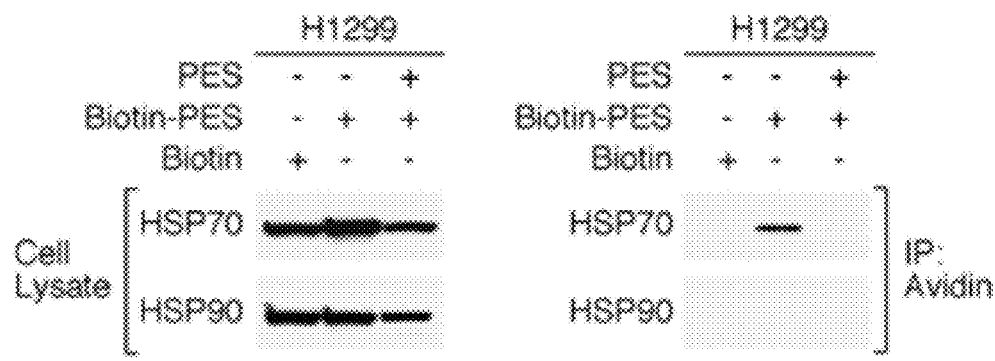
FIG. 15. Evidence supporting HSP70 as the cellular target of PES. (A) Competition studies in vivo support HSP70 as a PES target. H1299 cells were either pre-treated with DMSO or excess (25×) untagged PES for 1 h prior to the addition of 20 μM Biotin-PES (B-PES) for 5 h, and examined for the expression of proteins indicated (left). B-PES-containing complexes were captured by NeutrAvidin Resins, and immunoblotted using the indicated antibodies. Binding of HSP70 to the matrix is reduced in the presence of the non-tagged competitor PES. (B) Competition studies in vitro support HSP70 as a PES target. Purified HSP70 protein was incubated with 0.25 mM B-PES in the absence and in the presence of 0.125 mM untagged PES. IP-WB analysis reveals direct interaction between B-PES and HSP70. Pre-incubation of HSP70 protein with untagged PES reduces B-PES/HSP70 complex formation.
Figure 15:
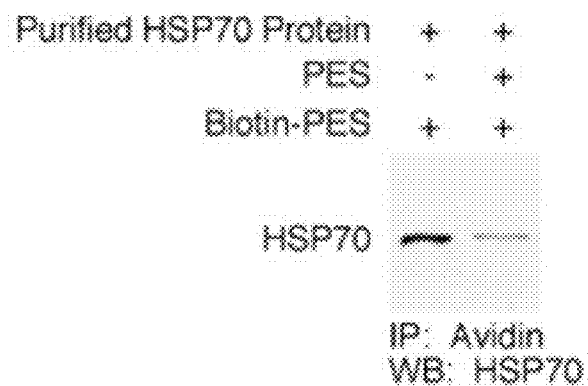

Based on the structure of PES (FIG. 2A), we used a thiol-cleavable amine-reactive reagent to synthesize a biotinylated form of the molecule (biotin-PES), as described (see Methods). Several mammalian cell lines were treated with biotin-PES, cell lysates were prepared, and biotin-PES complexes were captured using NeutrAvidin Resins. PES-interacting proteins were eluted using 100 mM DTT, which cleaves the disulfide bond in the spacer arm of the biotin attached to PES. The associated proteins were resolved by SDS-PAGE in a 4%-20% gradient gel and visualized by Coomassie staining. Results obtained using two different mammalian cell lines were consistent, and revealed a major band of about 70 kDa (FIG. 1A). The band was excised from the gel, subjected to trypsin digestion, and the resulting peptides were analyzed by liquid chromatography-tandem mass spectrometry. The results pointed to the presence of the stress-inducible HSP70 or the closely related constitutive HSC70 ("cognate" 70 kDa heat shock protein), which have peptides in common (see FIG. 2B for peptide analysis). We next carried out an analysis of PES-treated cells using antibodies specific for different HSP proteins, including the stress-inducible HSP70, HSC70, the ER-localized HSP family member GRP78 (BiP), and the 90 kDa molecular chaperone HSP90. These analyses revealed that in several cell lines Biotin-PES interacts with HSP70, but not with HSC70, GRP78, HSP90, or several other proteins (FIGS. 1B, 1C and 2C). Competition studies shown in FIG. 15 confirm that HSP70 is the cellular target of PES. Although HSC70 and HSP70 are highly homologous (FIG. 2B), they do exhibit some functional differences, in part related to different interactions with some co-chaperones (Rohde et al., 2005; Tutar et al., 2006). To complement these analyses, we confirmed that Biotin-PES interacts with in vitro translated HSP70, but not with HSP90 (FIG. 1D). Based on deletion analysis, we determined that Biotin-PES interacts with the carboxyl-terminal substrate-binding domain (amino acids 386-641), but not the amino-terminal ATPase domain (amino acids 2-385), of human HSP70 (FIG. 1E). Interestingly, we also obtained evidence that PES interacts with DnaK, the bacterial orthologue of mammalian HSP70 (FIGS. 3A and 3B). Consistent with a disrupted function of DnaK resulting from an interaction with PES, we found that this small molecule adversely affects the response of the bacteria to elevated temperatures by producing slow growth, filamentation, and reduced viability (FIGS. 3C and 3D). Notably, these are identical to the phenotypes reported for some DnaK mutants (Bukau and Walker, 1989; McCarty and Walker, 1994).

PES Interferes with the Chaperone Function of HSP70

Figure 4:
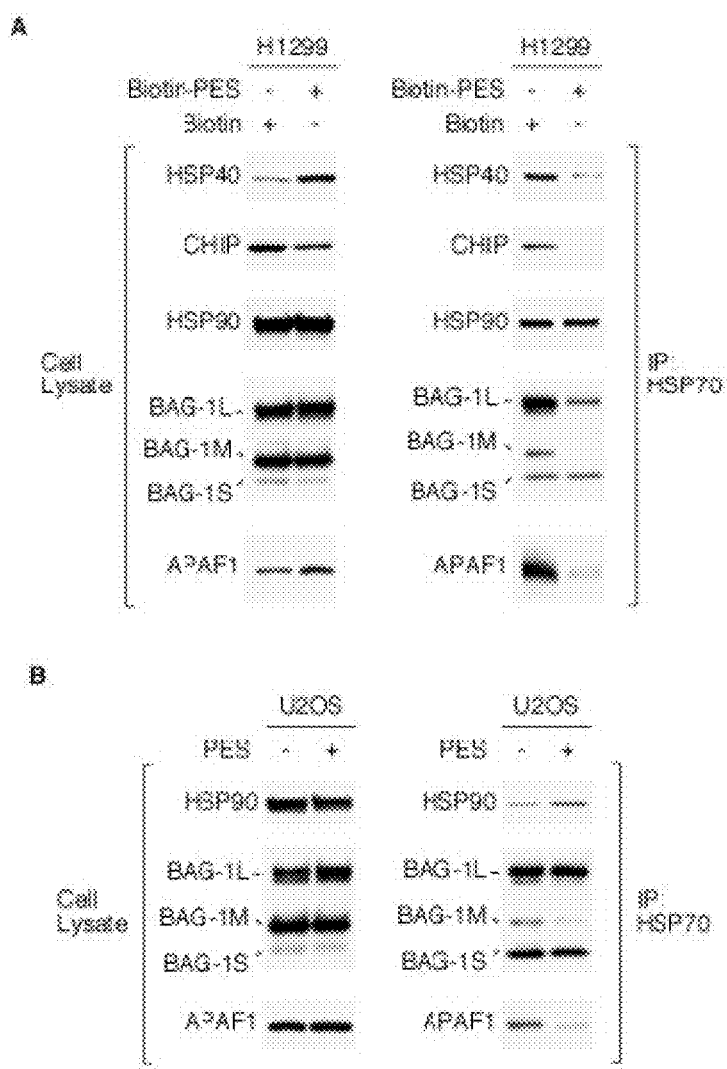
FIG. 4. PES Interferes with HSP70 Actions. (A) WCE from H1299 lung carcinoma cells, treated either with 20 µM Biotin or B-PES for 24 h, were immunoprecipitated (IP) using anti-HSP70 antibody. Western blots assessed the relative abundance of the proteins indicated (left), and co-immunoprecipitation-western (IP-WB) analysis revealed a reduced degree of interaction between HSP70 and HSP40, CHIP, BAG-1M, and APAF1 in B-PES-treated cells (right). (B) IP-WB analyses of WCE from PES-treated U2OS osteosarcoma cells reveal a lower bundance of HSP70 complexes containing BAG-1M or APAF1. (C) WCE were prepared from A875 melanoma cells that were either untreated or pretreated with PES (20 µM) for 1 h, followed by the addition of 50 µM cisplatin for 8 h. Note evidence of caspase cleavage in cisplatin-treated cells, but not in the presence of PES. IP-WB analysis reveals the presence of p53/BAK and p53/HSP70 complexes in cisplatin-treated cells (right) that are reduced following exposure to PES. (D) (left) H1299 cells were transfected with a NF-κB-dependent luciferase reporter. 24 h later, cells were either pretreated with DMSO or the indicated amount of PES for 1 h, followed by the addition of 20 ng/ml of TNFα for 5 h, as specified. Each graphical representation indicates the mean±SD of at least three independent cultures relative to control (DMSO-treated) cells. (right) H1299 cells were treated with 20 µM PES for 5.7 h, followed by treatment with 10 ng/ml TNFα for 20 min. WCE were immunoblotted for the proteins indicated.
Figure 4:
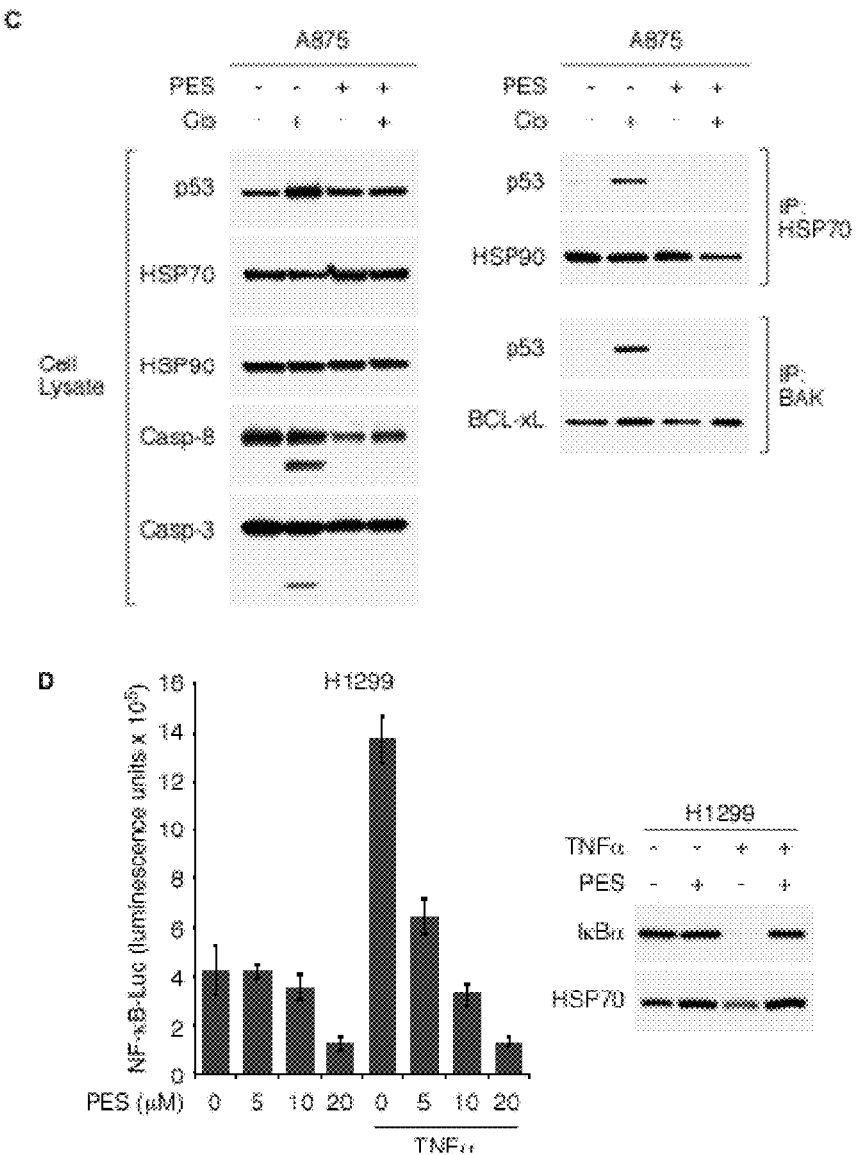

The cellular actions of HSP70 are mediated in large part by its physical association with a number of co-chaperones, including HSP40, HSP90, CHIP and BAG-1 (McDonough and Patterson, 2003; Fan et al., 2003; Wegele et al., 2004; Mayer and Bukau, 2005; Townsend et al., 2005; Kabbage and Dickman, 2008). Also, the cytoprotective role of HSP70 has been linked to its ability to modulate the conformation and actions of apoptosis-regulators like APAF1. Thus, we used immunoprecipitation-western blot analysis to determine if PES alters the interactions between HSP70 and these proteins. Several mammalian cell lines used for these analyses generated consistent results, and representative data are presented (FIGS. 4A and 4B). When compared to controls, PES-treated cells contain less HSP70 in association with CHIP, HSP40 and APAF1. In contrast, we detected no change in the abundance of HSP70/HSP90 complexes in the presence of PES.

The co-chaperone BAG-1 has several isoforms (BAG-1L, BAG-1M, BAG-1S) that have been implicated in diverse cellular pathways, including the inhibition of stress-induced apoptosis (Townsend et al., 2005; Kabbage and Dickman, 2008). PES caused a clear decrease in the interaction between HSP70 and the BAG-1M isoform (also known as the receptor-associated protein, RAP-46). In contrast, there was no detectable change in the abundance of the HSP70/BAG-1S complex, while disruption of the HSP70/BAG-1L interaction occurred in H1299 cells, but not U2OS cells (FIGS. 4A and 4B). It should be pointed out, that the same results were obtained in our experiments whether or not PES was conjugated to Biotin (FIGS. 4A, 4B, and data not shown).

Figure 5:
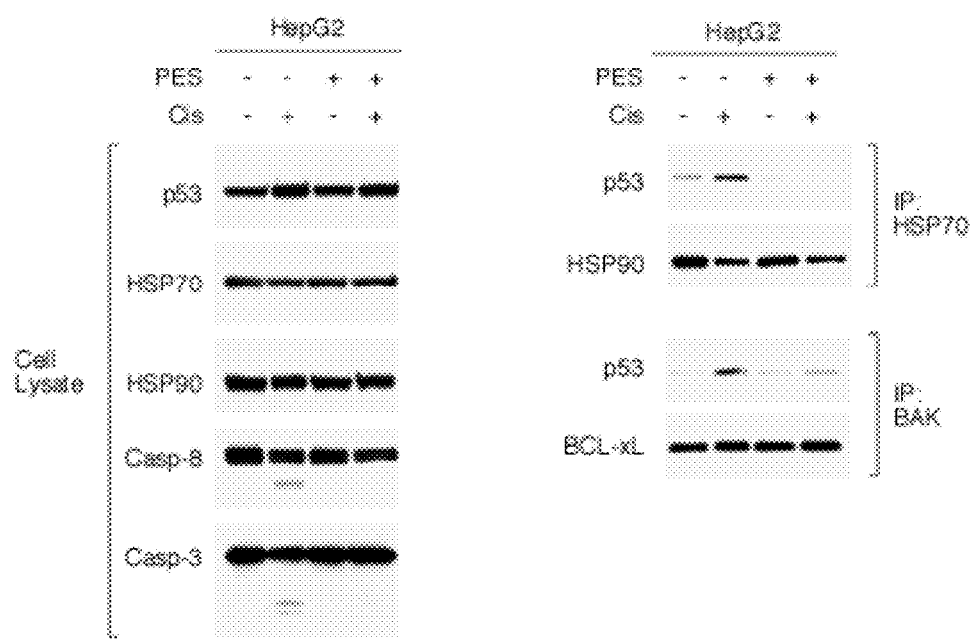
FIG. 5. PES Attenuates a p53/BAK Interaction and Inhibits Caspase Activation. Whole cell extracts (WCE) prepared from HepG2 human hepatoma cells that were either untreated or pretreated with PES (20 µM) for 1 h, followed by the addition of 50 µM cisplatin for 14 h. Note evidence of caspase cleavage in cisplatin-treated cells, but not in the presence of PES. Extracts were immunoprecipitated with anti-HSP70 or anti-BAK antibody, and blotted with anti-p53, anti52 BCL-xL, or anti-HSP90, as indicated. The data provide evidence that PES inhibits the interaction of p53 with both HSP70 and BAK.

It previously has been reported that wt p53 can be found in a complex with HSP70 under some stress conditions, such as following heat shock or UV-irradiation of cultured tumor cells (Matsumoto et al., 1994; Chen et al., 1999). In light of these observations and data that PES antagonizes p53 mitochondrial localization (Strom et al., 2006; Leu and George, 2007), we tested the hypothesis that PES alters the HSP70/p53 association. For these analyses, we treated A875 melanoma cells and HepG2 hepatoma cells with cisplatin. As previously demonstrated (Leu and George, 2007), cisplatin (50 µM) promotes p53 mitochondrial localization, where it interacts with mitochondrial BAK, and promotes caspase cleavage, as revealed by analysis of caspase-3 and caspase-8 (FIGS. 4C and 5). Under these conditions, we detected a fraction of the stress-activated p53 in a complex with HSP70 (FIGS. 4C and 5). In contrast, protein complexes containing p53 and either BAK or HSP70 were not observed in cells treated with PES or with cisplatin and PES; for the latter, there was a concomitant reduction in the appearance of caspase cleavage products (FIGS. 4C and 5). In contrast to the altered HSP70/p53 interaction in response to PES, there was no detectable change in the association between HSP70 and HSP90 or between BAK and BCL-xL (FIGS. 4C and 5).

The nuclear transcription factor NF-κB is an important regulator of cellular responses to stress, and contributes to pathological processes such as inflammation and tumor cell survival. Through mechanisms that are not fully characterized, HSP70 has been implicated as interacting with regulatory components of NF-κB signaling pathways (Salminen et al., 2008). In initial studies, we have found that PES inhibited NF-κB activation along with the concomitant turnover of the NF-κB inhibitory protein IκBα, that is normally stimulated by tumor necrosis factor-alpha (TNFα). PES also inhibited unstimulated NF-κB activity in a dose-dependent manner (FIG. 4D). These observations, together with data described below, indicate that disruption of HSP70 functions by PES interferes with a number of cell survival and signaling pathways.

Figure 16:
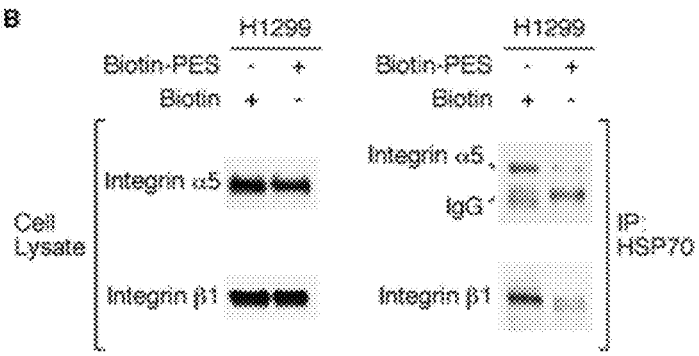
FIG. 16. PES reduces viability of cultured human tumor cells and interferes with HSP70 chaperone function. (A) The indicated cell lines were treated with different concentrations of PES for 72 h. Viability assays using MTT reveal reduction in cell viability in the presence of PES. Values shown are normalized to the viability of the control (DMSO-treated) cells. (B) Whole cell extracts from H1299 human lung carcinoma cells, treated either with 20 μM Biotin or B-PES for 24 h, were immunoprecipitated (IP) using anti-HSP70 antibody. Western blots assessed the relative abundance of the proteins indicated (left), and co-immunoprecipitation-western (IP-WB) analysis revealed a reduced degree of interaction between HSP70 and Integrin α5 as well as Integrin β1 in B-PES-treated cells (right). (C) Whole cell extracts prepared from human 293T cells containing Simian Virus 40 transforming antigen (SV40 T Ag); cells were either untreated or treated with PES (20 μM) for 7 h or 24 h. Extracts were immunoprecipitated with anti-HSP70. The data provide evidence that PES interferes with the interaction between HSP70 and the viral T Ag protein.
Figure 16:
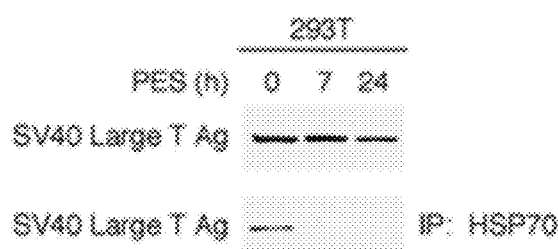

Additional experiments to assess PES effects on HSP70 chaperone function demonstrate that PES was effective at killing H1299 lung carcinoma cells and also reduced HSP70 and integrin α5 and integin β1 interactions in these cells (FIG. 16B). PES also interfered with HSP70 and viral T antigen interactions in 293 cells harboring Simian virus 40 transforming T antigen (FIG. 16C).

PES Induces Cell Death in the Absence of Caspase Activation

Figure 6:
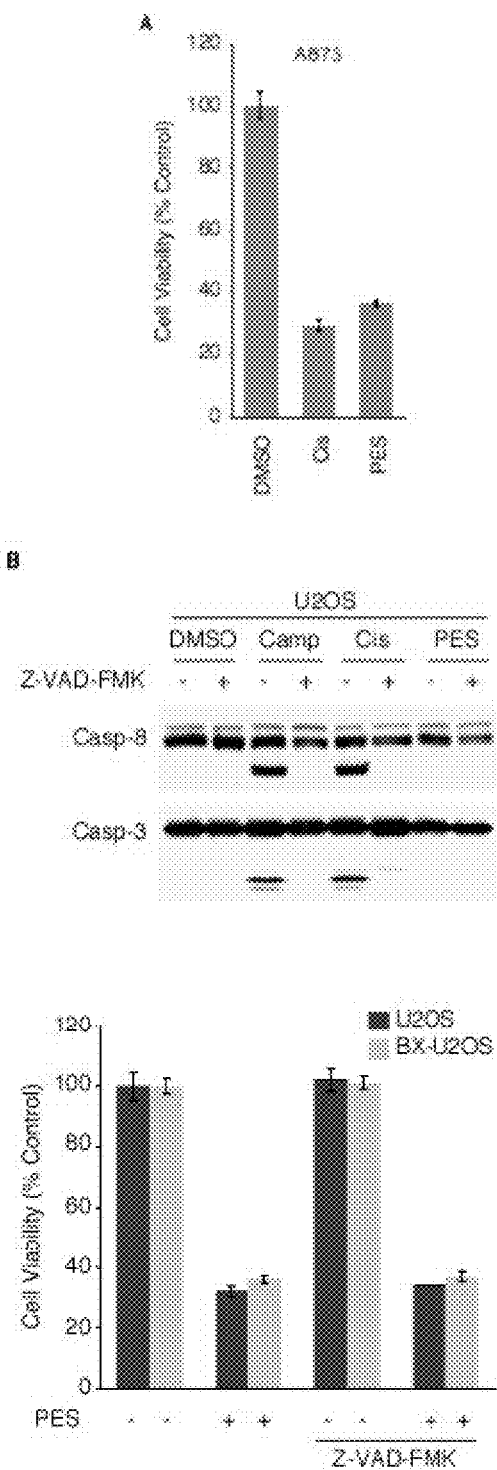
FIG. 6. PES Reduces Viability of Tumor Cells. (A) MTT assays of A875 cells treated with DMSO, 20 µM PES, or 50 µM cisplatin for 24 h. Each graphical representation indicates the mean±SD of at least three independent cultures relative to control (DMSO-treated) cells. (B) (Top) WCE were prepared from U2OS osteosarcoma cells that were either untreated or pretreated with Z-VAD-FMK (20 µM) for 1 h, followed by the addition of 5 µM camptothecin (Camp), 16 µg/ml Cisplatin (Cis), or 20 µM PES for 6 h. Note evidence of caspase cleavage in cisplatin- or camptothecin-treated cells, but not in the presence of PES or Z-VAD-FMK. (Bottom) The indicated cell lines were either untreated or pretreated with Z-VAD-FMK (20 µM) for 1 h, followed by the addition of DMSO or 20 µM PES for 24 h. Cell viability was determined by MTT assays. Results shown are the mean of at least three independent experiments. (C) The indicated cell lines were treated with the indicated concentrations of PES for either 24 h (top) or for 48 h (middle and bottom). Representative MTT assays indicate cell viability in human cell lines, including non-transformed human WI38 fibroblasts, as well as several tumor cell lines with wild type (wt) p53 (U2OS, BX-U2OS, MCF7, CaPan2), or with mutant/deleted p53 (SKBR3, MDA-MB-468, MDA-MB-231, CaPan1, MiaPaCa2, and Panc1). Four independent cultures were assayed for each treatment and DMSO treated cells were used as internal controls. Values shown are normalized to the viability of the control (DMSO-treated) cells. Error bars represent standard deviation (SD).
Figure 6:
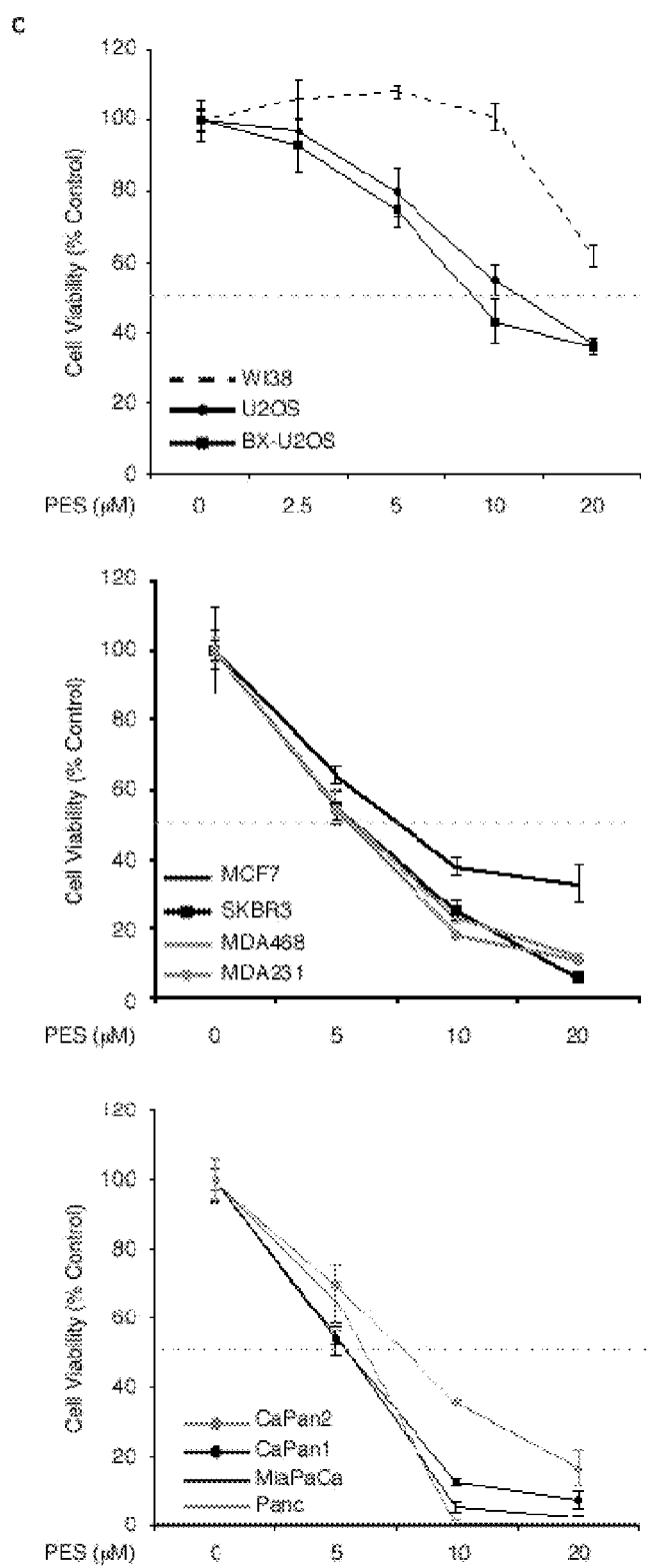

Caspases are critical cellular effectors of apoptosis. As shown, caspase activation was observed following treatment of the cells with a concentration of cisplatin (50 µM) that produced about 50% cytotoxicity (FIGS. 4C, 5 and 6A). Interestingly, while exposure to PES (20 µM) caused a greater than 50% loss of cell viability in all of the tumor cell lines we examined (FIGS. 6A-6C), this was not accompanied by cleavage of caspase-3, caspase-8, or PARP, based on western blot analyses (FIGS. 4C, 6B and 5; Leu and George, 2007). In fact, co-treatment of cells with PES together with cisplatin effectively inhibited the appearance of these caspase-cleavage products (FIGS. 4C and 5; Leu and George, 2007). Moreover, although the broad-spectrum caspase inhibitor Z-VAD-FMK inhibited cisplatin- as well as camptothecin-mediated caspase cleavage, it did not alter PES-mediated loss of cell viability (FIG. 6B). Together, these results indicate that PES leads to a loss of cell viability in a manner that is not dependent on caspase activation, and indeed that PES inhibits caspase activation. This is consistent with the identification of PES as a small molecule inhibitor of p53-mediated apoptosis (Strom et al., 2006).

We analyzed several tumor cell lines of different histologic type and found that PES treatment leads to a dose-dependent loss of cell viability for all of the tumor cell lines we examined (FIGS. 6A-6C and 16A). In contrast, non-transformed WI38 human fetal lung fibroblasts exhibit no decrease in cell viability (FIG. 3C), except at the highest concentration of PES tested (20 µM). These results suggest a differential sensitivity to PES between non-tumor cells and tumor cells. Tumor cells that lack a functioning p53 tumor suppressor protein or that overexpress antiapoptotic members of the BCL2 family are known to exhibit resistance to many chemotherapeutic agents. It is of interest, therefore, that the loss of cell viability resulting from PES occurred in all of the tumor cell lines we examined, irrespective of the p53 status (FIGS. 6C and 16A). Additionally, the anti-apoptotic protein BCL-xL was unable to protect against a PES mediated loss of cell viability, as evidenced by the similar dose-response curves of U2OS osteosarcoma cells and a U2OS-derivative (BX-U2OS) that overexpresses BCL-xL (FIGS. 6B and 6C). These data support the conclusion that PES-mediated cytotoxicity involves a mechanism distinct from the execution of classical apoptosis.

PES Leads to Dysfunctional Autophagy and Altered Lysosome Function

Figure 7:
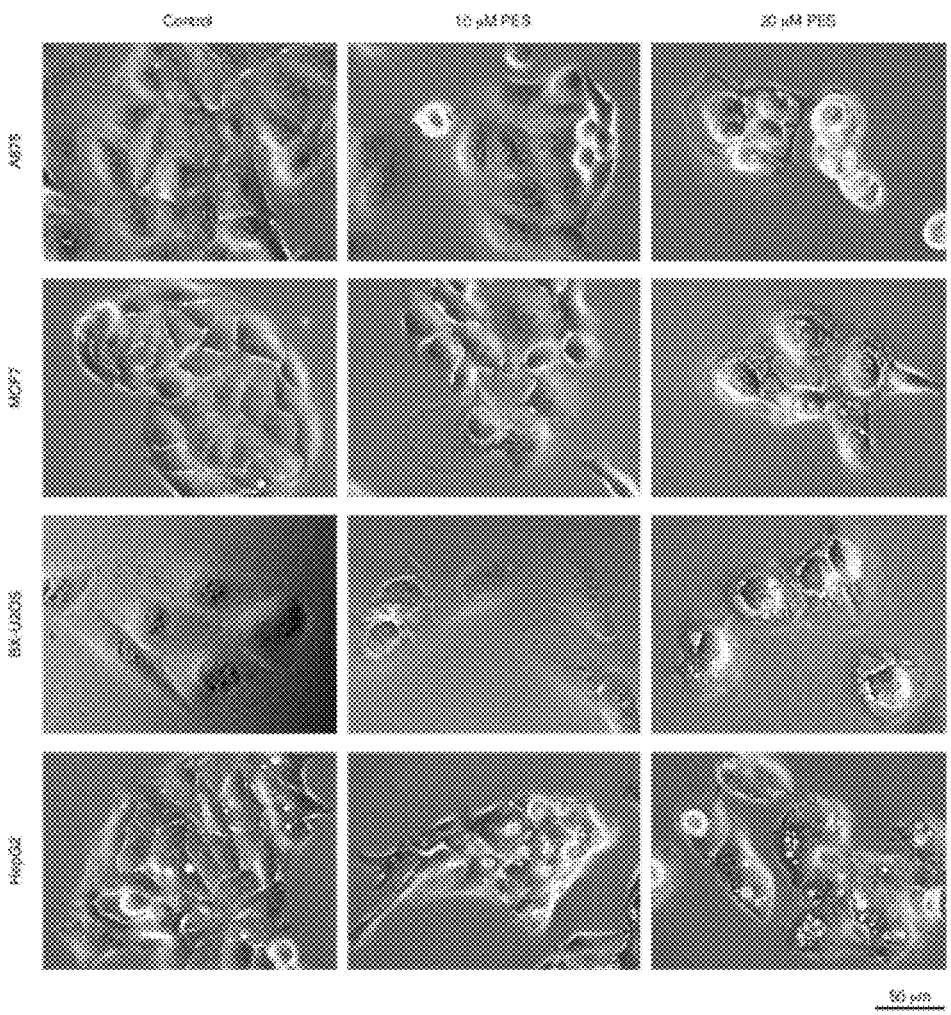
FIG. 7. PES Induces Cytoplasmic Vacuolization. Representative phase-contrast images of indicated human cell lines after 24 h of treatment using indicated amount of PES. Note the increased appearance of cytoplasmic vacuoles following increasing dosage of PES exposure.
Figure 8:
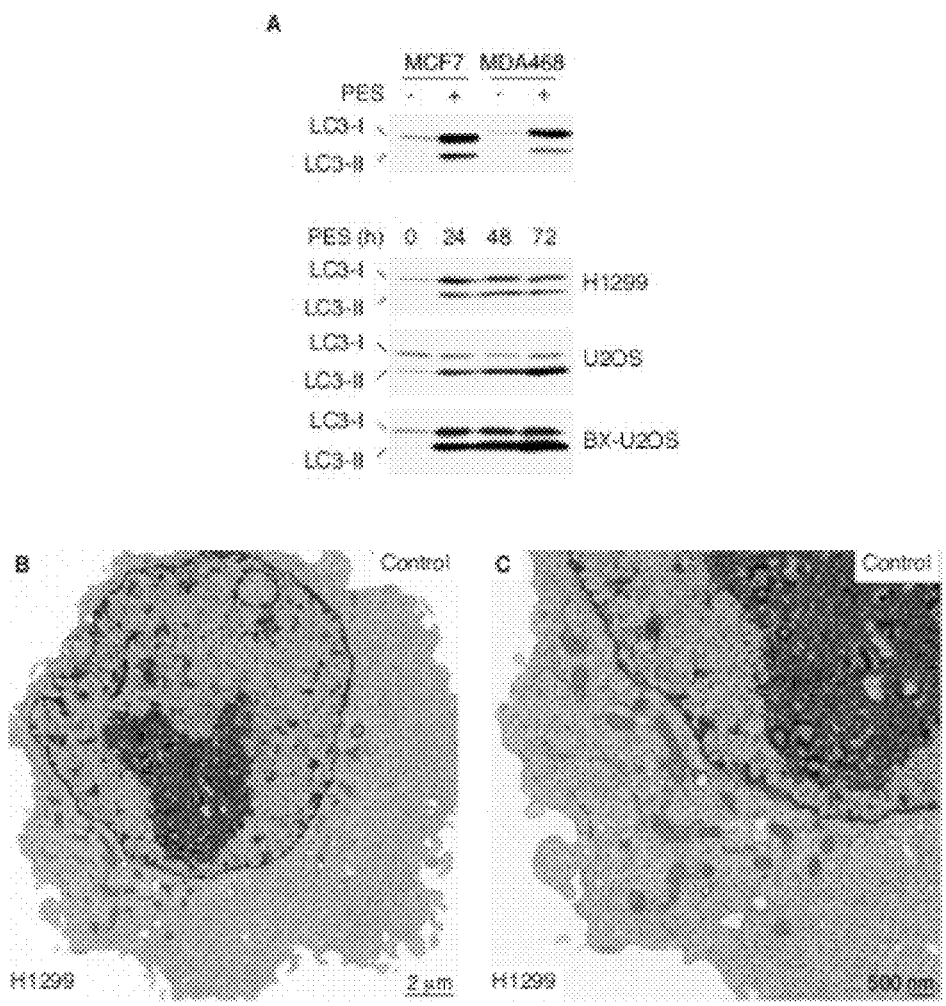
FIG. 8. PES-Treated Cells Exhibit Altered Autophagy. (A) Western blot (WB) analysis reveals increased appearance of processed LC3-II in the indicated cells following 20 µM PES treatment for the indicated times. (B-H) Electron micrographs of H1299 cells with or without PES treatment (20 µM) for 7 or 24 h. (D) Double membrane autophagic vacuoles (AV), and vacuoles within vacuoles are evident. (E and F) AVs of different sizes are evident, some containing recognizable cytoplasmic content. (G and H) Large AVs containing partially digested cytoplasmic material as well as amorphous, membranous, aggregated, or granular masses are shown. (I) The average area of autophagic vacuoles (AV) calculated with ImageJ software per cell is indicated.
Figure 8:
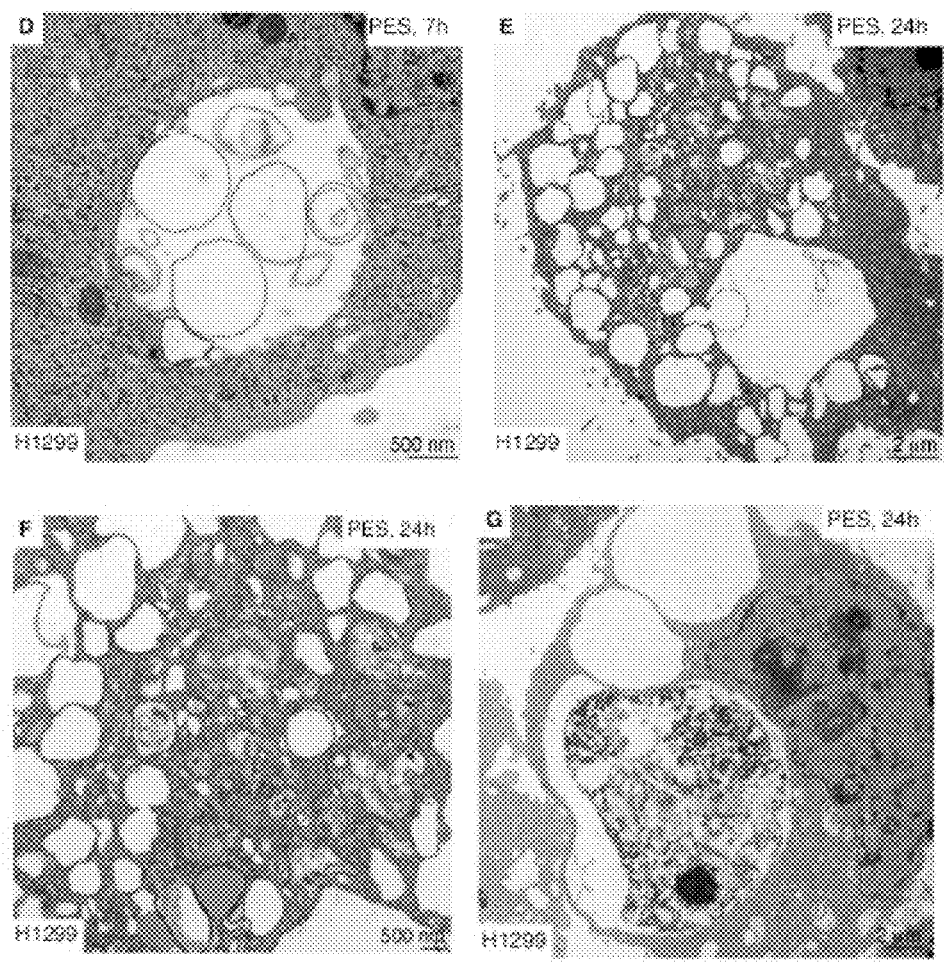
Figure 8:
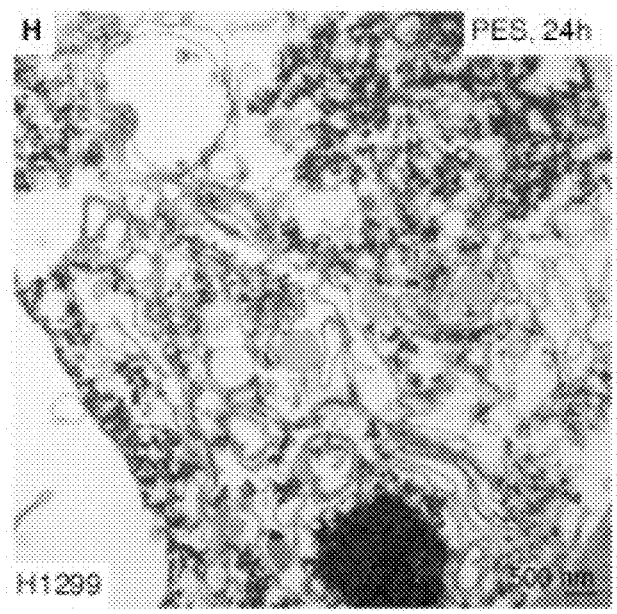
Figure 8:
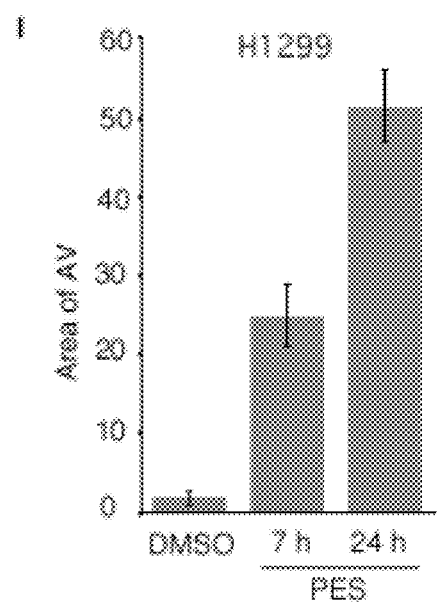
Figure 9:
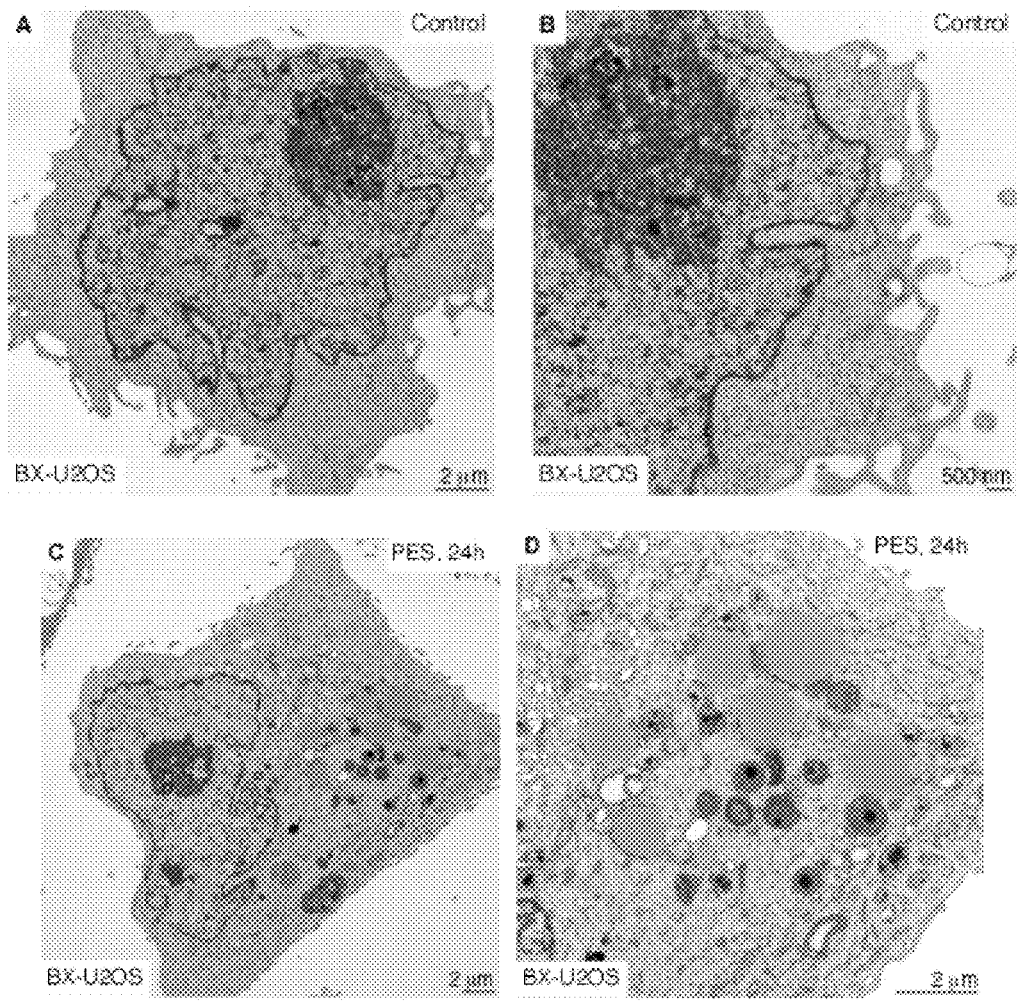
FIG. 9. PES Induces Markers of Autophagy. (A-H) Electron micrographs of BX-U2OS cells treated with or without PES (20 µM) for 24 h. (D) Double membrane autophagic vacuoles (AV) are depicted. (E) Electron dense AVs containing partially digested cytoplasmic contents are displayed. (F-H) Numerous large AVs containing partially digested cytoplasmic elements as well as amorphous, membranous, aggregated, or granular masses are shown. (I) The average area of autophagic vacuoles (AV) calculated with ImageJ software per cell is indicated.
Figure 9:
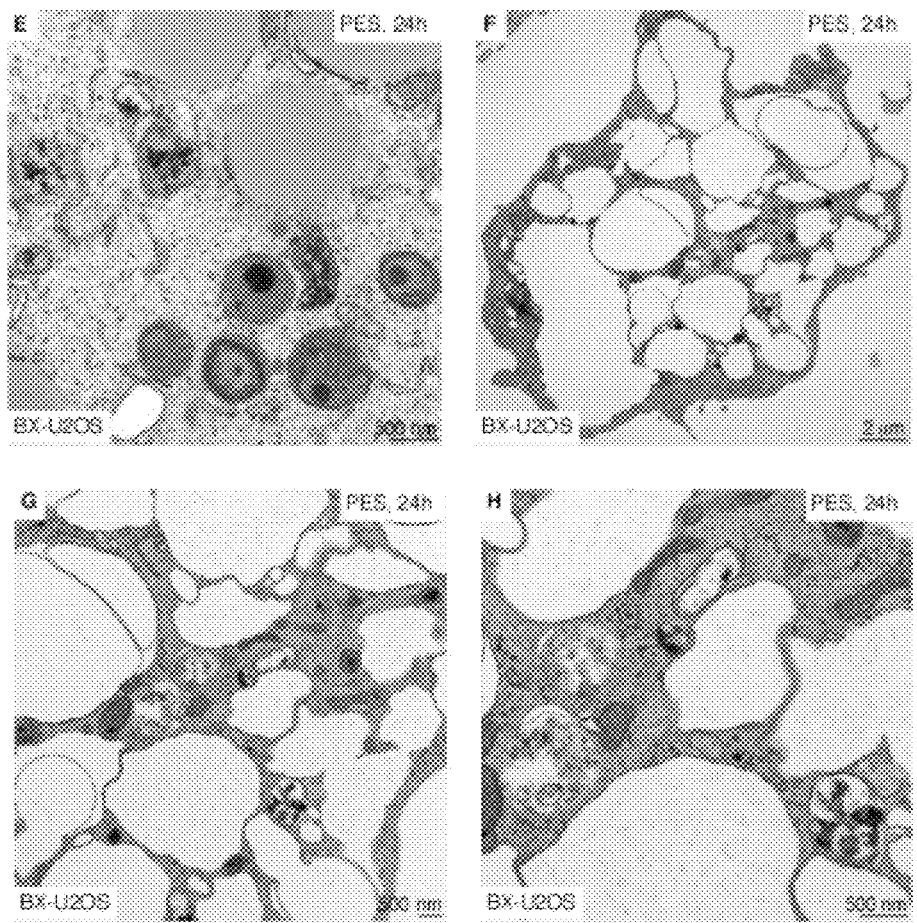
Figure 9:
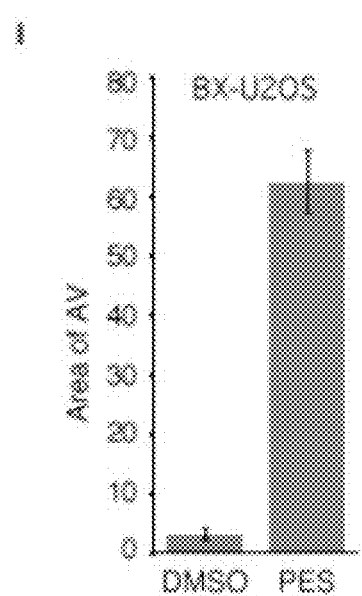

In some settings, an inhibition of caspase activation and apoptosis can induce autophagy (Debnath et al., 2005; Levine and Kroemer, 2008). Many of the PES-treated cells showed a progressive accumulation of intracytoplasmic vacuoles (FIG. 7), similar to those often observed in cells undergoing autophagy. Autophagy is an evolutionarily conserved, lysosome-dependent, bulk protein degradation pathway activated in response to starvation or stress; it allows for sustained metabolism by virtue of the digestion and recycling of long-lived proteins and cellular organelles. Mammalian cells also utilize autophagy to promote the degradation of damaged proteins, or to mediate the large-scale clearance of mis-folded proteins and aggregates (Debnath et al., 2005; Eskelinen, 2005; Levine and Kroemer, 2008; Mizushima et al., 2008). In eukaryotic cells, the process is characterized by the sequestration of portions of the cytoplasm and intracellular organelles within double-membrane autophagic vacuoles, or autophagosomes; sequestered material is targeted for degradation through fusion of autophagosomes with lysosomes or endosomes. Therefore we examined PES-treated cells for altered expression of autophagy markers, including the microtubule-associated protein-1 light-chain 3 (LC3), which is converted from the 18 kDa free form (LC3-I) to a proteolytically-processed smaller (16 kDa) form (LC3-II) during autophagy (Klionsky et al., 2008; Tasdemir et al., 2008). Based on western blot analysis, all of the PES-treated cell lines exhibited higher levels of LC3-II (FIG. 8A), consistent with an impact of PES on autophagy.

We next used a number of recommended criteria to evaluate autophagic flux in PES-treated cells (Klionsky et al., 2008; Tasdemir et al., 2008; Kaushik and Cuervo, 2009). As one approach, we used electron microscopy (EM) which confirmed that PES-treated cells exhibit a rapid and substantial increase in multiple double-membrane autophagosomes and single-membrane autophagolysosomes (FIGS. 8B-8I and FIGS. 9C-9I). Additionally, we evaluated the bulk degradation of long-lived proteins using a well-established radiolabeled-amino-acid-based assay. This approach provides a reliable indicator of autophagic flux, as it assays the end-point of autophagy (Klionsky et al., 2008; Tasdemir et al., 2008). We found that the basal degradation of long-lived proteins was significantly reduced in PES-treated cells relative to controls (FIG. 10A), consistent with an impairment of autophagic flux. The turnover of long-lived proteins is regulated in part by hydrolases present in lysosomes, hydrolytic bodies that functionally interact with the trans-Golgi network, endosomes, and autophagosomes. Lysosomes contain a number of enzymes, including cathepsin proteases, that help in the turnover of macromolecules and organelles during normal metabolism and during autophagy. To further explore the effects of PES on autophagic flux, we examined the expression of the lysosomal cysteine peptidase cathepsin L, which plays an important role in the degradation of lysosomal cargo. Like other members of this protein family, cathepsin L is synthesized as an inactive precursor that undergoes proteolytic processing to the mature, active form during transport to the acidic environment of the endosomal/lysosomal compartment through autoprocessing or cleavage by other cathepsins (Collette et al., 2004). We found that PES caused an accumulation of the precursor pro-cathepsin L and a markedly reduced abundance of the smaller, mature form of the enzyme (FIG. 10B); this points to an impaired processing of this lysosomal enzyme and impaired lysosomal function.

Figure 10:
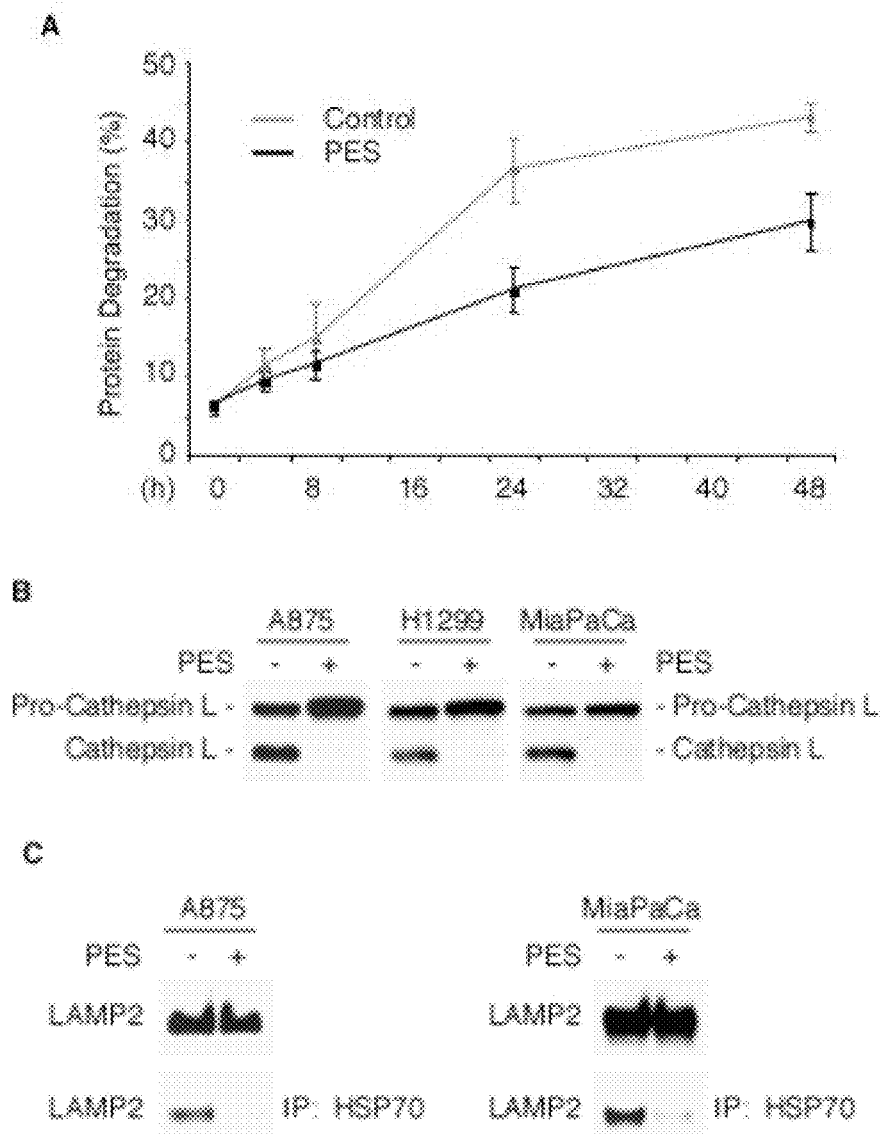
FIG. 10. PES Impairs Long-Lived Protein Degradation and Lysosomal Function. (A) Decreased degradation of long-lived proteins in U2OS cells treated with PES (20 µM) for the indicated time (black line), compared to vehicle treated cells (gray line). Data are reported in percent of protein degraded at each time point, and are the averaged data from two independent experiments done in duplicate; error bars represent standard deviation. The data were consistent in H1299 cells (data not shown). (B) Western blot (WB) analysis indicating altered processing of cathepsin L from the larger precursor form to the smaller mature form in the indicated cells following 20 µM PES treatment for 24 h. (C) IP-WB analyses of WCE from untreated or PES-treated A875 melanoma cells (left) and MiaPaCa2 pancreatic cells (right) reveal a lower abundance of HSP70 complexes containing LAMP2 following 20 µM PES exposure for 24 h (lower panels). The expression patterns of LAMP2 before and after 20 µM PES exposure for 24 h are shown on the top panel.

LAMP2 is an abundant late endosomal/lysosomal protein marker (Eskelinen, 2006) which plays an important role in chaperone-mediated autophagy and cooperates with the HSC70 and HSP70 in transporting certain substrates from the cytoplasm into lysosomes (Bandyopadhyay et al., 2008; Ryhänen et al., 2008). Given the evidence for co-localization of LAMP2 with HSP70 in lysosomes, we investigated how treatment of cells with PES might affect an interaction between these proteins. The results of immunoprecipitation-western blot analysis demonstrate that PES significantly reduced the amount of LAMP2 in a complex with HSP70 (FIG. 10C). These data, together with the evidence of altered cathepsin processing and reduced degradation of long-lived proteins in the presence of PES, further support a role for HSP70 in the optimal transport and degradation of macromolecules during macroautophagy and chaperone-mediated autophagy.

PES Promotes Oligomerization and Aggregation of p62/SQSTM1

Figure 11:
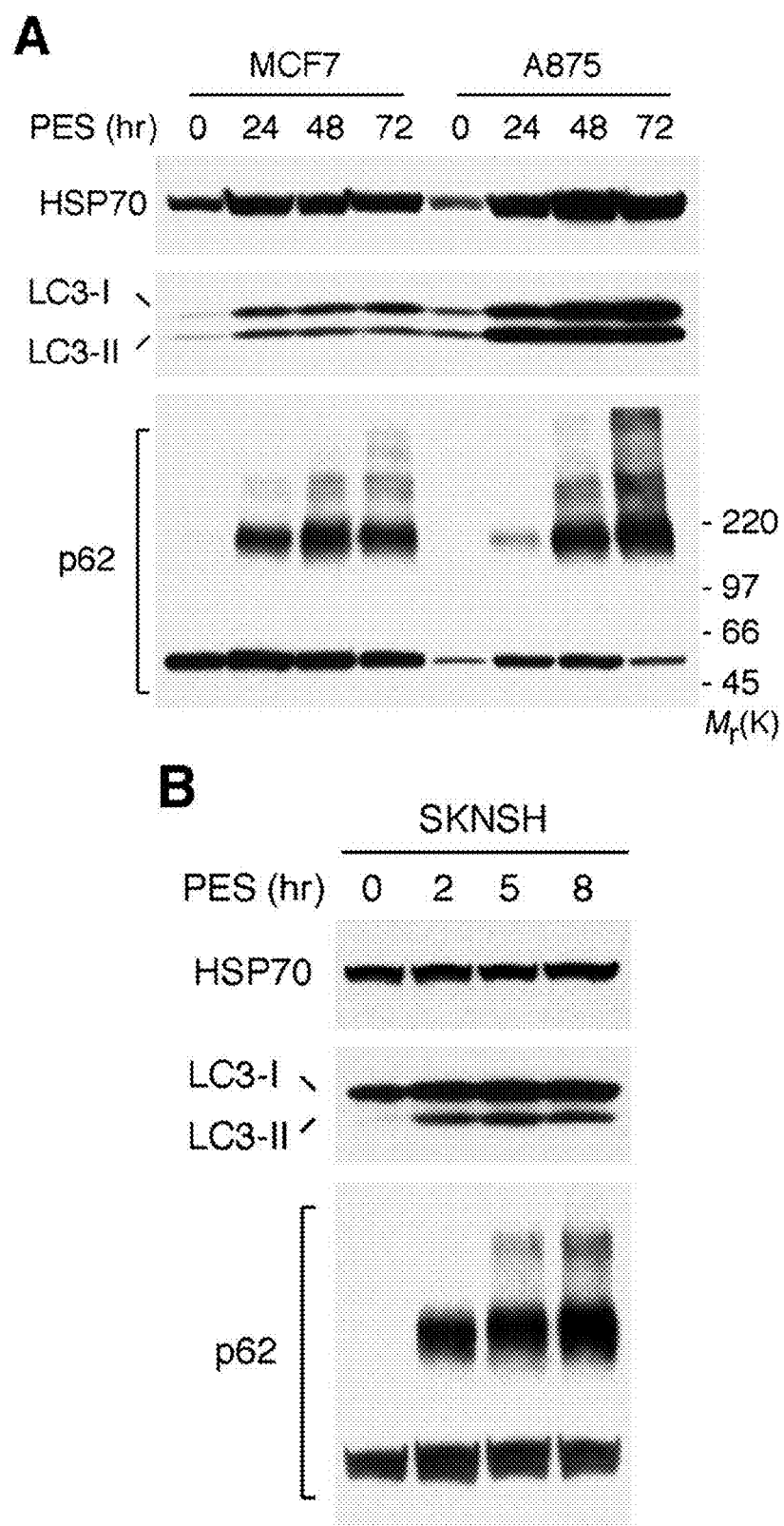
FIG. 11. PES Induces p62/SQSTM1 Oligomerization. (A and B) Western blot (WB) analysis showing increased appearance of processed LC3-II and p62/SQSTM1 oligomerization in the indicated cells following 20 µM PES treatment for the indicated time. (C) MCF7 cells were treated with indicated amount of PES for 24 h, and examined for the indicated proteins. (D) Immunostaining for p62/SQSTM1 in BX-U2OS cells, either before or following 20 µM PES treatment for 24 h. Note the appearance of p62/SQSTM1 punctae and inclusion bodies. (E) IP-WB analyses of WCE from vehicle or PES-treated MiaPaCa2 pancreatic cells (top panel) and A875 melanoma cells (lower panel). Note that LC3 binds to both the monomeric and oligomeric forms of p62/SQSTM1 following PES-exposure. (F) WI38 or H1299 cells were transfected with a negative shRNA or with HSP70 shRNAs, and examined for the indicated proteins. (G) WI38 cells were transfected with a negative shRNA or with HSP70 shRNAs. After 72 h, the cells were either untreated or treated with 10 µM PES for 24 h, and examined for the indicated proteins. (H) H1299 cells were transfected with a negative shRNA or with HSP70 shRNAs. After 48 h, the cells were either treated with DMSO or 20 µM PES for 24 h. Each graphical representation indicates the mean±SD of at least three independent cultures relative to control cells transfected with a negative shRNA and treated with DMSO. (I) MCF7 cells were treated either with 20 µM PES or 100 nM Velcade for 24 h before harvesting cells in NP40-containing lysis buffer. Lysates were centrifuged to separate the clarified lysate (detergent-soluble) and NP40-insoluble (detergent-insoluble) fractions and assayed by western blot for the proteins indicated. (J) BX-U2OS cells were treated with 20 µM PES, 50 µM chloroquine (CQ), or 15 nM 17-AAG for 24 h. Cells were harvested in 1% NP40-containing lysis buffer, fractionated into detergent-soluble and detergent-insoluble preparations, and assayed by western blot for the proteins indicated. (K) A875 cells were either pre-treated with DMSO or 20 µM PES for 1 h prior to the addition 50 µg/ml of cycloheximide (CHX) for 5 h. Note the marked reduction in PES-induced p62/SQSTM1 oligomerization in the insoluble fraction, the significant inhibition of LC3-II processing following PES and CHX co-treatment, and the obvious loss of cathepsin L expression in the presence of CHX. (L) Immunoblots showing p62/SQSTM1 oligomerization and LC3-II processing in FaDu cells in culture. (M) Nude mice bearing FaDu tumor xenografts were dosed by intratumoral administration with either vehicle for 48 h or with 40 mg/kg of PES as indicated. The dissected tumors were homogenized in 1% NP-40 containing lysis buffer, fractionated into detergent-soluble and detergent-insoluble fractions, and immunoblotted for either p62 or LC3. Representative results for two xenografts per treatment condition and time point are presented. (N) H1299 cells or IMR90 cells were treated with the specified amount of PES for 24 h and examined for the proteins indicated.
Figure 11:
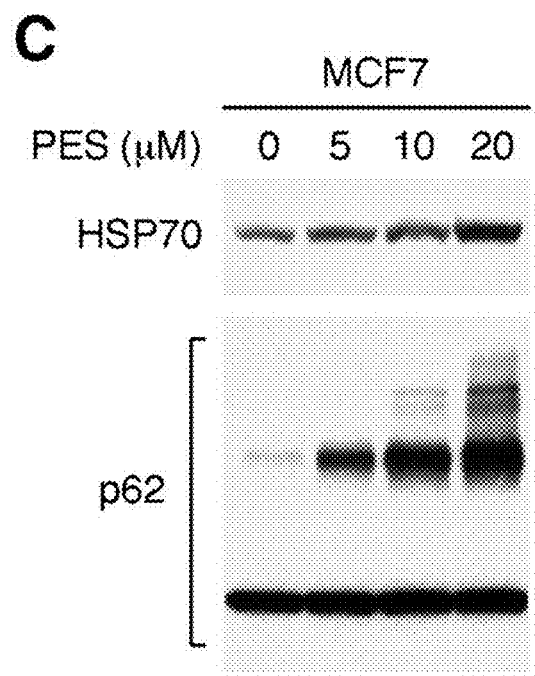
Figure 11:
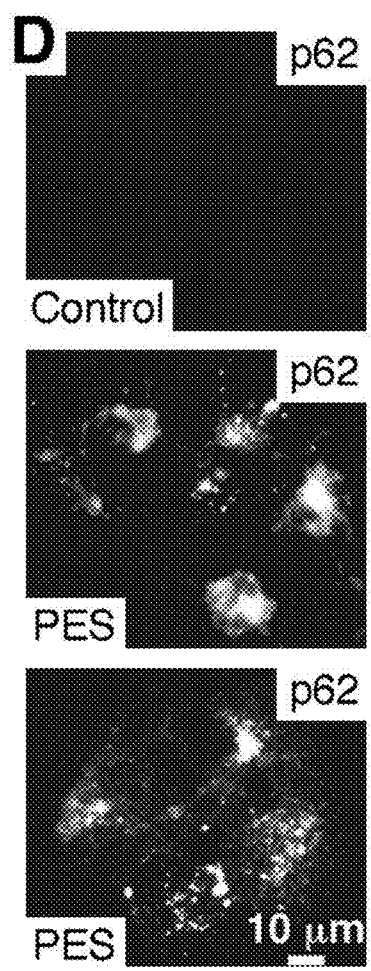
Figure 11:
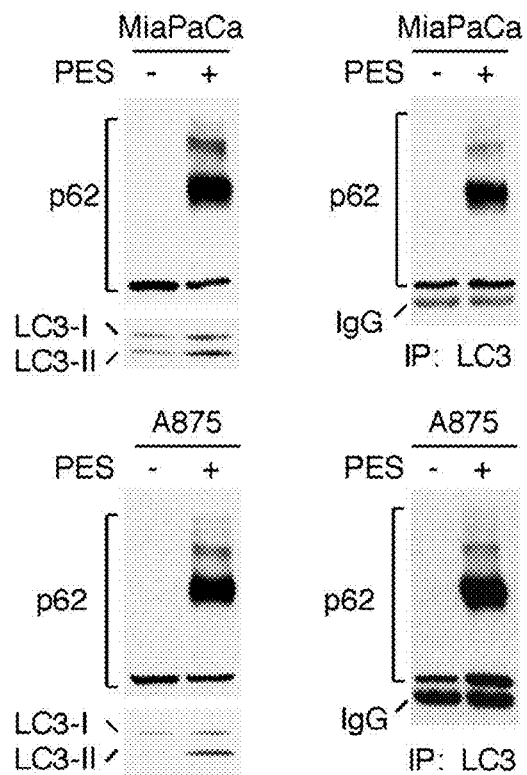
Figure 11:
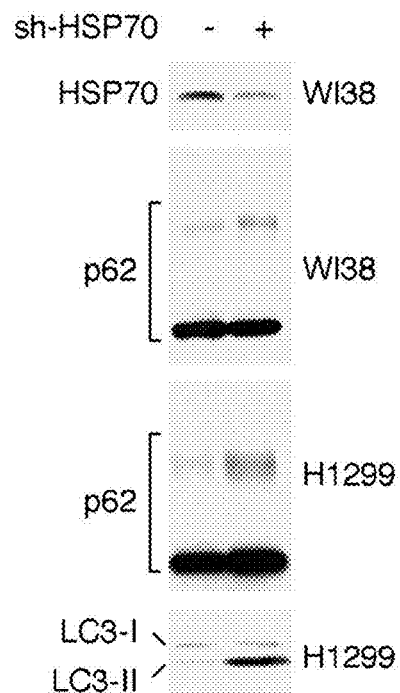
Figure 11:
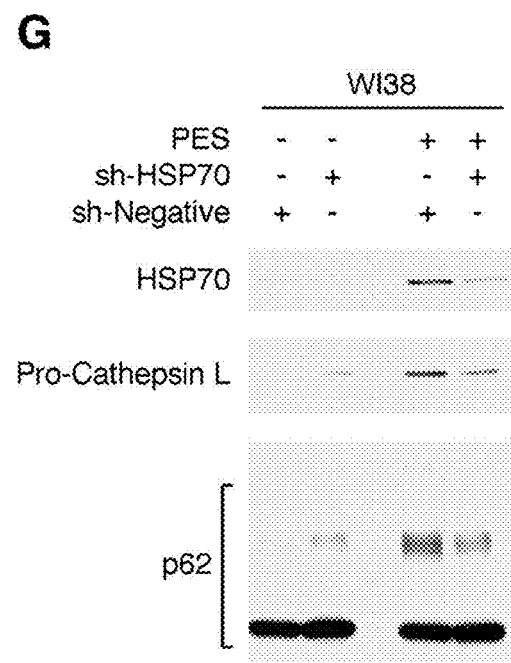
Figure 11:
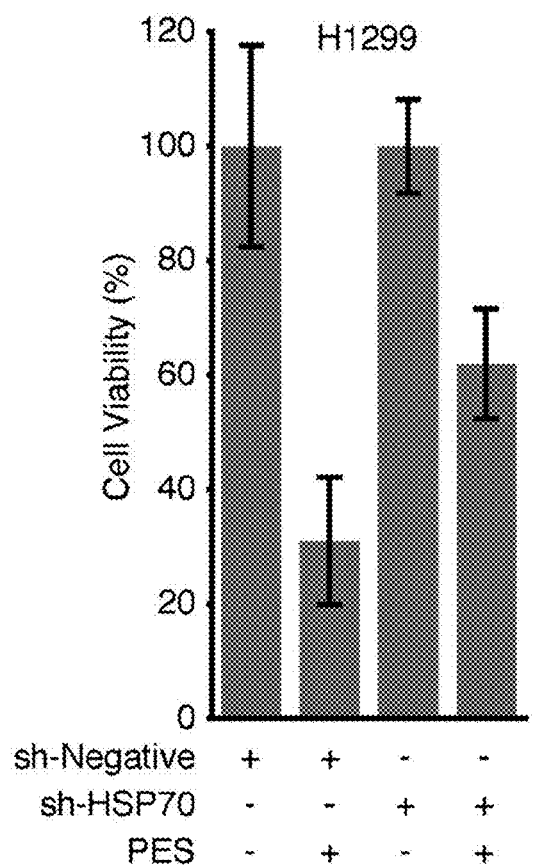
Figure 11:
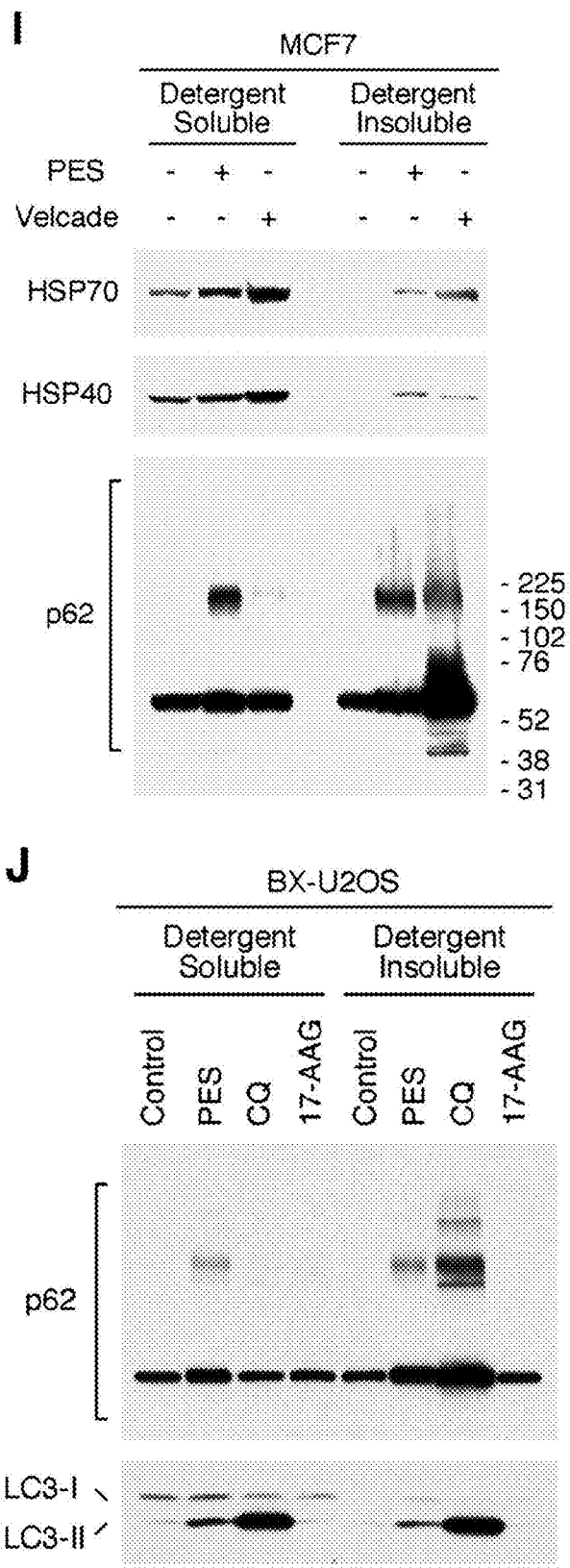
Figure 11:
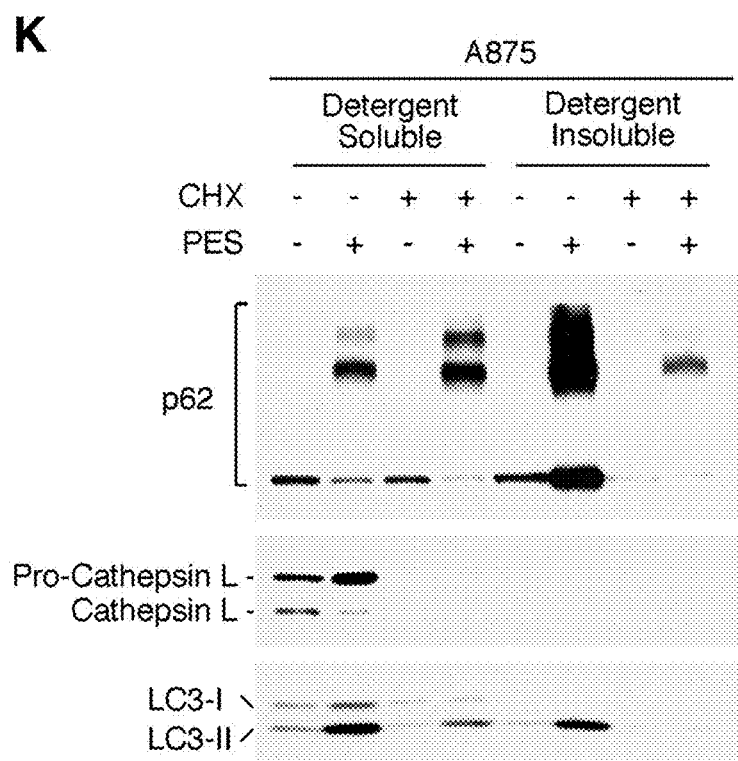
Figure 11:
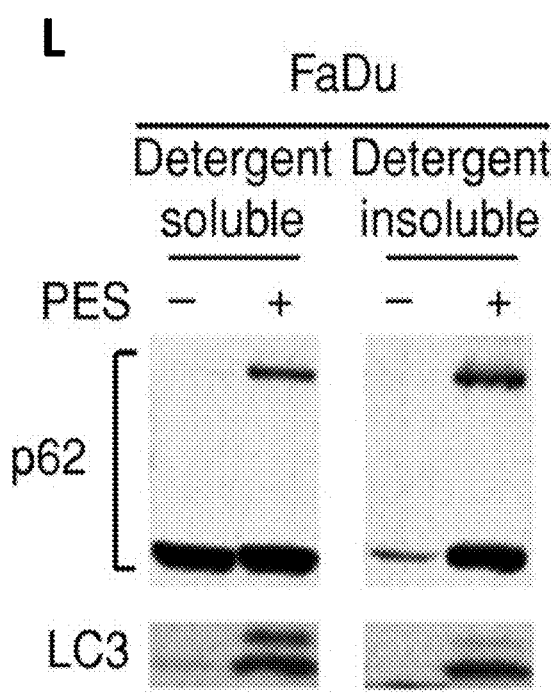
Figure 11:
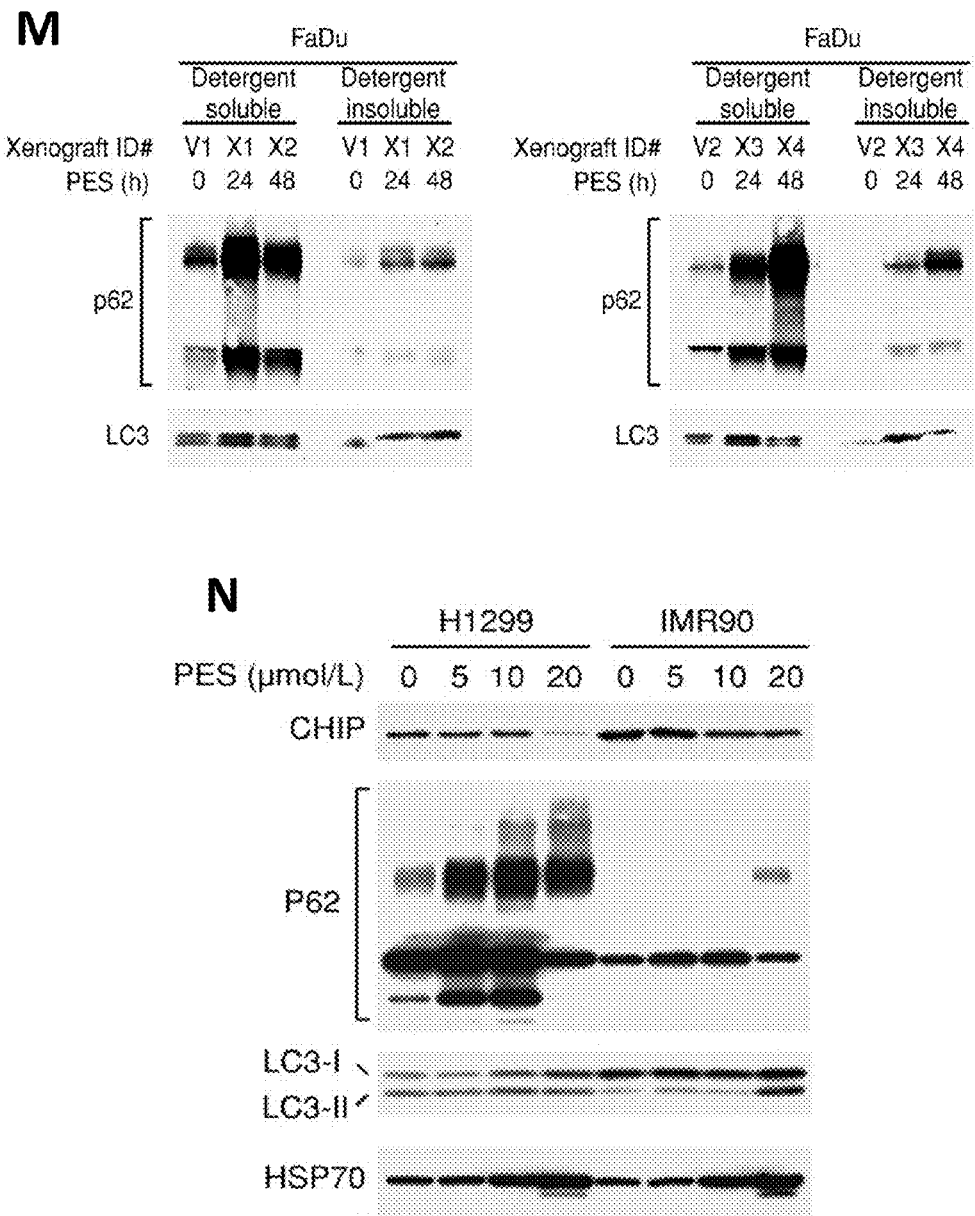

We next examined another marker of autophagy, the adaptor/scaffold protein p62/SQSTM1 (sequestosome-1). This protein is up-regulated in response to various forms of stress, and it mediates diverse cellular functions including signal transduction, receptor internalization, nuclear gene transcription, and the shuttling of some poly-ubiquitylated protein aggregates to different intracellular locations for degradation (Wooten et al., 2006; Moscat et al., 2007). The steady-state level of p62/SQSTM1 is regulated by autophagy, and an accumulation or aggregation of p62/SQSTM1 is considered a marker for inhibition of autophagy or defective autophagic degradation (Bjørkøy et al., 2005; Komatsu et al., 2007; Pankiv et al., 2007; Ichimura et al., 2008; Shvets et al., 2008). Western blot analysis for p62/SQSTM1 revealed that PES promotes an accumulation and oligomerization of p62/SQSTM1 in a time- and dose-dependent manner (FIGS. 11A-11C). Similarly, immunofluorescence-staining of PES-treated cells revealed the presence of p62/SQSTM1 punctae and aggregates (FIG. 11D), as have been seen in previous studies (Paine et al., 2005; Schvets et al., 2008; Bjørkøy et al., 2009).

Figure 12:
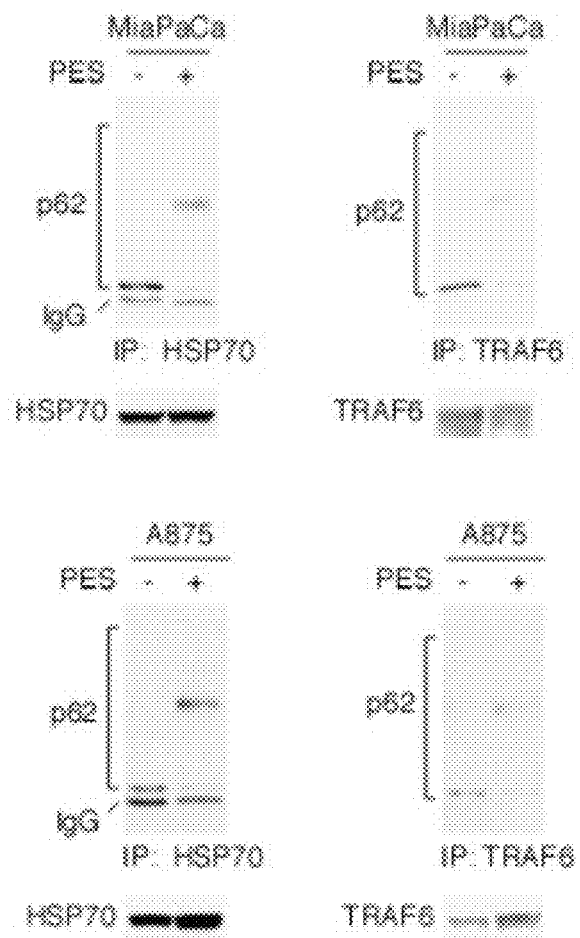
FIG. 12. PES Attenuates the Interactions between HSP70 and Monomeric p62/SQSTM1 as well as Between HSP70 and Monomeric TRAF6. IP-WB analyses of WCE from vehicle or PES-treated MiaPaCa2 pancreatic cells (top panel) and A875 melanoma cells (lower panel). Note that HSP70 binds to the oligomeric forms of p62/SQSTM1 following PES-exposure. In contrast, stable interactions between HSP70 and monomeric p62/SQSTM1 as well as between TRAF6 and monomeric p62/SQSTM1 were noted in vehicle treated cells.

An interaction between LC3 and p62/SQSTM1 proteins, which targets p62/SQSTM1 to auotophagosomes and lysosomes for degradation, is important for autophagic degradation of p62/SQSTM1 (Bjørkøy et al., 2005, 2009; Komatsu et al., 2007; Pankiv et al., 2007; Ichimura et al., 2008; Shvets et al., 2008). Therefore, we were interested in determining if the interaction between these two proteins would be modified by PES. Immunoprecipitation-western blot analysis revealed that PES enhanced the interaction between LC3 and both monomeric and oligomeric forms of p62/SQSTM1 (FIG. 11E). This observation is consistent with previous results suggesting that p62/SQSTM1 oligomerization is important for its interactions with LC3, and that p62/SQSTM1 oligomerization contributes to the formation of inclusion bodies that reside in the cytosol or within detergent-insoluble structures (Bjørkøy et al., 2005, 2009; Komatsu et al., 2007; Pankiv et al., 2007; Ichimura et al., 2008; Schvets et al., 2008). In contrast, PES attenuated the interaction between the monomeric form of p62/SQSTM1 and HSP70 as well as between the monomeric form of p62/SQSTM1 and TRAF6 (FIG. 12), which are known to interact (Pridgeon et al., 2003; Chen et al., 2006; Duran et al, 2008).

To determine whether the cytotoxicity of PES involved its association with HSP70, we next chose to reduce HSP70 expression using shRNA and to measure the effects on cell viability and autophagy. This analysis revealed that silencing of HSP70, like PES, resulted in increased levels of p62/SQSTM1 and LC3-II (FIGS. 11F and 11G). Notably, silencing of HSP70 rescued PES-induced cell death (FIG. 11H). These data support the premise that HSP70 is a critical target of PES-mediated cytotoxicity.

Figure 14:
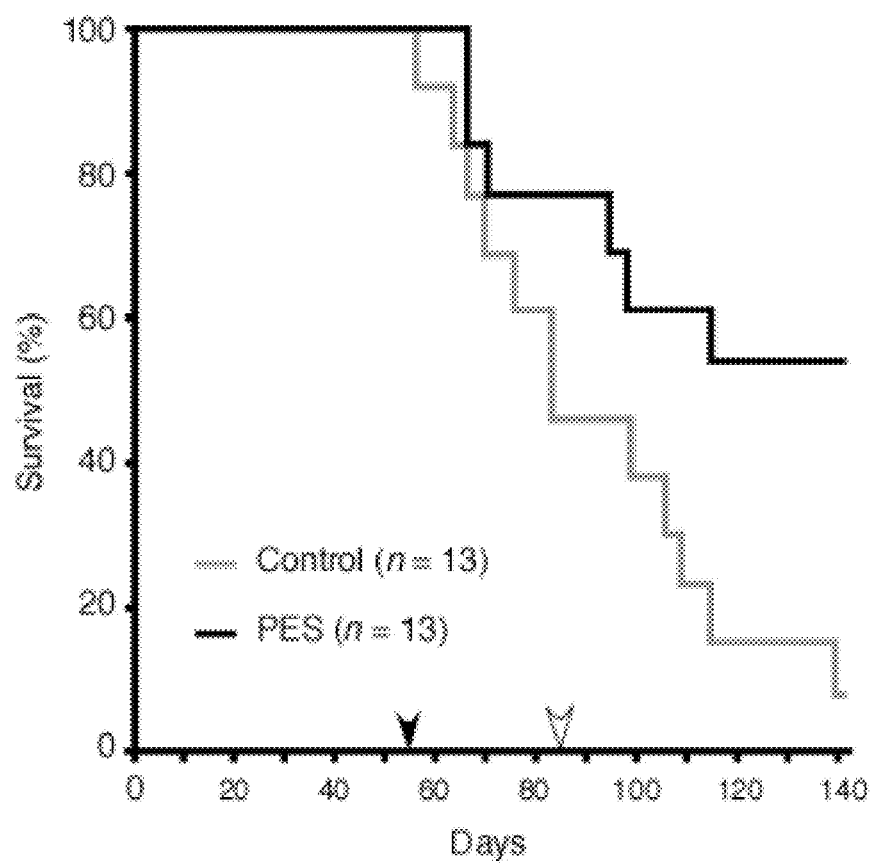
FIG. 14. PES Prevents Myc-Induced Lymphomagenesis and Prolongs the Survival of Eμ-Myc Transgenic Mice. Beginning at 8 weeks of age, Eμ-Myc transgenic mice were treated either with vehicle or 40 mg/kg PES intra-peritoneally every 5 days for a total of 30 days (n=13 for each group). The black arrow indicates the first day of treatment (day 56), and the open arrow indicates the final day of treatment (day 86). Note that PES-administration increased the overall mean survival time from about 80 days in vehicle treated animals to >140 days in PES-treated cohorts.

Using the Eμ-Myc mouse model of B-cell lymphoma, we previously reported that PES treatment effectively suppresses tumor development in vivo (Leu, et al. 2009). Briefly, we utilized a transgenic Eμ-Myc mouse model of lymphomagenesis. Beginning at 8 weeks of age, Eμ-Myc mice were treated intra-peritoneally (i.p.) once every five days with PES (40 mg/kg for 30 days), and the effects on lymphoma development and survival were determined. As shown in FIG. 14, PES-treatment markedly impaired tumor development in this mouse model of human Burkitt lymphoma, significantly increasing the overall mean survival time in the PES-treated animals (p<0.02, Mantel Cox test). Taken together, these data suggest that PES is an effective agent in the treatment of certain forms of cancer.

To assess whether PES administration leads to impaired autophagy in vivo, nude mice bearing a human head and neck cancer (FaDu) xenograft were utilized. When tumors reached a palpable size (~5-7 mm), they were treated with PES and then harvested 24 or 48 hr later. Tumor lysates were separated into detergent-soluble and detergent-insoluble fractions, and these were examined by western blot analysis for p62/SQSTM1 and LC3 expression. Several lines of evidence presented here and previously (Leu et al. 2009) indicate that an accumulation and oligomerization of p62/SQSTM1 represents a sensitive molecular signature for PES-mediated HSP70 inhibition and, thus, may serve as a potential biomarker of PES efficacy in vivo. Similar to results obtained with cultured FaDu cells (FIG. 11L), western blot analysis of the tumor xenografts revealed increased p62/SQSMT1 abundance and oligomerization in both detergent-soluble and -insoluble fractions at both 24 and 48 hr following PES administration (FIG. 11M). The western blots also provided evidence of accumulated LC3 in the detergent-insoluble fractions in the PES-treated tumors. Thus, a major biological effect of PES treatment in cultured tumor cells is recapitulated in vivo. Together, these results help lay the foundation for ongoing development of PES derivatives and other HSP70 inhibitors for clinical use.

Figure 13:
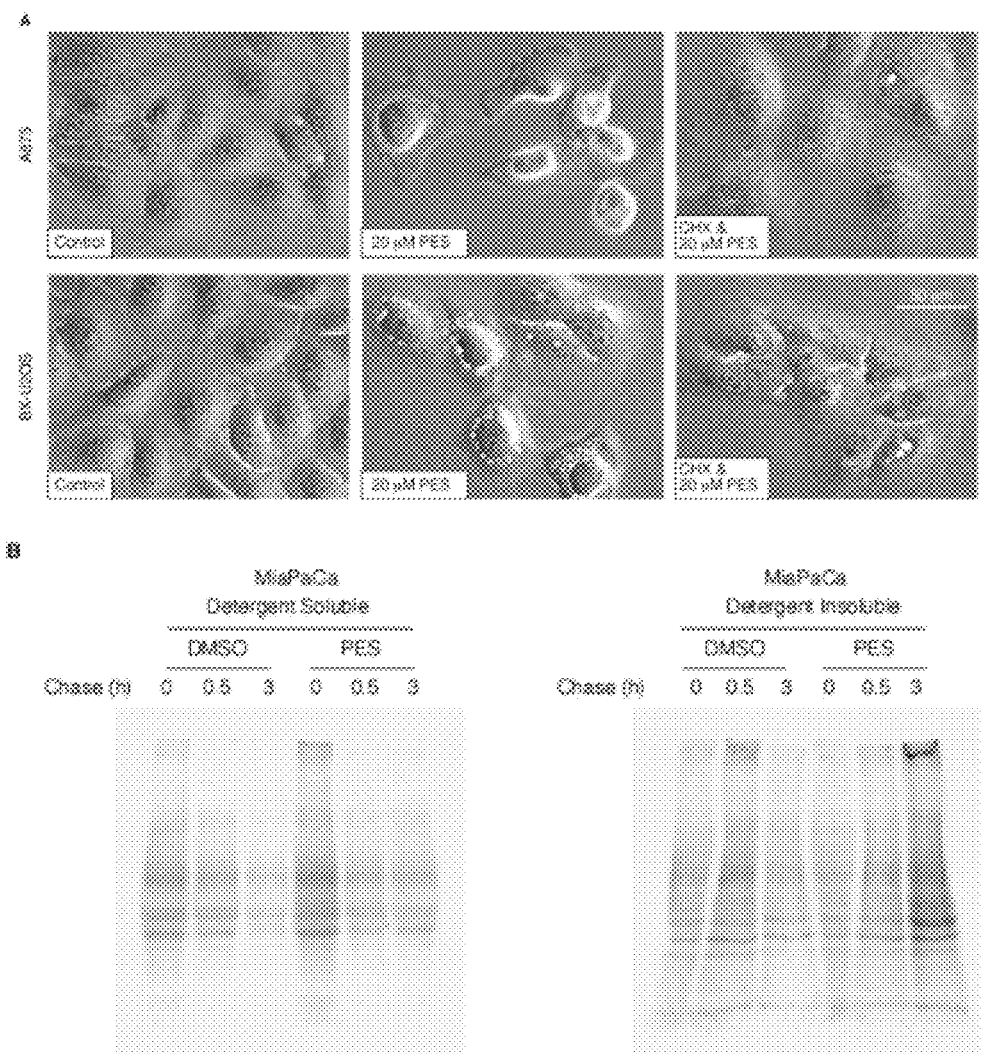
FIG. 13. Cycloheximide Reduces PES-Induced Cytoplasmic Vacuolization. (A) Representative phase-contrast images of indicated tumor cell lines pretreated with DMSO or 1 μg/ml of cycloheximide (CHX) for 1 h, followed by the addition of 20 μM PES for 23 h. (B) The molecular chaperone HSP70 has been implicated in promoting proper folding of nascent polypeptides. Also, increased levels of p62/SQSTM1 have been found to result from either increased synthesis or blockage of autophagy. Since we found that PES inhibits long-lived protein degradation (FIG. 10A), we also evaluated how PES might affect the disposition of newly synthesized proteins. Briefly, MiaPaCa2 cells were incubated in methionine/cysteine starvation medium for 30 min before adding [$^{35}$S]methionine/cysteine and DMSO or [$^{35}$S]methionine/cysteine and 20 μM PES, as indicated, to pulse for 1 h. Following the pulse, cells were immediately chased by complete medium for 0, 0.5, or 3 h, either in the presence of DMSO or 20 μM PES, as indicated. Cells were harvested at indicated time points, lysed in 1% NP40-containing buffer, and fractionated into detergent-soluble and detergent-insoluble preparations. Note the increase in the newly-synthesized proteins in the detergent-insoluble fraction from PES-treated cells apparent 3 h following the chase in complete medium.
Figure 17:
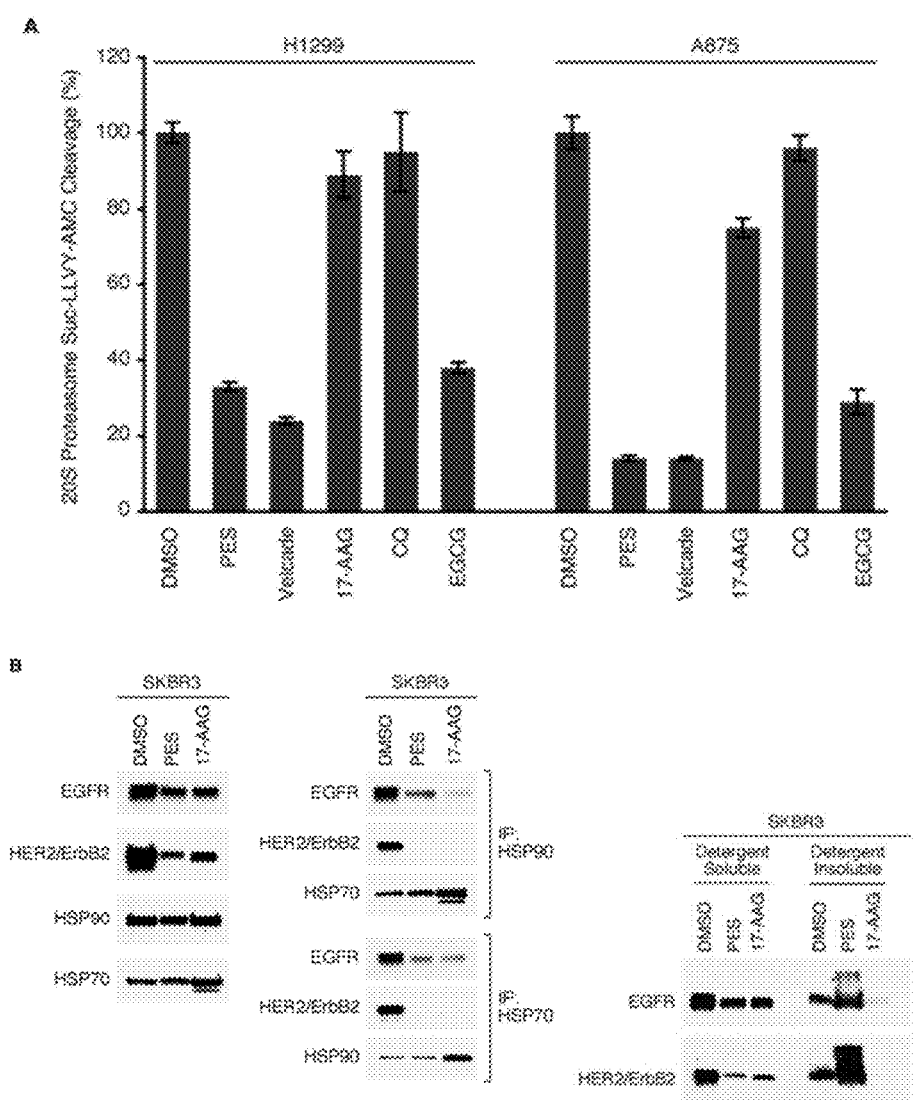
FIG. 17. PES impairs the proteasome system. (A) Cell-based 20S proteasome activity assay of H1299 or A875 human tumor cells treated with DMSO, 20 μM PES, 100 nM Velcade (proteasome inhibitor), 1 μM 17-AAG (HSP90 inhibitor), 5 μM CQ (lysosome inhibitor), or 20S proteasome inhibitor epigallocatechin gallate (EGCG). Each graphical representation indicates the mean±SD of at least three independent cultures relative to control (DMSO-treated) cells. (B) Cell extracts from SKBR3 human breast carcinoma cells, treated either with 20 μM PES or 1 μM 17-AAG for 24 h, were immunoprecipitated (IP) using anti-HSP70 or anti-HSP90 antibody. Western blots assessed the relative abundance of the proteins indicated (left), and co-immunoprecipitation-western (IP-WB) analysis revealed a reduced degree of interaction between HSP90 and client proteins EGFR and HER2/ErbB2, in response to the HSP90 inhibitor 17-AAG as well as the HSP70-inhibitor PES (middle). Note that 17-AAG has previously been shown to abrogate HSP90's interactions with client proteins such as EGFR and HER2/ErbB2, leading to their destabilization and depletion by proteasome-mediated proteolysis. Our data suggest that PES similarly disrupts at least some of these chaperone-substrate interactions. We also have data showing that the client proteins EGFR and HER2 are shunted into a detergent insoluble cellular fraction in the presence of PES, suggestive of inactivation (right). (C) PES sensitizes cells to cell killing by 17-AAG. MTT assays of MCF7 human breast carcinoma cells pretreated with DMSO, or 5 μM PES for 1 h, followed by the addition of indicated amount of 17-AAG for 47 h. The results represent the mean±SD of at least three independent analysis of cultures relative to control (DMSO-treated) cells. (D and E) H1299 cells (D) or SKBR3 cells (E) were treated with DMSO, 20 μM PES, 17-AAG, or 17-AAG plus bortezomib (Velcade) as indicated; harvested in 1% NP-40 containing lysis buffer; fractionated into detergent-soluble and detergent-insoluble preparations; and assayed by western blot.
Figure 17:
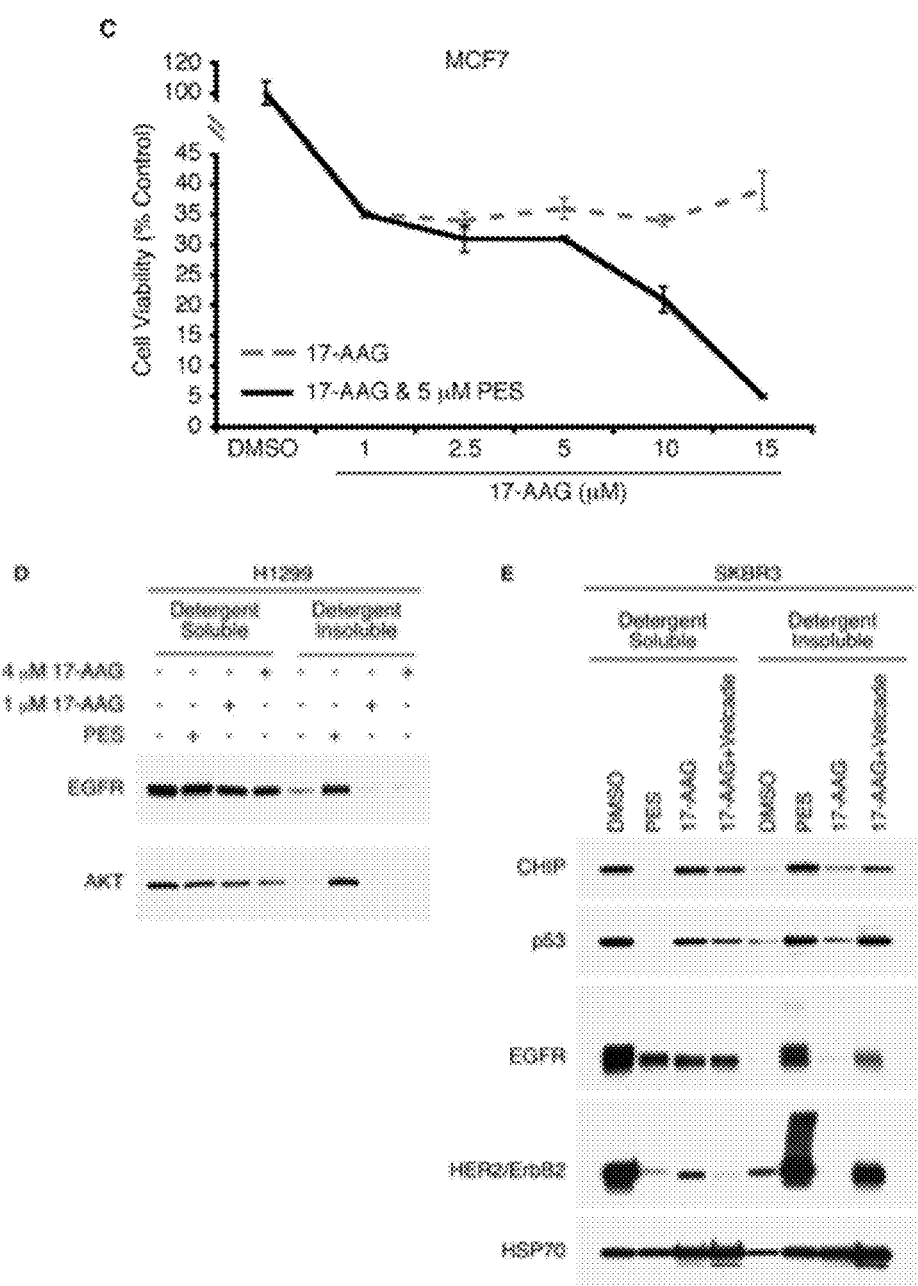

Accumulation of PES-Induced p62/SQSTM1 Oligomers in Soluble and Detergent-Insoluble Fractions Endogenous p62/SQSTM1 has been found in detergent-insoluble preparations following inhibition of autophagic degradation (Bjørkøy et al., 2005; Shvets et al., 2008). Thus, we asked whether these oligomers are present in a detergent-insoluble fraction, indicating a change to a more aggregated conformation. For these analyses, cells were treated either with PES, the proteasome inhibitor Velcade (bortezomib), or the lysomotrophic drug chloroquine (CQ). CQ has been found to inhibit a late stage in autophagy and inhibit tumorigenesis by raising lysosomal pH, thereby impairing lysosomal protein degradation and autophagic vesicle clearance (Amaravadi et al., 2007; Maclean et al., 2008). PES-treated cells contain higher molecular weight forms of p62/SQSTM1 in both the soluble and detergent-insoluble fractions (FIGS. 11I and 11J). In contrast, CQ and Velcade promoted p62/SQSTM1 oligomerization primarily in the detergent-insoluble fraction (FIGS. 11I and 11J). Also, neither p62/SQSTM1 accumulation nor oligomerization was noted following treatment of cells with the HSP90 inhibitor 17-allylamino-17-demethoxygeldanamycin (17-AAG) (FIG. 11J and data not shown), suggesting that the actions of PES are distinct from these agents, at least in some respects. The molecular chaperone HSP70 has been implicated in promoting proper folding of nascent polypeptides. To analyze nascent polypeptides, we co-treated cells with PES and the general protein translational inhibitor cycloheximide (CHX) for 6 h. This reduced the accumulation and oligomerization of the autophagy marker p62/SQSTM1 in the detergent-resistant fraction with a concomitant reduction of LC3-II levels (FIG. 11K), and retarded the appearance of PES-induced cytoplasmic vacuolization (FIG. 13A). These data are consistent with a PES-mediated inhibition of HSP70 function in protein quality control pathways. In further support of this finding, we show that PES impairs the proteasome system (FIG. 17).

A sensitive marker of autophagic flux is the adaptor/scaffold protein p62 (also known as sequestosome1 {SQSTM1}, A170, or ZIP), a stress-induced protein implicated in many cellular pathways. Among its activities, p62/SQSTM1 regulates the formation and removal of intracellular aggregates. Because p62/SQSTM1 is degraded by autophagy, an inhibition of that pathway promotes the accumulation and oligomerization of p62/SQSTM1 (Bjørkøy, et al. 2005; Komatsu, et al. 2007; Pankiv, et al. 2007; Klionsky, et al. 2008; Korolchuk, et al. 2009). Another marker of autophagy, LC3 (microtubule-associated protein-1 light-chain 3) is converted from an 18 kDa cytoplasmic form (LC3-I) to a smaller (16 kDa) lipidated form (LC3-II), which integrates into newly formed autophagosome membranes along with p62/SQSTM1 (Komatsu, et al. 2007; Pankiv, et al. 2007; Klionsky, et al. 2008; Ichimura, et al. 2008). Accordingly, we used Western blot analysis to determine the effect of PES on p62/SQSTM1 and LC3-II expression in IMR90 and H1299 cells. The results show that untreated H1299 cells exhibit some level of p62 oligomerization (FIG. 11N), in accord with current evidence indicating that autophagy is induced in established tumors as a survival mechanism in the face of enhanced stress, including chemotherapy. Consistent with previous results that PES impairs autophagic flux, treatment of the cells with increasing concentrations of PES produced a notable increase in p62/SQSTM1 accumulation and oligomerization in H1299 cells (FIG. 1H). In contrast, IMR90 cells displayed only a modest degree of p62 oligomerization and LC3-II accumulation at the highest PES concentration employed (FIG. 1H). The combined data thereby suggest that p62/SQSTM1 may serve as a molecular signature for PES-induced autophagy-related toxicity, especially given that a significant increase in p62/SQSTM1 levels is indicative of an accumulation of aggregated or undegraded proteins.

The autophagy-lysosome system is important for the degradation of long-lived proteins, organelles, and other cytoplasmic cargo, and it aids in the removal of oligomeric and aggregated proteins. The 26S-proteasome system is central to the controlled turnover of short-lived proteins, such as cell cycle regulatory factors, as well as certain misfolded proteins. Perturbing either system can result in the abnormal accumulation of potentially toxic protein aggregates. Recent studies indicate that the autophagy-lysosome and proteasome systems are mechanistically linked; autophagy may be induced in response to proteasome inhibition, and an inhibition of autophagy can directly impair the function of the proteasome system, perhaps because the cellular abundance of misfolded or aggregated proteins exceeds the capacity of the system to process these molecules (Korolchuk, et al. 2009; Bennett, et al. 2005; Ding, et al. 2009). Given the key role of HSP70/HSC70 in targeting misfolded proteins and aggregates for elimination through both of these proteolytic pathways, we extended our studies to assess the effect of PES on proteasome function. We employed a widely-used fluorogenic assay to measure the protease activity of the 20S core unit of the 26S proteasome. H1299 human lung carcinoma cells or A875 human melanoma cells were treated individually with the following agents: the HSP70-inhibitor, PES; the proteasome-inhibitor, bortezomib (also called Velcade or PS-341); (−)-epigallocatechin gallate (EGCG), a specific inhibitor of the 20S proteasome); the autophagy inhibitor chloroquine (CQ); the HSP90-inhibitor, 17-AAG. The results of these assays using two different tumor cell lines demonstrate that PES impairs the activity of the 20S proteasome in vivo in a manner comparable to that of the known proteasome-inhibitors Velcade and EGCG (FIG. 17A). In contrast, 17-AAG and CQ have little, if any, effect (FIG. 17A). Thus, the activities of PES are distinct when compared to other compounds that impair autophagy or the HSP90 molecular chaperone.

Figure 18:
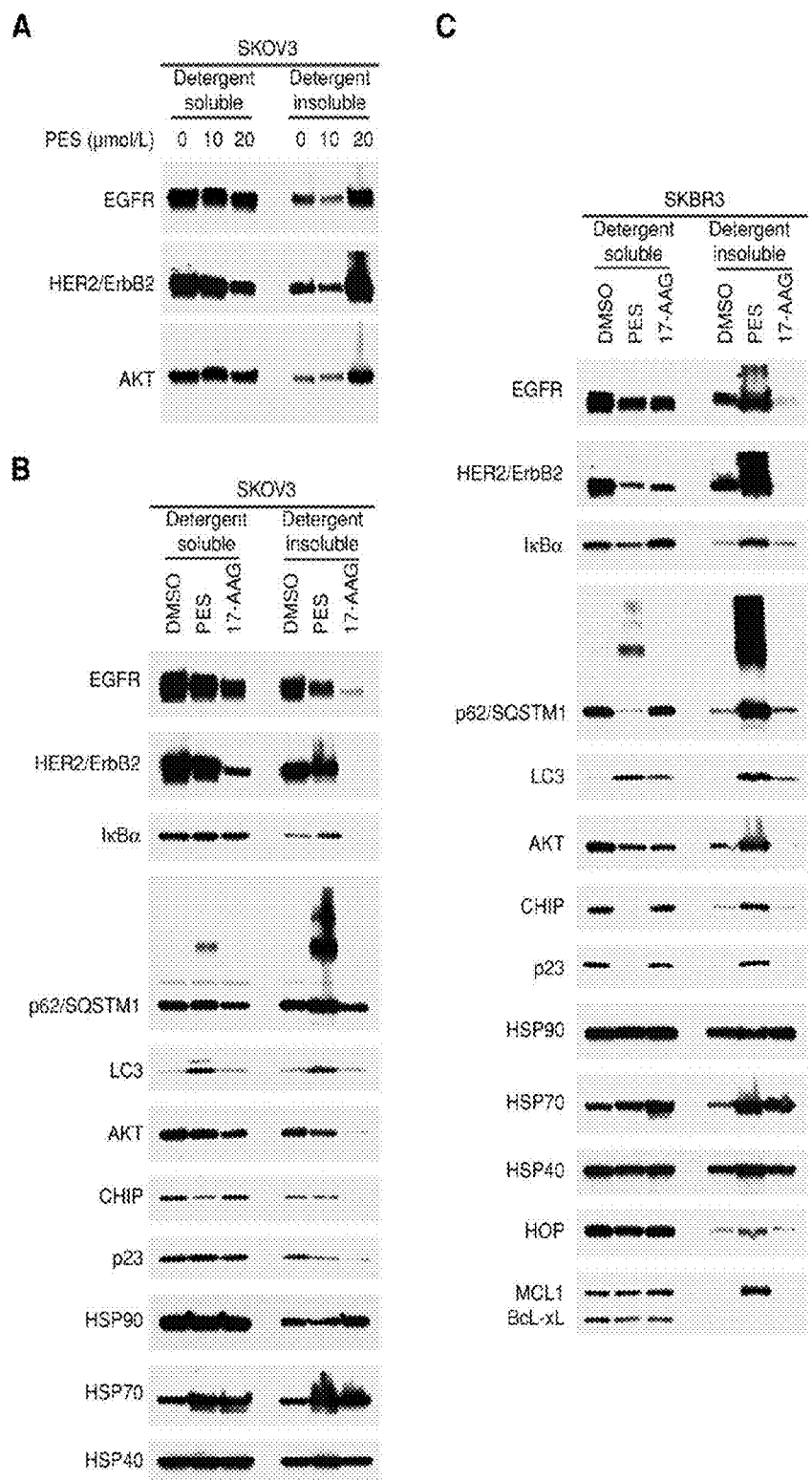
FIG. 18. Accumulation of HSP90 client proteins in the protein detergent-insoluble fraction following PES. (A) SKOV3 cells were treated with DMSO, 10 μM PES, or 20 μM PES for 24 h. Note the marked accumulation of EGFR, HER2/ErbB2, and AKT in the detergent-insoluble fraction following 20 μM PES treatment. (B and C) SKOV3 (B) or SKBR3 (C) cells were treated with DMSO, 20 μM PES, or 1 μM 17-AAG, as indicated, for 24 h. Cells were harvested in 1% NP-40 containing lysis buffer, fractionated into detergent-soluble and detergent-insoluble preparations, and assayed by western blot for the proteins indicated.

When the proteasome and/or autophagy-lysosome pathways in cells are impaired, many cellular proteins exhibit increased oligomerization and/or aggregation. These aggregates tend to accumulate in a detergent-insoluble cell fraction (Korolchuk, et al. 2009; Bennett, et al. 2005; Mimnaugh, et al. 2006). Therefore, the fate of HSP70/HSP90 client proteins in PES treated cells was questioned. The results of western blot analyses demonstrate an increased abundance of EGFR, HER2/ErbB2, and AKT in the detergent-insoluble fraction, even under conditions where there is not an obvious decrease in protein abundance in the detergent-soluble fraction (clarified whole-cell lysates) (FIGS. 17 and 18). This may reflect an effect of PES on basal turnover of these proteins. Similar results were obtained when PES-treated SKBR3 cells were examined for the expression of several other proteins, including the HSP70/HSP90 client mutant p53 and the co-chaperone protein CHIP (FIGS. 17 and 18). The latter is a ubiquitin ligase that interacts with HSC70/HSP70 as well as HSP90 to promote the ubiquitination and degradation of client proteins (McDonough, et al. 2003; Murata, et al. 2003). In contrast to the effects of PES, 17-AAG causes proteasome-mediated degradation of HSP90 client proteins (FIGS. 17D and E). However, preventing the turnover of these substrates by co-treatment of tumor cell lines with an HSP90 inhibitor together with a proteasome-inhibitor leads to their accumulation as detergent-insoluble forms (Mimnaugh, et al. 2006; Mimnaugh, et al. 2004). Accordingly, treating cells with PES alone produces an outcome that is similar to that obtained when using 17-AAG in combination with Velcade; namely, there is a reduced abundance of HSP70/HSC70/HSP90 client proteins in the detergent-soluble fraction and an increased abundance of detergent-insoluble forms (FIG. 17E).

Since the HSP70/HSP90 molecular chaperone machinery has a large number and wide variety of client proteins in tumor cells, the effects of PES and 17-AAG on the expression of several other cellular proteins were compared in SKBR3 breast cancer, or SKOV3 ovarian cancer, cells. The data reveal that many of the proteins examined accumulate in the detergent-insoluble fraction following exposure of the cells to PES (FIG. 34A-C). Among these are several chaperone proteins, such as HSP40, p23 and HOP, the signaling factor p62/SQSTM1, the antiapoptotic protein MCL1, and the NFkB inhibitor IkBα. (FIG. 18A-C). Thus, one consequence of PES treatment includes diminished chaperone and substrate availability. Enrichment of chaperones in the insoluble protein fraction indicates the formation of aggresomes or aggregates, likely in an unsuccessful effort by the protein quality control machinery to rid the cell of misfolded, aggregated, or unwanted macromolecules.

Selectivity of PES-Mediated Cytotoxic Effects in Tumor Cells vs. Non-Transformed Cells PES is preferentially toxic for human tumor cell lines relative to non-tumor cells (Leu, et al. 2009). The half maximal concentration of PES to exert its cytotoxic effect ($IC_{50}$) in various tumor cell lines was determined to be in the range of 4-10 μM. To illustrate, there is a dose-dependent loss of viability for H1299 human lung carcinoma cells treated with PES; in contrast, there is minimal effect on normal human lung fibroblasts (IMR90) except at the highest concentrations used in this experiment (FIG. 1F). It was asked if this differential cytotoxicity correlates with the interaction of PES with HSP70/HSC70. In cells treated with B-PES (20 μM), both HSP70 and HSC70 are found together with this small molecule in the tumor cells (FIG. 1G). Interestingly, we did not observe a PES interaction with these molecular chaperones in the IMR90 fibroblasts. These data support the hypothesis that the selective cytotoxic effects of PES in tumor cells correlate with its interactions with HSP70/HSC70.

The HSP70/HSC70 molecular chaperones function in a coordinated manner with proteolytic systems in cells to help maintain protein quality control. At least in solid tumors, PES-mediated inhibition of HSP70 activities impairs the autophagy-lysosome pathway, leading to an accumulation of misfolded and aggregated proteins (Leu, et al. 2009). Given the differential interactions of PES with HSC70/HSP70 in non-transformed and transformed cells, the IMR90 and H1299 cells also were examined for evidence of altered autophagy in response to PES treatment. Macroautophagy, referred to here as autophagy, is an evolutionarily conserved degradative process in which long-lived proteins, organelles and aggregates are sequestered in double-membrane vesicles, called autophagosomes (Levine, et al. 2008; Mizushima, et al. 2008; Mehrpour, et al. 2010; Yang, et al. 2010). Fusion of the autophagosomes with enzyme-containing lysosomes promotes degradation of the sequestered material. Basal levels of autophagy occur in all cells to promote survival, and this pathway is induced in response to many forms of stress.

PES Alters the Expression Pattern of HSP70/HSP90 Client Proteins

Figure 19:
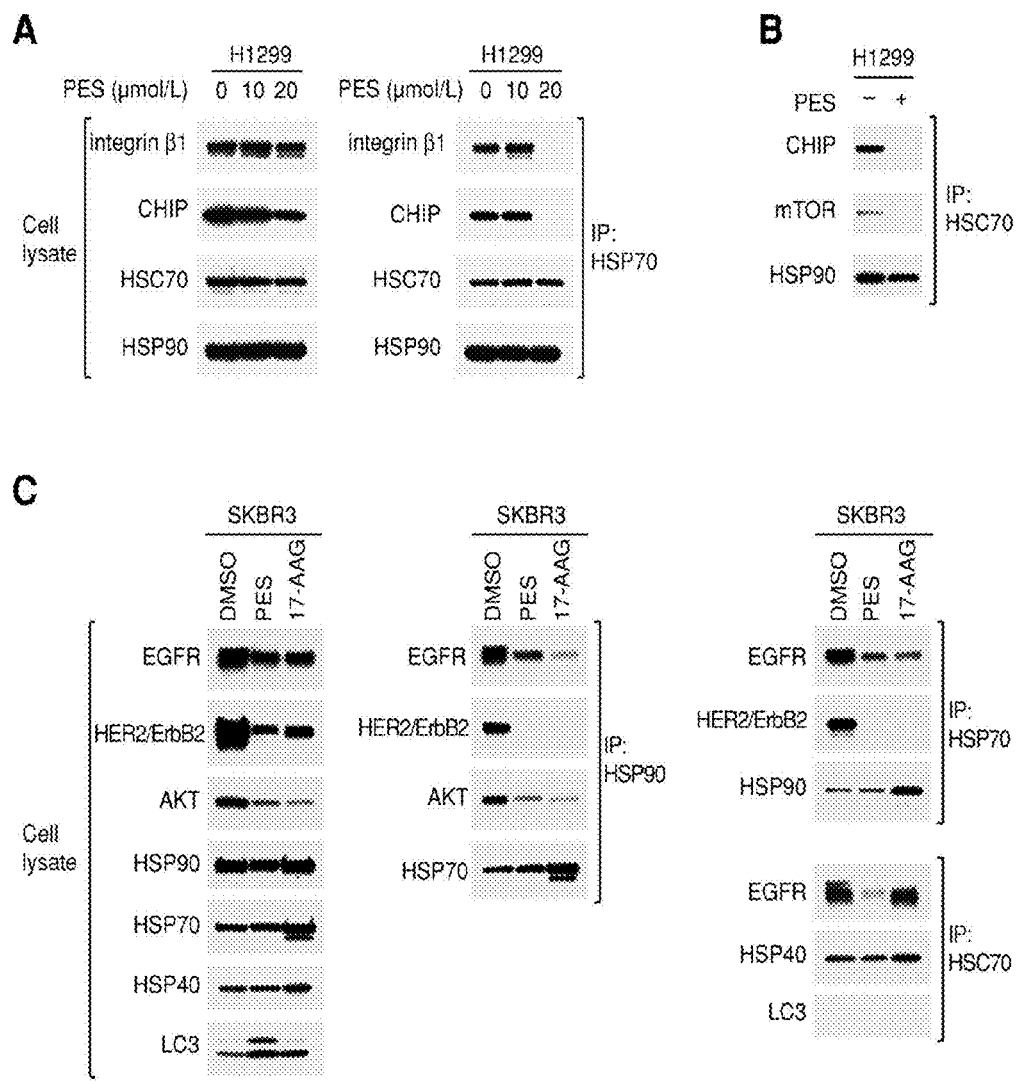
FIG. 19. PES treatment attenuates interactions between HSP70, HSC70, and HSP90 with client proteins or co-chaperones. H1299 lung carcinoma cells (A and B) or SKBR3 breast carcinoma cells (C) were treated with DMSO, 20 μM PES, or 1 μM 17-AAG (HSP90 inhibitor) for 24 h. Western blots (WB) assessed the relative protein abundance. Communoprecipitation-western (IP-WB) revealed a reduced abundance of complexes containing HSP90, HSC70, or HSP70 with the client proteins shown.

The HSP70 and HSC70 proteins bind to exposed hydrophobic regions of nascent-, translocating-, misfolded- or partially unfolded-proteins. These ATP-dependent molecular chaperones act in multi-protein complexes in conjunction with one or more regulatory co-chaperones to carry out multiple cellular functions. The data show that, in a dose-dependent fashion, PES exposure causes a reduction in the cellular abundance of at least a subset of these HSP70/HSC70-containing complexes (Leu, et al. 2009). This is illustrated for H1299 cells treated with 10 or 20 µM PES for 24 h. The latter concentration of PES results in lower expression levels of the client protein, integrin β1, as well as the co-chaperone CHIP (FIG. 19A). This correlates with a reduced abundance of complexes containing HSP70, or HSC70, together with client proteins or co-chaperones (FIGS. 19A and 19B). Under the same conditions, PES does not alter the overall abundance of complexes containing HSP70 with its co-chaperones HSC70 or HSP90 (FIGS. 19A and 19B). However, since HSP70/HSC70 act as critical co-chaperones for HSP90, for example in client protein recruitment, PES-mediated alteration in the function of the 70-kDa molecular chaperones could be reflected in an altered behavior or expression of many client proteins. To test this idea, we examined the expression of a few well-established HSP90 client proteins, including the transmembrane tyrosine kinase receptors EGFR and HER2/ERBB2, and the downstream signaling factor AKT. These proteins are overexpressed, or aberrantly expressed, in a variety of human tumors, and have been implicated in cancer etiology and pathology. As a control for these studies, we compared the effects of PES to that of the well-established HSP90 inhibitor, 17-allylamino-17-demethoxygeldanamycin (17-AAG). 17-AAG interacts with the N-terminal region of HSP90 and inhibits its ATPase activity; this disrupts interactions of HSP90 with client proteins and leads to client-protein degradation via the ubiquitin-proteasome pathway (Whitesell, et al. 2005; Neckers, et al. 2007). To examine the expression of some HSP70/HSP90 clients, we used western blot analysis of detergent-soluble (clarified) whole cell extracts.

As illustrated by an analysis of SKBR3 breast cancer cells, in the presence of PES, as with 17-AAG, there is a reduction in the overall cellular abundance of EGFR, HER2/ErbB2, and AKT (FIG. 19C). Co-immunoprecipitation assays confirmed that these HSP90 client proteins also are partners of HSP70/HSC70, and that treatment of cells with PES concomitantly reduces the abundance of complexes containing these tumor-promoting substrates and the molecular chaperones (FIG. 19C). Thus, by targeting HSP70/HSC70 functions, PES also impairs critical activities of HSP90.

Discussion

The stress-inducible molecular chaperone HSP70 participates in numerous cellular pathways and interacts with a varied group of proteins, including key factors in signal transduction, transcription, cell cycle control and stress response (Mayer and Bukau, 2005; Brodsky and Chiosis, 2006; Garrido et al., 2006; Schmitt et al., 2006; Powers and Workman, 2007). HSP70 activities also have been implicated in the pathogenesis of several human diseases, including cancer. Thus, there is growing interest in the identification of HSP70 modulators to better understand the many cellular activities of this protein. In this study we provide evidence that the small molecule PES interacts with HSP70, alters its functions, and is cytotoxic to tumor cells. PES-induced tumor cell death is not dependent on caspase activation or p53 function, and is not inhibited by overexpression of the anti-apoptotic BCL-xL protein. Rather, loss of cell viability is associated with protein aggregation and an impairment of lysosomal functions resulting in a disruption of autophagic processes.

Autophagy is a catabolic process characterized by the self-digestion of cellular constituents in lysosomal compartments. This degradative process is an important mechanism for the disposal of altered cytoplasmic constituents, including aggregated proteins, and it can be activated in tumor cells by various stressors, including as a response to therapies, nutrient deprivation, or following an inhibition of apoptosis. The process generally serves to promote survival under adverse conditions, in part by helping to prevent the accumulation of damaged proteins and organelles, and by supporting the metabolic needs of the cell (Debnath et al., 2005; Eskelinen, 2005; Levine and Kroemer, 2008; Mizushima et al., 2008). Several lines of investigation point to HSP70 as a regulator of lysosomal activities and, thereby, of autophagy. For example, recent studies demonstrate that the stress-inducible HSP70 protein exhibits tumor-specific localization at membranes of the endosomal/lysosomal compartment, and that it contributes to tumor cell survival by inhibiting lysosomal permeabilization induced by diverse stimuli (Nylandsted et al., 2004; Daugard et al., 2007; Ryhanen et al., 2008). In addition, the interaction of HSP70 and the lysosomal marker LAMP2, which is disrupted by PES, has been implicated in the formation of complexes at lysosomes that are important for lysosomal activities such as the translocation of soluble substrates during chaperone-mediated autophagy. Previous work indicates that inhibiting lysosomal functions following activation of autophagy can result in cancer cell death (Amaravadi et al., 2007; Degtyarev et al., 2008; Maclean et al., 2008). As presented here, PES-treated cells exhibit a significant reduction in the degradation of long-lived proteins and an obvious defect in the processing of the precursor form of cathepsin L to the mature lysosomal form of this cysteine protease. Such observations support the conclusion that PES impairs autophagy in part by its inhibitory effects on lysosomal functions.

HSP70 also is a regulator of apoptosis that has been reported to associate with APAF1 and to either block, or promote, apoptosome formation, depending on experimental conditions (Beere et al., 2000; Saleh et al., 2000; Kim et al., 2008). Recent studies indicate that HSP70 interacts with the tumor suppressor protein PHAPI and the cellular apoptosis susceptibility protein CAS; together these three proteins play an important role in helping with the proper folding of APAF1 to prevent its aggregation and to stimulate apoptosome assembly and caspase activation (Kim et al., 2008). Consistent with such a model, our studies reveal that in the presence of PES, the interaction of HSP70 with its substrate APAF1 is diminished, and this correlates with a significant reduction in caspase activation following cisplatin treatment of tumor cell lines. PES also inhibits the appearance of the HSP70/p53 complex and the stress-induced localization of p53 to mitochondria, thus interfering with p53-mediated apoptosis.

HSP70 regulation and function is mediated by its interactions with co-factors or co-chaperones. PES disrupts several of these interactions, including the association of HSP70 with CHIP, BAG-1M, and HSP40. Both CHIP and BAG-1 help regulate the ATPase activity of HSP70. It has been suggested that, in binding to both HSP70 and substrates, co-factors like CHIP and BAG-1 also may serve as a direct physical link between the chaperone and the proteasome, perhaps aiding in the targeting or selection of substrates for degradation (Mayer and Bukau, 2005; Townsend et al., 2005; Kabbage and Dickman, 2008). The HSP40 co-factor also works with HSP70 to induce conformational changes of certain substrates, in part by promoting ATP hydrolysis and preventing protein aggregation (Fan et al., 2003; Vos et al., 2008). HSP-interacting proteins, including CHIP, HSP40, BAG-1 and the scaffold-adapter protein p62/SQSTM1, also associate with many other cellular proteins to mediate diverse biological processes and signaling pathways. Altering HSP70 function therefore also has consequences for the activities of these other regulatory proteins. For example, recent data show that an inability to eliminate p62 through autophagy can lead to a toxic increase in oxidative stress and DNA damage in some tissues, and that autophagy inhibition also can compromise the Ubiquitin proteasome system, leading to a potentially lethal accumulation of aggregation-prone or misfolded proteins (Korolchuk et al., 2008; Matthew et al., 2009). Considered together, these data are consistent with the idea that PES alters the activities of HSP70 in multiple cellular processes, disabling the normally cytoprotective role of this molecular chaperone. Interestingly, since PES selectively interacts with HSP70, the deleterious consequences of this compound may depend on the presence of this protein. Our investigations on the cell-death inducing properties of PES are supportive of this idea, in that cultured tumor cells which generally have greater levels of HSP70 are much more sensitive to the cell death effects of this small molecule than are non-transformed fibroblasts. Additionally, reducing HSP70 levels in tumor cells reduces the cytotoxic effects of PES exposure. In this regard, PES may cause HSP70 to adopt a potentially lethal "gain-of-function" activity along with a loss of its pro-survival role.

HSP70 has a key cytoprotective role in a broad range of activities that promote protein homeostasis, including the targeting of potentially toxic proteins for proteolysis. Cancer cells experience high levels of protein-modifying- and metabolic-stresses and seem to be particularly dependent on the various actions of HSP70 for survival. This phenomenon, referred to as non-oncogene addiction", suggests that it may be possible to target such critical survival proteins for the development of therapies aimed at the selective killing of neoplastic cells (Solomini et al., 2007). In support of this idea, our in vivo analysis indicate that administration of PES inhibits spontaneous tumor development and enhances survival in the Eμ-Myc model of lymphomagenesis. Thus PES represents a valuable new tool for impacting the varied activities of the HSP70 protein, and has applications in the development of effective therapies aimed at simultaneously disabling multiple cancer-critical biological processes.

Example 2

Figure 20A:
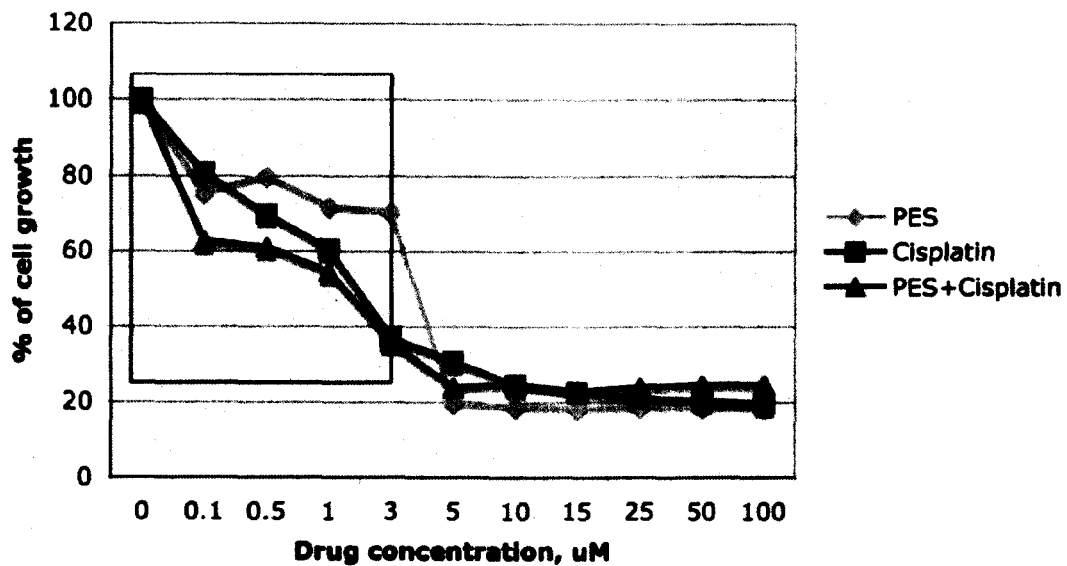
Figure 20B:
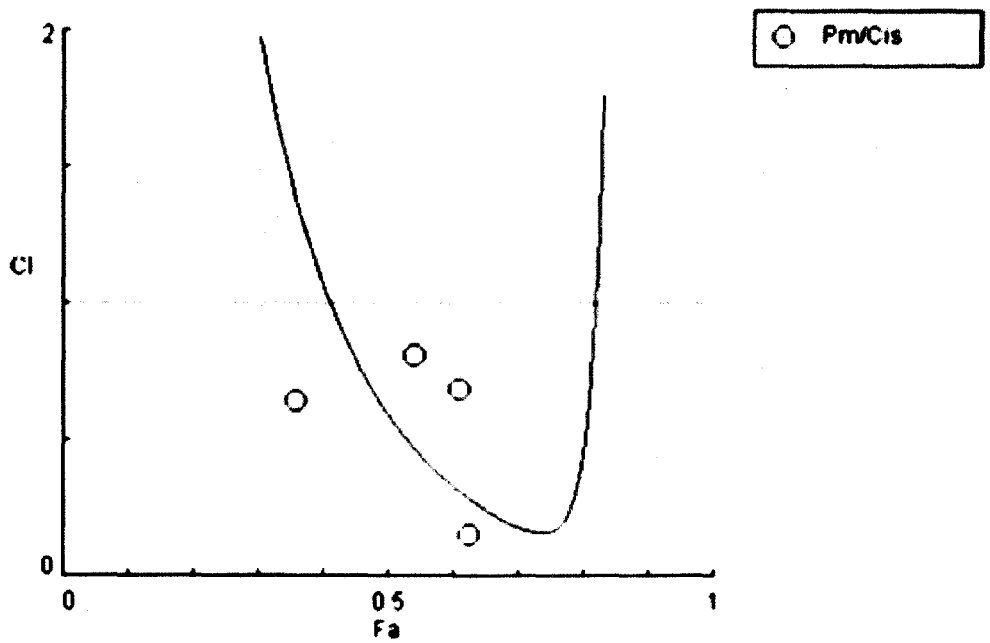

Combined PES and Chemotherapy and/or Radiation Treatment Effectively Kills Cancer Cells PES was originally identified as an inhibitor of mitochondrial p53. Hsp70s function to re-fold misfolded proteins, and to enable protein trafficking to mitochondria, and across membranes. Silencing HSP70 universally kills tumor cells, with little toxicity to normal cells. As discussed above in Example 1, PES inhibits autophagy which is known to protect cells from hypoxia mediated cell death. Hypoxia is well known to protect cancer cells from the impact of chemotherapeutic agents and radiation. Accordingly, we performed experiments to assess whether PES cooperated with either a chemotherapeutic agent or radiation to induce tumor cell death by inhibiting autophagy/survival. As shown in FIGS. 20A and 20B and described above, PES acts synergistically with cisplatin to kill FADU cells.

In further experiments we subjected FADU cells to a combination of PES (10 μM) and gamma irradiation (10 Gy). The data, shown in FIG. 21, reveal that PES and radiation combine effectively to reduce the capacity to form colonies in these cells. FIG. 22 reveals that this effect is not cell type specific. Scc61 cell were also treated with a combination of PES and gamma irradiation, in this case 2 Gy. As above, this combination of treatments effectively diminished the capacity of these cells to form colonies in a colony formation assay. This data combined with that presented in Example 1, clearly demonstrate that PES administration in combination with either chemotherapy or radiation or both is effective for eradicating tumor cells in vivo and in vitro.

The following materials and methods are provided to facilitate the practice of Example 3.

Synthesis and Characterization of PES-Cl

Scheme 1: Synthesis of 2-(3-chlorophenyl)-ethynesulfonamide (PES-Cl) from Chlorosulfonyl Isocynate (See Example 1).

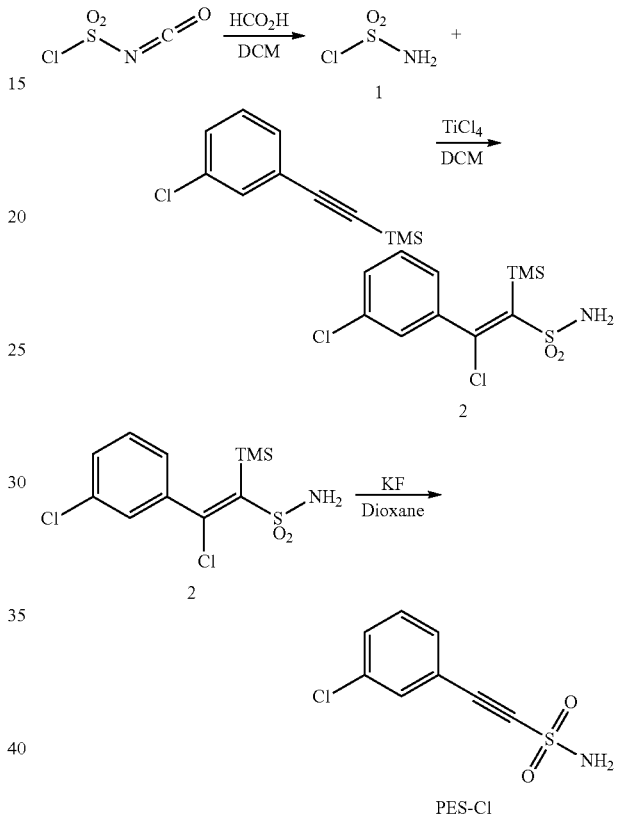

2-(3-chlorophenyl)-ethynesulfonamide (PES-Cl) was initially prepared from chlorosulfonyl isocyanate. Chloroisocyanate was converted to the sulfonamide 1 following treatment with formic acid in dichloromethane (DCM) (J. D. Patrone, J. Yao, N. E. Scott and G. D. Dotson, JACS 131, 16340 (2009)). The chlorosulfonamide 1 was then dissolved in DCM and a solution of titanium tetrachloride in DCM was added dropwise. To the mixture was added 3-chlorophenyl-3-trimethylsilylethyne in DCM at −20° C. which provided vinyllic sulfonamide 2 as a tan solid. The vinyllic sulfonamide 2 was then prepared with potassium fluoride in dioxane and nitromethane. The mixture was heated to 50° C. and stirred for 54 hours to provide PES-Cl in 50% yield (P. Babin, J. Dunogues, G. Felix, P. Lapouyade, R. Calas, J. Chem. Research 1982, 16-17).

Materials and Methods.

Chlorosulfonyl isocyanate (14, 266-2; lot STBB0539AO), (3-chlorophenylethynyl)trimethylsilane (597708-1G; lot 16126BB) and titanium chloride (Aldrich 20, 856-6; lot 9526) was purchased from Aldrich. Formic acid was purchased from Sigma (F0507100ML; lot 039K0108). Potassium fluoride (Acros 20135-0250; lot B0126755B) was dried under vacuum at room temperature just prior to use. Dichloromethane, nitromethane and dioxane were dried by storage over calcium hydride. LC-MS was performed using a Waters 2545 binary gradient module and a 2487 dual wavelength detector set to 254 and 365, a 2424 ELS detector and a 3100 MS detector. The gradient was linear 5% MeOH 95% H2O to 95% MeOH 5% H2O over 15 minutes. The column was a Waters Delta Pak C-18 15υ 100A 3.9×300 mm (catalog number 11797) run at a flow rate of 0.8 ml per minute. Preparative chromatography was run on a Waters LC-MS system using a prep pak C-18 delta-pak column (47×300 mm) UV detection was set at 254λ. Flow rate was 30 ml per minute. $^1$H NMR was performed on a Bruker WB Advance 300 MHz instrument. TLC sheets were silica gel 60 (Fisher M5719-2).

Chlorosulfonamide (1).

Exactly 9.2 ml (0.24 moles) of 95% formic acid was added dropwise over 15 minutes to 19.2 ml (0.22 moles) of chlorosulfonyl isocyanate in 100 ml of dry dichloromethane cooled in an ice bath under a stream of nitrogen over 15 minutes. The reaction mixture was stirred for 15 minutes in the cold bath, at room temperature for 45 minutes and finally heated to reflux for 45 minutes. The flask was placed in the freezer and 20.8 g (80% yield) of white crystals were collected and washed with dichloromethane. The chlorosulfonamide was dried under vacuum and stored in the freezer.

2-Chloro-2-(3-chlorophenyl)-1-(trimethylsilyl)ethenesulfonamide (2)

TiCl4, (21.55 mmol; 4.086 g; 2.367 ml) in 5 ml dichloromethane was added dropwise to the chlorosulfonamide (21.55 mmol; 2.48 g) in 20 ml dichloromethane at room temperature under a nitrogen atmosphere. The mixture was stirred for 30 minutes, then added dropwise over 10 minutes to 3-chlorophenyl-3-trimethylsilyl ethyne (21.55 mmol; 4.5 g) in 20 ml dichloromethane at −20° C. The solution turned brown upon addition. The reaction mixture was allowed to warm up to room temperature. It was left to stir overnight at room temperature. The next day, water was added and it was extracted with dichloromethane. The combined organic phases were washed with water, sodium bicarbonate solution followed by water, then dried over sodium sulfate. The solvent was removed under reduced pressure to a tan solid (wt 5.416; g; 77% yield). $^1$H NMR δ (CDCl$_3$): 7.31-7.50 (multiplet). $^{13}$C NMR δ (MeOD): 1.5; 128.6; 130.1; 131.5; 135.5; 143; 147.3; 149.7. TLC Rf=0.28 on silica (4% CH$_3$CN/96% CHCl$_3$). LC-MS RT=15.17 UV (M+324).

2-(3-chlorophenyl)ethynesulfonamide (PES-Cl)

Exactly 5.416 g (16.7 mmoles) of ethenesulfonamide and 952 mg (15.44 mmoles) of anhydrous potassium fluoride were stirred in 100 ml of dioxane and 100 ml of nitromethane under a nitrogen atmosphere. The yellow solution was heated to 50° C. for 54 hours. The solution was cooled then evaporated under reduced pressure to brown oil. Potassium chloride was removed by dissolving the oil in acetone and filtration of the inorganic salt. The filtrate was purified further by prep HPLC purification on a C-18 column using a 60 minute gradient of 5% to 95% MeOH. Fraction containing EM-214 was collected from 47 to 56 minutes and was contaminated with a small amount of compound with EM-430. It was rechromatography using the same gradient and the product (EM-214) eluted from 45 to 53 minutes. The solvents were removed under reduced pressure to give 1.793 grams (50% yield) of pure sulfonamide $^1$H NMR δ (MeOD): 7.40-7.61 (mulitplet). $^{13}$C NMR δ (MeOD): 82.2; 86.0; 119.5; 129.2; 129.4; 129.9; 130.5; 133.4. TLC Rf=0.19 on silica (4% CH$_3$CN/96% CHCl$_3$). LC-MS RT=14.09 UV (M−214).

Example 3

PES-Cl Interacts with HSP70

PES-Cl was shown to interact with HSP70. The free amide group of PES-Cl was biotinylated and added to HA-tagged HSP70-transfected H1299 cells. The treatment of the cells occurred for 6 hours. The complexes were pulled down with NeutrAvidin beads, eluted with 100 mM DTT treatments, separated with SDS-PAGE and detected with anti-HA antibody (Millipore) by Western blot. Both PES and PES-Cl were determined to interact with HSP70 (FIG. 23).

PES-Cl Inhibits Autophagy in H1299 and FaDu Cells

The inhibition of autophagy by PES-Cl was observed in the H1299 and FaDu cell lines. The potential of PES-Cl induced apoptosis was also observed. Tumorogenic cells H1299 and FaDu cells were seeded in 10 cm plates and were treated with 10 μM PES or 10 μM PES-Cl. DMSO treated cells were used as a vehicle treated control. Twenty-four, 48 and 72 hours post-treatment the cells were scrapped and protein extracts were generated. Western blotting was performed as described hereinabove. The antibodies used in the protocol were p62 (Santa Cruz), Hsp70 (Cell Signaling), cleaved lamin A (Cell Signaling), Hsp40 (Cell Signaling), γH2A.X (Millipore), and actin (Sigma). PES-Cl inhibited autophagy and induced apoptosis in H1299 and FaDu cells (FIG. 24).

PES-Cl Induces Apoptosis in H1299 and FaDu Cells

The effect of PES-Cl on apoptosis was observed using Guana Nexin Reagent (Millipore) in H1299 and FaDu cells. The Guana Nexin Assay utilizes Annexin V-PE to detect phosphatidylserine (PS) on the external membrane of apoptotic cells. The cell impermeant dye, 7-AAD, is also used in the Guava Nexin Assay as an indicator of cell membrane structural integrity. 7-AAD is excluded from live, healthy cells as wells as early apoptotic cells. Three populations of cells can be distinguished in the assay: Non-Apoptotic cells (Annexin V(−) and 7-AAD(−)), Early Apoptotic cells (Annexin V(+) and 7-AAD(−)), and Late Stage Apoptotic and dead cells (Annexin V(+) and 7-AAD(+)). The H1299 and FaDu cells were seeded on 24-well plates and treated with 10 μM PES or 10 μM PES-Cl. DMSO treated cells were used as a vehicle control. Four, 24 and 48 hours post-treatment, the H1299 cells were washed with PBS and trypsinized. For FaDu cells, the time course was 24, 48 and 72 hours. The cells were pelleted and resuspended in Guava Nexin reagent as per the manufacturer instructions and the readings were obtained with a Guava reader (Guava Technologies, Millipore). The total number of cells that were in Late Stage Apoptosis or dead (by necrotic or apoptotic mechanisms) was analyzed in density plots to determine as Annexin V positive. In both H1299 (FIG. 25) and FaDu (FIG. 26) PES-Cl induced apoptosis and cell death.

PES-Cl Inhibits Myc-Induced Lymphoma Development

Beginning at 6 weeks of age, Eμ-myc transgenic mice were treated either with vehicle, 20 mg/kg PES or 20 mg/kg PES-Cl with weekly i.p. injections of tested compound (FIG. 27).

In the assay, PES-Cl extended survival in Eμ-Myc transgenic mice and suggests that PES-Cl is an effective agent in the treatment of certain forms of cancer.

PES-Cl Inhibits the Proliferation of Tumorogenic Cells

H1299 cells were seeded on 100 mM plates and treated with 10 μM PES or 10 μM PES-Cl. DMSO treated cells were used as a control and the proliferation of the H1299 cells was observed over 24 and 48 hours of treatment. The cells were imaged by light microscopy with 20× magnification (FIG. 28). Non-tumorogenic and tumorogenic cells were then treated with PES-Cl to observe its toxicity and effect on proliferation. Two tumorogenic cell lines (H1299 and FaDu) and two normal fibroblast cell lines (6113 and WI38) were seeded on a 96-well plate. The cells were treated with various concentrations of PES and PES-Cl. Forty-eight hours post-treatment MTT assays (Cayman Chemical Company) were performed (FIG. 29). Both PES and PES-Cl demonstrated a greater concentration dependent effect on cell survival in tumorogenic cells when compared to non-tumorogenic cells.

SKBR3 human breast adenocarcinoma cells were seeded and treated with PES and PES-Cl at various concentrations. After 72 hours MTT assays were performed demonstrating that PES-Cl is a superior cytotoxic agent when compared to PES in SKBR3 cells (FIG. 30).

PES-Cl Acts Synergistically with Temsirolimus to Kill Cancer Cells

PES-Cl was tested in combination with Temsirolimus, an mTOR inhibitor, to determine whether they act synergistically to kill cells. Head and neck cancer cells of the Scc56 cell line were treated with PES-Cl and Temsirolimus, singly and together, at varying concentrations utilizing an MTT assay. The combination of the two compounds displayed a synergistic effect resulting in enhanced dose-dependent cytotoxicity (FIG. 31)

Example 4

In Silico Modeling of PES Using a C-Terminal HSP70 Crystal Structure

Docking studies were performed using the C-terminal HSP70 crystal structure (FIG. 32) to elucidate the PES binding site in silico (FIG. 33). Blind docking methods were used in the program AutoDock to locate potential PES binding sites. These methods use a course grid docking approach, encompassing the entire protein, to identify favorable binding sites using a known binding ligand, and are examined by hand to support the AutoDock data. Mutants were predicted based upon molecular modeling studies to disrupt the PES ligand-protein interaction. Mutants were generated in HA-tagged HSP70 by site-directed mutagenesis, and transfected into cells. These mutants were used in binding assays with biotinylated PES as per Leu et al. (Mol. Cell. 2009) (FIG. 34). When L558R and Y611S were replaced HSP70 failed to bind PES.

REFERENCES

Aghdassi, A., Phillips, P., Dudeja, V., Dhaulakhandi, D., Sharif, R., Dawra, R., Lerch, M. M, and Saluja, A. (2007). Heat shock protein 70 increases tumorigenicity and inhibits apoptosis in pancreatic adenocarcinoma. Cancer Res. 67, 616-625.

Amaravadi, R. K., Yu, D., Lum, J. J., Bui, T., Christophorou, M. A., Evan, G. I., Thomas-Tikhonenko, A., and Thompson, C. B. (2007). Autophagy inhibition enhances therapy-induced apoptosis in a Myc-induced model of lymphoma. J Clin Invest. 117, 326-336.

Beere, H. M., Wolf, B. B., Cain, K., Mosser, D. D., Mahboubi, A., Kuwana, T., Tailor, P., Morimoto, R. I., Cohen, G. M., and Green, D. R. (2000). Heat-shock protein 70 inhibits apoptosis by preventing recruitment of procaspase-9 to the Apaf-1 apoptosome. Nat Cell Biol. 2, 469-475.

Bennett, E. J., Bence, N. F., Jayakumar, R., Kopito, R. R. (2005) Global impairment of the ubiquitin-proteasome system by nuclear or cytoplasmic protein aggregates precedes inclusion body formation. Mol Cell. 17, 351-65.

Bjørkøy, G., Lamark, T., Brech, A., Outzen, H., Perander, M., Overvatn, A., Stenmark, H., and Johansen, T. (2005). p62/SQSTM1 forms protein aggregates degraded by autophagy and has a protective effect on huntingtin-induced cell death. J Cell Biol. 171, 603-14.

Bjørkøy, G., Lamark, T., Pankiv, S., Overvatn, A., Brech, A., and Johansen, T. (2009). Monitoring autophagic degradation of p62/SQSTM1. Methods Enzymol. 452, 181-197.

Bandyopadhyay U, Kaushik S, Varticovski L, Cuervo A M. (2008). The chaperone-mediated autophagy receptor organizes in dynamic protein complexes at the lysosomal membrane. Mol Cell Biol. 28, 5747-5763.

Brodsky, J. L., and Chiosis, G. (2006). Hsp70 molecular chaperones: emerging roles in human disease and identification of small molecule modulators. Curr Top Med Chem. 6, 1215-1225.

Bukau, B., and Walker, G. C. (1989). Delta dnaK52 Mutants of Escherichia coli have defects in chromosome segregation and plasmid maintenance at normal growth temperatures. J. Bacteriol. 171, 6030-6038.

Chen, Y. C., Lin-Shiau, S. Y., and Lin, J. K. (1999). Involvement of heat-shock protein 70 and P53 proteins in attenuation of UVC-induced apoptosis by thermal stress in hepatocellular carcinoma cells. Photochem Photobiol. 70, 78-86.

Chen, H., Wu, Y., Zhang, Y., Jin, L., Luo, L., Xue, B., Lu, C., Zhang, X., and Yin, Z. (2006). Hsp70 inhibits lipopolysaccharide-induced NF-kappaB activation by interacting with TRAF6 and inhibiting its ubiquitination. FEBS Lett. 580, 3145-3152.

Collette, J., Bocock, J. P., Ahn, K., Chapman, R. L., Godbold, G., Yeyeodu, S., and Erickson, A. H. (2004). Biosynthesis and alternate targeting of the lysosomal cysteine protease cathepsin L. Int Rev Cytol. 241, 1-51.

Daugaard, M., Rohde, M., and Jäättelä, M. (2007). The heat shock protein 70 family: Highly homologous proteins with overlapping and distinct functions. FEBS Lett. 581, 3702-3710.

Debnath, J., Baehrecke, E. H., and Kroemer, G. (2005). Does autophagy contribute to cell death? Autophagy. 1, 66-74.

Degtyarev, M., De Mazière, A., Orr, C., Lin, J., Lee, B. B., Tien, J. Y., Prior, W. W., van Dijk, S., Wu, H., Gray, D. C., et al. (2008). Akt inhibition promotes autophagy and sensitizes PTEN-null tumors to lysosomotropic agents. J Cell Biol. 183, 101-116.

Ding, W. X., Ni, H. M., Gao, W., Chen, X., Kang, J. H., Stolz, D. B., et al. (2009) Oncogenic transformation confers a selective susceptibility to the combined suppression of the proteasome and autophagy. Mol Cancer Ther. 8, 2036-45.

Dumont, P., Leu, J. I., Della Pietra, A. C. 3rd, George, D. L., and Murphy, M. (2003). The codon 72 polymorphic variants of p53 have markedly different apoptotic potential. Nature Genet. 33, 357-365.

Duran, A., Linares, J. F., Galvez, A. S., Wikenheiser, K., Flores, J. M., Diaz-Meco, M. T., and Moscat, J. (2008). The signaling adaptor p62 is an important NF-kappaB mediator in tumorigenesis. Cancer Cell. 13, 343-354.

Eskelinen, E. L. (2005). Maturation of autophagic vacuoles in Mammalian cells. Autophagy. 1, 1-10.

Eskelinen E L. (2006). Roles of LAMP-1 and LAMP-2 in lysosome biogenesis and autophagy. Mol Aspects Med. 27, 495-502.

Fan, C. Y., Lee, S., and Cyr, D. M. (2003). Mechanisms for regulation of Hsp70 function by Hsp40. Cell Stress Chaperones 8, 309-316.

Garrido, C., Brunet, M., Didelot, C., Zermati, Y., Schmitt, E., and Kroemer, G. (2006). Heat shock proteins 27 and 70: anti-apoptotic proteins with tumorigenic properties. Cell Cycle 5, 2592-2601.

Guzhova, I., and Margulis, B. (2006). Hsp70 chaperone as a survival factor in cell pathology. Int Rev Cytol. 254, 101-149.

Humbey, O., Pimkina, J., Zilfou, J. T., Jarnik, M., Dominguez-Brauer, C., Burgess, D. J., Eischen, C. M., and Murphy, M. E. (2008). The ARF tumor suppressor can promote the progression of some tumors. Cancer Res. 68, 9608-9613.

Ichimura, Y., Kumanomidou, T., Sou, Y. S., Mizushima, T., Ezaki, J., Ueno, T., Kominami, E., Yamane, T., Tanaka, K., and Komatsu, M. (2008). Structural basis for sorting mechanism of p62/SQSTM1 in selective autophagy. J Biol Chem. 283, 22847-22857.

Kabbage, M, and Dickman, M. B. (2008). The BAG proteins: a ubiquitous family of chaperone regulators. Cell Mol Life Sci. 65, 1390-1402.

Kaushik, S., and Cuervo, A. M. (2009). Methods to monitor chaperone-mediated autophagy. Methods Enzymol. 452, 297-324.

Kim, H. E., Jiang, X., Du, F., and Wang, X. (2008). PHAPI, CAS, and Hsp70 promote apoptosome formation by preventing Apaf-1 aggregation and enhancing nucleotide exchange on Apaf-1. Mol Cell 30, 239-247.

Klionsky, D. J., Abeliovich, H., Agostinis, P., Agrawal, D. K., Aliev, G., Askew, D. S., Baba, M., Baehrecke, E. H., Bahr, B. A., Ballabio, A. et al. (2008). Guidelines for the use and interpretation of assays for monitoring autophagy in higher eukaryotes. Autophagy. 4, 151-175.

Komatsu, M., Waguri, S., Koike, M., Sou, Y. S., Ueno, T, Hara, T., Mizushima, N., Iwata, J., Ezaki, J., Murata, S. et al. (2007). Homeostatic levels of p62 control cytoplasmic inclusion body formation in autophagy-deficient mice. Cell. 131, 1149-1163.

Korolchuk, V. I., Mansilla, A., Menzies, F. M., and Rubinsztein, D. C. (2009). Autophagy inhibition compromises degradation of ubiquitin-proteasome pathway substrates. Mol Cell. 33, 517-527.

Leu, J. I., and George, D. L. (2007). Hepatic IGFBP1 is a prosurvival factor that binds to BAK, protects the liver from apoptosis, and antagonizes the proapoptotic actions of p53 at mitochondria. Genes & Dev. 21, 3095-3109.

Leu, J. I., Pimkina, J., Frank, A., Murphy, M. E., George, D. L. (2009). A small molecule inhibitor of inducible heat shock protein 70. Mol Cell. 36, 15-27.

Levine, B., and Kroemer, G. (2008). Autophagy in the pathogenesis of disease. Cell 132, 27-42.

Maclean, K. H., Dorsey, F. C., Cleveland, J. L., and Kastan, M. B. (2008). Targeting lysosomal degradation induces p53-dependent cell death and prevents cancer in mouse models of lymphomagenesis. J Clin Invest. 118, 79-88.

Mathew, R., Karp, C. M., Beaudoin, B., Vuong, N., Chen, G., Chen, H. Y., Bray, K., Reddy, A., Bhanot, G., Gelinas, C. et al. (2009). Autophagy suppresses tumorigenesis through elimination of p62. Cell. 137, 1062-1075.

Matsumoto, H., Shimura, M., Omatsu, T., Okaichi, K., Majima, H., and Ohnishi, T. (1994). p53 proteins accumulated by heat stress associate with heat shock proteins HSP72/HSC73 in human glioblastoma cell lines. Cancer Lett. 87, 39-46.

Mayer, M. P., and Bukau, B. (2005). Hsp70 chaperones: cellular functions and molecular mechanism. Cell. Mol. Life Sci. 62, 670-684.

McCarty, J. S., and Walker, G. C. (1994). DnaK mutants defective in ATPase activity are defective in negative regulation of the heat shock response: expression of mutant DnaK proteins results in filamentation. J Bacteriol. 176, 764-780.

McClellan, A. J., Tam, S., Kaganovich, D., and Frydman, J. (2005). Protein quality control: chaperones culling corrupt conformations. Nature Cell Biol. 7, 736-741.

McDonough, H., and Patterson, C. (2003). CHIP: a link between the chaperone and proteasome systems. Cell Stress Chaperones 8, 303-308.

Mehrpour, M., Esclatine, A., Beau, I., Codogno, P. (2010). Overview of macroautophagy regulation in mammalian cells. Cell Res. 20, 748-62.

Mimnaugh, E. G., Xu, W., Vos, M., Yuan, X., Neckers, L. (2006). Endoplasmic reticulum vacuolization and valosin-containing protein relocalization result from simultaneous Hsp90 inhibition by geldanamycin and proteasome inhibition by Velcade. Mol Cancer Res. 4, 6676-81.

Mimnaugh, E. G., Xu, W., Vos, M., Yuan, X., Isaacs, J. S., Bisht, K. S., et al. (2004). Simultaneous inhibition of hsp 90 and the proteasome promotes protein ubiquitination, causes endoplasmic reticulum-derived cytosolic vacuolization, and enhances antitumor activity. Mol Cancer Ther. 3, 551-66.

Mizushima, N., Levine, B., Cuervo, A. M., and Klionsky, D. J. (2008). Autophagy fights disease through cellular self-digestion. Nature. 451, 1069-1075.

Morimoto, R. I. (2008). Proteotoxic stress and inducible chaperone networks in neurodegenerative disease and aging. Genes & Dev. 22, 1427-1438.

Moscat, J., Diaz-Meco, M. T., and Wooten, M. W. (2007). Signal integration and diversification through the p62/SQSTM1 scaffold protein. Trends Biochem Sci. 32, 95-100.

Muchowski, P. J., and Wacker, J. L. (2005). Modulation of neurodegeneration by molecular chaperones. Nature Rev. Neurosci. 6, 11-22.

Murata, S., Chiba, T., Tanaka, K. (2003). CHIP: a quality control E3 ligasse collaborating with molecular chaperones. 35, 572-78.

Neckers, L. (2007). Heat shock protein 90: The cancer chaperone. J Biosci. 32, 517-30.

Nylandsted, J., Brand, K., and Jäätelä, M. (2000). Heat shock protein 70 is required for the survival of cancer cells. Ann N Y Acad Sci. 926, 122-125.

Nylandsted, J., Wick, W., Hirt, U. A., Brand, K., Rohde, M., Leist, M., Weller, M., and Jäätelä, M. (2002). Eradication of glioblastoma, and breast and colon carcinoma xenografts by Hsp70 depletion. Cancer Res. 62, 7139-42.

Nylandsted, J., Gyrd-Hansen, M., Danielewicz, A., Fehrenbacher, N., Lademann, U., Høyer-Hansen, M., Weber, E., Multhoff, G., Rohde, M., and Jäättelä, M. (2004). Heat shock protein 70 promotes cell survival by inhibiting lysosomal membrane permeabilization. J Exp Med. 200, 425-435.

Pankiv, S., Clausen, T. H., Lamark, T., Brech, A., Bruun, J. A., Outzen, H., Øvervatn, A., Bjørkøy, G., and Johansen, T. (2007). p62/SQSTM1 binds directly to Atg8/LC3 to facilitate degradation of ubiquitinated protein aggregates by autophagy. J Biol Chem. 282, 24131-24145.

Paine, M. G., Babu, J. R., Seibenhener, M. L., and Wooten, M. W. (2005). Evidence for p62/SQSTM1 aggregate formation: Role in cell survival. FEBS Lett. 579, 5029-5034.

Pimkina, J., Humbey, O., Zilfou, J. T., Jarnik, M., and Murphy, M. E. (2009). ARF Induces Autophagy by Virtue of Interaction with Bcl-xl. J Biol Chem. 284, 2803-2810.

Powers, M. V., and Workman, P. (2007). Inhibitors of the heat shock response: biology and pharmacology. FEBS Lett. 581, 3758-3769.

Powers, M. V., Clarke, P. A., and Workman, P. (2008). Dual targeting of HSC70 and HSP72 inhibits HSP90 function and induces tumor-specific apoptosis. Cancer Cell 14, 250-262.

Pridgeon, J. W., Geetha, T., and Wooten, M. W. (2003). A Method to Identify p62's UBA Domain Interacting Proteins. Biol Proced Online 5, 228-237.

Rohde, M., Daugaard, M., Jensen, M. H., Helin, K., Nylandsted, J., and Jäättelä, M. (2005). Members of the heat-shock protein 70 family promote cancer cell growth by distinct mechanisms. Genes Dev. 19, 570-582.

Ryhänen, T., Hyttinen, J. M., Kopitz, J., Rilla, K., Kuusisto, E., Mannermaa, E., Viiri, J., Holmberg, C. I., Immonen, I., Meri, S. et al. (2008). Crosstalk between Hsp70 molecular chaperone, lysosomes and proteasomes in autophagy-mediated proteolysis in human retinal pigment epithelial cells. J Cell Mol Med.

Saleh, A., Srinivasula, S. M., Balkir, L., Robbins, P. D., and Alnemri, E. S. (2000). Negative regulation of the Apaf-1 apoptosome by Hsp70. Nat. Cell Biol. 2, 476-483.

Salminen, A., Paimela, T., Suuronen, T., and Kaarniranta, K. (2008). Innate immunity meets with cellular stress at the IKK complex: regulation of the IKK complex by HSP70 and HSP90. Immunol Lett. 117, 9-15.

Schmitt, E., Maingret, L., Puig, P. E., Rerole, A. L., Ghirinhelli, F., Hammann, A., Solary, E., Kroemer, G., and Garrido, C. (2006). Heat shock protein 70 neutralization exerts potent antitumor effects in animal models of colon cancer and melanoma. Cancer Res. 66, 4191-4197.

Shvets, E., Fass, E., Scherz-Shouval, R., and Elazar, Z. (2008). The N-terminus and Phe52 residue of LC3 recruit p62/SQSTM1/SQSTM1 into autophagosomes. J Cell Sci. 121, 2685-2695.

Solimini, N. L., Luo, J., and Elledge, S. J. (2007). Non-oncogene addiction and the stress phenotype of cancer cells. Cell 130, 986-988.

Strom, E., Sathe, S., Komarov, P. G., Chernova, O. B., Pavlovska, I., Shyshynova, I., Bosykh, D. A., Burdelya, L. G., Macklis, R. M., Skaliter, R. et al. (2006). Small-molecule inhibitor of p53 binding to mitochondria protects mice from gamma radiation. Nat Chem Biol. 2, 474-479.

Tasdemir, E., Galluzzi, L., Maiuri, M. C., Criollo, A., Vitale, I., Hangen, E., Modjtahedi, N., and Kroemer, G. (2008). Methods for assessing autophagy and autophagic cell death. Methods Mol Biol 445, 29-76.

Townsend, P. A., Stephanou, A., Packham, G., and Latchman, D. S. (2005). BAG-1: a multifunctional pro-survival molecule. Int J Biochem Cell Biol. 37, 251-259.

Tutar, Y., Song, Y., and Masison, D. C. (2006). Primate chaperones Hsc70 (constitutive) and Hsp70 (induced) differ functionally in supporting growth and prion propagation in *Saccharomyces cerevisiae*. Genetics 172, 851-861.

Vos, M. J., Hageman, J., Carra, S., and Kampinga, H. H. (2008). Structural and functional diversities between members of the human HSPB, HSPH, HSPA, and DNAJ chaperone families. Biochemistry 47, 7001-7011.

Wegele, H., Müller, L., and Buchner, J. (2004). Hsp70 and Hsp90-a relay team for protein folding. Rev Physiol Biochem Pharmacol. 151, 1-44.

Whitesell L, Lindquist S L. (2005). HSP90 and the chaperoning of cancer. Nat Rev Cancer. 5, 761-72.

Wisén, S., and Gestwicki, J. E. (2008). Identification of small molecules that modify the protein folding activity of heat shock protein 70. Anal Biochem. 374, 371-377.

Wooten, M. W., Hu, X., Babu, J. R., Seibenhener, M. L., Geetha, T., Paine, M. G., and Wooten, M. C. (2006). Signaling, polyubiquitination, trafficking, and inclusions: sequestosome 1/p62/SQSTM1's role in neurodegenerative disease. J Biomed Biotechnol. 2006, 1-12.

Yang, Z., Klionsky, D. J. (2010) Eaten Alive: A history of macroautophagy. Nat Cell Biol. 12, 814-22.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treatment of neoplastic disease in vivo comprising co-administration of (i) a chemotherapeutic agent selected from the group consisting of temsirolimus, mechlorethamine, cyclophosphamide, ifosfamide, melphalan, chlorambucil, carmustine (BCNU), lomustine (CCNU), semustine (methyl-CCNU), Ethylenimine/Methylmelamine, thriethylenemelamine (TEM), triethylene thiophosphoramide (thiotepa), hexamethylmelamine (HMM), altretamine busulfan, dacarbazine (DTIC), methotrexate, trimetrexate, 5-fluorouracil, fluorodeoxyuridine, gemcitabine, cytosine arabinoside, 5-azacytidine, 2,2'-difluorodeoxycytidine, 6-mercaptopurine, 6-thioguanine, azathioprine, 2'-deoxycoformycin (pentostatin), erythrohydroxynonyladenine (EHNA), fludarabine phosphate, 2-Chlorodeoxyadenosine (cladribine, 2-CdA)), camptothecin, topotecan, irinotecan, paclitaxel, vinblastine (VLB), vincristine, and vinorelbine, Taxotere®, docetaxel, estramustine, estramustine phosphate, etoposide, teniposide, doxorubicin (adriamycin), mitoxantrone, idarubicin, bleomycins; plicamycin (mithramycin), mitomycinC, dactinomycin, L-asparaginase, interferon-alpha, IL-2, G-CSF, GM-CSF, retinoic acid derivatives, metronidazole, misonidazole, desmethylmisonidazole, pimonidazole, etanidazole, nimorazole, RSU 1069, E09, RB 6145, SR4233, nicotinamide, 5-bromodeozyuridine, 5-iododeoxyuridine, bromodeoxycytidine, cisplatin, carboplatin, mitoxantrone, hydroxyurea, N-methylhydrazine (MIH), procarbazine, aminoglutethimide, interferon β, interferon γ, interleukin-2, prednisone, dexamethasone, aminoglutethimide, hydroxyprogesterone caproate, medroxyprogesterone acetate, megestrol acetate, diethylstilbestrol, ethynyl estradiol, tamoxifen, testosterone propionate, fluoxymesterone, flutamide, leuprolide, hematoporphyrin derivatives, Photofrin®, benzoporphyrin derivatives, Npe6, tin etioporphyrin (SnET2), pheoboride-α, bacteriochlorophyll-a, naphthalocyanines, phthalocyanines, zinc phthalocyanines, bortezomib (Velcade®), epothilone, serratamolide, imatinib mesylate, dasatinib, nilotinib, MK-0457, and Omacetaxine, cetuximab, remicade and herceptin, and (ii) a compound of the formula

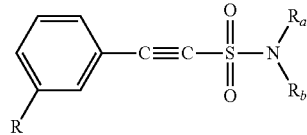

and pharmaceutically acceptable salts, wherein R represents a radical selected from the group consisting of chloro, alkyl ($C_1$-$C_4$), trifluoromethyl, amino, carboxy, hydroxyl and methoxy; $R_a$ and $R_b$ are the same or different and represent a radical selected from the group of hydrogen and alkyl ($C_1$-$C_6$), said compound being effective to inhibit heat shock protein (HSP) 70 function, and wherein said neoplastic disease is selected from the group consisting of osterosarcoma, B-cell lymphoma, lung cancer, melanoma, head and neck cancer, hepatoma, breast cancer, ovarian cancer, colon cancer and pancreatic cancer.

2. The method of claim 1 wherein said HSP70 function is selected from the group consisting of modulation of protein aggregation, chaperone protein binding, client protein binding, modulation of cellular stress response, modulation of autophagy, modulation of lysosomal functions, modulation of caspase cleavage, modulation of the proteasome system, reduced viability, modulation of anoikis, modulation of formation of detergent-insoluble subcellular complexes, modulation of NFκB activity, and modulation of vacuolization.

3. The method of claim 1, further comprising subjecting the patient to heat treatment.

4. A method for the treatment of neoplastic disease in a patient in need thereof comprising exposing cancer cells to effective amounts of radiation and a compound of the formula

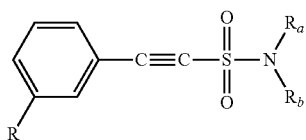

and pharmaceutically acceptable salts, wherein, R represents a substituent selected from the group consisting of chloro, alkyl ($C_1$-$C_4$), trifluoromethyl, amino, carboxy, hydroxyl and methoxy; $R_a$ and $R_b$ are the same or different and represent a radical selected from the group of hydrogen and alkyl ($C_1$-$C_6$), said radiation and said compound effectively killing cancer cells, and wherein said neoplastic disease is selected from the group consisting of osteorsarcoma, B-cell lymphoma, lung cancer, melanoma, head and neck cancer, hepatoma, breast cancer, ovarian cancer, colon cancer and pancreatic cancer.

5. The method of claim 4, wherein said radiation is selected from the group consisting of x-rays, gamma rays, neutron radiation, external-beam therapy, internal radiation therapy, implant radiation, brachytherapy, and systemic radiation.

6. The method of claim 4, optionally further comprising administration of an agent selected from the group consisting of herceptin, cetuximab and remicade.

7. The method of claim 1, wherein said compound disrupts HSP70 binding to at least one chaperone protein selected from the group consisting of CHIP, HSP40, and BAG-1M isoform.

8. The method of claim 1, wherein said compound disrupts HSP70 binding to at least one client protein selected from the group consisting of APAF-1, p53, LAMP-2, integrin α5, integrin β1, SV40 T antigen, and HSP90 client protein.

9. The method of claim 1, wherein said chemotherapeutic agent and said compound are administered simultaneously.

10. The method of claim 1, wherein said chemotherapeutic agent and said compound are administered sequentially.

11. The method of claim 1, wherein said chemotherapeutic agent and said compound are administered via a route selected from the group consisting of intravenous, intramuscular, subcutaneous, rectal, intraocular, intrasynovial, transepithelial, transdermal, ophthalmic, sublingual, buccal, topically and inhalation via insufflation aerosol.

12. The method of claim 1, further comprising co-administration of an HSP 90 inhibitor.

13. The method of claim 8, wherein said HSP90 client protein is selected from the group consisting of EGFR, HER2/ErbB2, AKT.

14. A method of claim 1 comprising administration of the compound of the formula:

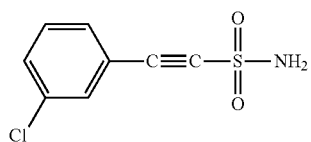 [SMILES: NS(=O)(=O)C#Cc1cccc(Cl)c1]

and pharmaceutically acceptable salts thereof.

15. The method of claim 4 wherein said HSP70 function is selected from the group consisting of modulation of protein aggregation, chaperone protein binding, client protein binding, modulation of cellular stress response, modulation of autophagy, modulation of lysosomal functions, modulation of NFκB activity, modulation of caspase cleavage, modulation of the proteasome system, reduced viability, modulation of anoikis, modulation of formation of detergent-insoluble subcellular complexes, and modulation of vacuolization.

16. The method of claim 4, wherein said compound disrupts HSP70 binding to at least one chaperone protein selected from the group consisting of CHIP, HSP40, and BAG-1M isoform.

17. The method of claim 4, wherein said compound disrupts HSP70 binding to at least one client protein selected from the group consisting of APAF-1, p53, LAMP-2, integrin α5, integrin β1, SV40 T antigen, and HSP90 client protein.

18. The method of claim 4, further comprising co-administration of an HSP 90 inhibitor.

19. The method of claim 17, wherein said HSP90 client protein is selected from the group consisting of EGFR, HER2/ErbB2, AKT.

20. A method of claim 4 comprising administration of the compound of the formula:

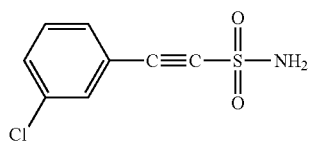 [SMILES: NS(=O)(=O)C#Cc1cccc(Cl)c1]

and pharmaceutically acceptable salts thereof.

* * * * *